US009828637B2

(12) United States Patent
Genovese et al.

(10) Patent No.: US 9,828,637 B2
(45) Date of Patent: Nov. 28, 2017

(54) METHODS OF PREDICTING PREDISPOSITION TO OR RISK OF KIDNEY DISEASE

(75) Inventors: Giulio Genovese, Boston, MA (US); David J. Friedman, Boston, MA (US); Martin R. Pollak, Boston, MA (US); Barry I. Freedman, Winston-Salem, NC (US)

(73) Assignees: Wake Forest University Health Sciences, Winston-Salem, NC (US); Beth Israel Deaconess Medical Center, Inc., Boston, MA (US)

( * ) Notice: Subject to any disclaimer, the term of this patent is extended or adjusted under 35 U.S.C. 154(b) by 0 days.

(21) Appl. No.: 13/642,054

(22) PCT Filed: Apr. 18, 2011

(86) PCT No.: PCT/US2011/032924
§ 371 (c)(1),
(2), (4) Date: Dec. 12, 2012

(87) PCT Pub. No.: WO2011/133474
PCT Pub. Date: Oct. 27, 2011

(65) Prior Publication Data
US 2013/0079244 A1 Mar. 28, 2013

Related U.S. Application Data

(60) Provisional application No. 61/325,343, filed on Apr. 18, 2010.

(51) Int. Cl.
*C40B 30/04* (2006.01)
*C12Q 1/68* (2006.01)

(52) U.S. Cl.
CPC ...... *C12Q 1/6883* (2013.01); *C12Q 2600/118* (2013.01); *C12Q 2600/156* (2013.01); *C12Q 2600/158* (2013.01); *C12Q 2600/172* (2013.01)

(58) Field of Classification Search
CPC .............................. C12Q 1/6883; C12Q 1/68
USPC .......................................................... 506/9
See application file for complete search history.

(56) References Cited

U.S. PATENT DOCUMENTS

| | | | |
|---|---|---|---|
| 5,427,930 A | 6/1995 | Birkenmeyer et al. | |
| 5,744,311 A | 4/1998 | Fraiser et al. | |
| 5,981,185 A | 11/1999 | Matson et al. | |
| 6,025,134 A | 2/2000 | Sooknanan | |
| 6,027,889 A | 2/2000 | Barany et al. | |
| 6,033,881 A | 3/2000 | Himmler et al. | |
| 7,747,392 B2 * | 6/2010 | Ruano et al. ................ | 702/19 |
| 2005/0009016 A1 | 1/2005 | Moskowitz et al. | |
| 2005/0142596 A1 | 6/2005 | Krolewski et al. | |
| 2007/0065820 A1 * | 3/2007 | Jiang et al. ................. | 435/6 |
| 2008/0057503 A1 * | 3/2008 | Abbas et al. ................ | 435/6 |
| 2009/0075254 A1 * | 3/2009 | Ruano et al. ............... | 435/6 |
| 2009/0162333 A1 | 6/2009 | Pays et al. | |
| 2010/0120781 A1 | 5/2010 | Neamati | |
| 2010/0297660 A1 * | 11/2010 | Winkler et al. ............. | 435/6 |
| 2012/0128682 A1 * | 5/2012 | Pays et al. ............. | 424/139.1 |
| 2012/0195902 A1 * | 8/2012 | Friedman ........... | G01N 33/6893 424/139.1 |

FOREIGN PATENT DOCUMENTS

| | | | |
|---|---|---|---|
| EP | 0 320 308 A2 | 6/1989 | |
| GB | WO 9319201 A1 * | 9/1993 | .......... C12Q 1/6827 |
| WO | WO 90/01069 A1 | 2/1990 | |
| WO | WO-2004/012757 A2 | 2/2004 | |
| WO | WO 2004012757 A2 * | 2/2004 | |
| WO | WO 2011020865 A1 * | 2/2011 | |
| WO | WO 2011071935 A2 * | 6/2011 | |
| WO | WO-2011/133474 A2 | 10/2011 | |
| WO | WO-2012/162394 A2 | 11/2012 | |

OTHER PUBLICATIONS

Geneovese et al.; Screenshote, Association of Trypanolytic ApoL1 Variants with Kidney Disease in African Americans, Science, 2010, 329(5993), 841.*
Titan et al., Letter to the Editor, HIV Infection and Acute Glomerulonephritis, 2007, 62(5), 653-656.*
Eberle et al., Power to Detect Risk Alleles Using Genome-Wide Tag SNP Panels, PLoS Genetics, 2007, 3(10), 1827-1837.*
SCORE Results; file 20130625_125127_us-13-642-054-1.rng, 2013, 1-41.*
SCORE Results; file 20130625_125127_us-13-642-054-2.rng, 2013, 1-39.*
Velthuysen et al., Glomerulopathy Associated with Parasitic Infections, Clincial Microbiology Reviews, 2000, 55-60.*
Hildebrandt, F., Genetic Kidney Diseases, NIH Public Access, Author Manuscript, 2010, 1-19 and published in final form in Lancet, 2010, 375(9722); 1287-1295.*
*Ariosa Diagnostics, Inc. v. Sequenom, Inc.*, Opinion of the United States Court of Appeals for the Federal Circuit; 2015, 1-21.*
Kitssios et al., Human Genome Epidemiology (HuGE) Review, Genetic Variation Association with Ischemic Heart Failure: A HugE Reveiw and Meta-Analysis, Am J Epidemol, 2007, 166(6), 619-633.*

(Continued)

*Primary Examiner* — Amy M Bunker
(74) *Attorney, Agent, or Firm* — Myers Bigel, P.A.

(57) ABSTRACT

Methods are disclosed herein for detecting a genetic predisposition to focal segmental glomerulosclerosis (FSGS) or hypertensive end-stage kidney disease (ESKD) or both in a human subject, e.g., by detecting the presence of at least one single nucleotide polymorphism (SNP) in an APOL1 gene, such as the C-terminal exon of an APOL1 gene. In a further embodiment, methods are disclosed for detecting resistance of a subject to a disease associated with *Trypanosoma* infection, e.g., by detecting at least one single nucleotide polymorphism (SNP) in an APOL1 gene, such as the C-terminal exon of an APOL1 gene. Also disclosed are methods for treating a subject infected with *T. brucei*. The methods include administering a therapeutically effective amount of an APOL1 protein including a S342G substitution, an I384M substitution, and/or a deletion of N388 and Y389 to the subject.

5 Claims, 12 Drawing Sheets

(56) References Cited

OTHER PUBLICATIONS

Bleumink et al., Review, Genetic Polymorphisms and Heart Failure, Genetics in Medicine, 2004, 6(6), 465-474.*
Score Results; Supplemental Content, Result 13, 20140919_090509_us-13-642-054-3.rng, 2014, 1-40.*
Reeves-Daniel et al., The Apol1 Gene and Allograft Survival After Kidney Transplantation, American Journal of Transplantation, 2011, 11, 1025-1030.*
Freedman et al., "The apolipoprotein L1 (APOL1) gene and nondiabetic nephropathy in African Americans," J Am Soc Nephrol. 21(9):1-5 (2010).
Genovese et al., "Association of trypanolytic ApoL1 variants with kidney disease in African Americans," Science. 329(5993):841-5 (2010).
Gibson et al., "The human serum resistance associated gene is ubiquitous and conserved in Trypanosoma brucei rhodesiense throughout East Africa," Infect Genet Evol. 1(3):207-14 (2002).
Li et al., "Distribution and effect of apoL-I genotype on plasma lipid and apolipoprotein levels in Chinese normalipidemic and endogenous hypertriglyceridemic subjects," Clin Chim Acta. 403(1-2):152-5 (2009).
NCBI Reference SNP(refSNP) Cluster Report: rs60910145, <http://www.ncbi.nlm.nih.gov/projects/SNP/snp_ref.cgi?rs=60910145>, retrieved on Dec. 15, 2011 (3 pages).
NCBI Reference SNP(refSNP) Cluster Report: rs73885319, <http://www.ncbi.nlm.nih.gov/projects/SNP/snp_ref.cgi?rs=73885319>, retrieved Dec. 15, 2011 (3 pages).
Paul, "Genes linked to kidney disease," Genetics Abstract, <http://geneticsabstracts.blogspot.com/2008/10/genese-linked-to-kidney-disease.thml>, retrieved on Aug. 22, 2011 (2 pages).
Tzur et al., "Missense mutations in the APOL1 gene are highly associated with end stage kidney disease risk previously attributed to the MYH9 gene," Hum Genet. 128(3):345-50 (2010).
Vanhollebeke et al., "Human Trypanosoma evansi infection linked to a lack of apolipoprotein L-I," N Engl J Med. 355(26):2752-6 (2006).
Vanhollebeke et al., "Distinct roles of haptoglobin-related protein and apolipoprotein L-I in trypanolysis by human serum," Proc Natl Acad Sci USA. 104(10):4118-23 (2007).
International Search Report for International Application No. PCT/US2011/32924, dated Apr. 9, 2012 (6 pages).
International Search Report and Written Opinion of the International Searching Authority for International Application No. PCT/US2012/039145, dated Dec. 7, 2012 (14 pages).
Office Action in U.S. Appl. No. 13/404,725 dated Aug. 26, 2013 (11 pages).
Written Opinion of the International Searching Authority for International Application No. PCT/US2011/32924, dated Apr. 9, 2012 (8 pages).
Kiberstis. "Letter and reviews from Science (1189125)". E-mail to Martin Pollak. Mar. 16, 2010 (3 pages).
Altschul et al. "Basic Local Alignment Search Tool" *Journal of Molecular Biology* 215:403-410 (1990).
Ayodo et al. "Combining Evidence of Natural Selection with Association Analysis Increases Power to Detect Malaria-Resistance Variants" *The American Journal of Human Genetics* 81:234-242 (2007).
Barany, Francis "Genetic disease detection and DNA amplification using cloned thermostable ligase" *Proceedings of the National Academy of Sciences*, USA 88:189-193 (1991).
Barisoni et al. "A Proposed Taxonomy for the Podocytopathies: A Reassessment of the Primary Nephrotic Diseases" *Clinical Journal of the American Society of Nephrology* 2:529-542 (2007).
Barreiro et al. "Natural selection has driven population differentiation in modern humans" *Nature Genetics* 40(3):340-345 (2008).
Behar et al. "African ancestry allelic variation at the MYH9 gene contributes to increased susceptibility to non-diabetic end-stage kidney disease in Hispanic Americans" *Human Molecular Genetics* 19(9):1816-1827 (2010).

Beltz et al. "Isolation of Multigene Families and Determination of Homologies by Filter Hybridization Methods" *Methods in Enzymology* 100:266-285 (1983).
Browning et al. "A Unified Approach to Genotype Imputation and Haplotype-Phase Interference for Large Data Sets of Trios and Unrelated Individuals" *The American Journal of Human Genetics* 84:210-223 (2009).
Coresh et al. "Prevalence of Chronic Kidney Disease and Decreased Kidney Function in the Adult US Population: Third National Health and Nutrition Examination Survey" *American Journal of Kidney Diseases* 41(1):1-12 (2003).
Corpet, Florence "Multiple sequence alignment with hierarchical clustering" *Nucleic Acids Research* 16(22):10881-10890 (1988).
Cowie et al. "Disparities in Incidence of Diabetic End-Stage Renal Disease According to Race and Type of Diabetes" *The New England Journal of Medicine* 321:1074-1079 (1989).
Derose et al. "Incidence of end-stage renal disease and death among insured African Americans with chronic kidney disease" *Kidney International* 76:629-637 (2009).
Eggers et al. "Is There an Epidemic of HIV Infection in the US ESRD Program?" *Journal of the American Society of Nephrology* 15:2477-2485 (2004).
Excoffier et al. "Genetics and History of Sub-Saharan Africa" *Yearbook of Physical Anthropology* 30:151-194 (1987).
Fernandez et al. "A Multiethnic, Multicenter Cohort of Patients With Systemic Lupus Erythematosus (SLE) as a Model for the Study of Ethnic Disparities in SLE" *Arthritis & Rheumatism* 57(4):576-584 (2007).
Frazer et al. "A second generation human haplotype map of over 3.1 million SNPs" *Nature* 449(7164):851-861 (2007).
Freedman et al. "Family History of End-Stage Renal Disease among Incident Dialysis Patients" *Journal of the American Society of Nephrology* 8:1942-1945 (1997).
Freedman et al. "Polymorphisms in the non-muscle myosin heavy chain 9 gene (*MYH9*) are strongly associated with end-stage renal disease historically attributed to hypertension in African Americans" *Kidney International* 75:736-745 (2009).
GenBank Accession No. AAI42721 "APOL1 protein, partial [*Homo sapiens*]" *NCBI* (2 pages) (Jun. 11, 2007).
GenBank Accession No. AAI43039 "APOL1 protein [*Homo sapiens*]" *NCBI* (2 pages) (Jun. 13, 2007).
GenBank Accession No. AF305224 "*Homo sapiens* apolipoprotein L1 mRNA, complete cds" *NCBI* (2 pages) (May 25, 2001).
GenBank Accession No. BC127186 "*Homo sapiens* apolipoprotein L, 1, mRNA (cDNA clone MGC:156903 Image:40034503), complete cds" *NCBI* (3 pages) (Mar. 19, 2007).
GenBank Accession No. CAQ09089 "apolipoprotein L, 1 [*Homo sapiens*]" *NCBI* (2 pages) (May 6, 2008).
GenBank Accession No. NC_000022 "*Homo sapiens* chromosome 22, GRCh38.p7 Primary Assembly" *NCBI* (2 pages) (Jun. 6, 2016).
GenBank Accession No. NM_003661 "*Homo sapiens* apolipoprotein L1 (APOL1), transcript variant 1, mRNA" *NCBI* (5 pages) (Oct. 6, 2016).
GenBank Accession No. NM_145343 "*Homo sapiens* apolipoprotein L1 (APOL1), transcript variant 2, mRNA" *NCBI* (5 pages) (Oct. 6, 2016).
GenBank Accession No. NM_001136540 "*Homo sapiens* apolipoprotein L1 (APOL1), transcript variant 3, mRNA" *NCBI* (5 pages) (Oct. 6, 2016).
GenBank Accession No. NP_003652 "apolipoprotein L1 isoform a recursor [*Homo sapiens*]" *NCBI* (3 pages) (Oct. 6, 2016).
GenBank Accession No. Z82215 "Human DNA sequence from clone RP1-68O2 on chromosome 22, complete sequence" *NCBI* (31 pages) (Jan. 24, 2013).
Genovese et al. "A risk allele for focal segmental glomerulosclerosis in African Americans is located within a region containing APOL1 and MYH9" *Kidney International* 78:698-704 (2010).
Gibbs et al. "Detection of single DNA base differences by competitive oligonucleotide priming" *Nucleic Acids Research* 17(7):2437-2448 (1989).
Gibson, W.C. "Will the real *Trypanosoma b. gambiense* please stand up" *Parasitology Today* 2(9):255-257 (1986).

(56) References Cited

OTHER PUBLICATIONS

Gibson, Wendy "Will the real *Trypanosoma brucei rhodesiense* please step forward?" *Trends in Parasitology* 18(11):486-490 (2002).
Grompe et al. "Improved Molecular Diagnostics for Ornithine Transcarbamylase Deficiency" *The American Journal of Human Genetics* 48:212-222 (1991).
Grossman et al. "A Composite of Multiple Signals Distinguishes Causal Variants in Regions of Positive Selection" *Science* 327(5967):883-886 (2010).
Halperin et al. "Tag SNP selection in genotype data for maximizing SNP prediction accuracy" *Bioinformatics* 21(Suppl. 1)1195-i203 (2005).
Higgins et al. "Clustal: a package for performing multiple sequence alignment on a microcomputer" *Gene* 73:237-244 (1988).
Higgins et al. "Fast and sensitive multiple sequence alignments on a microcomputer" *Cabios Communications* 5(2):151-153 (1989).
Hsu et al. "Racial Differences in the Progression from Chronic Renal Insufficiency to End-Stage Renal Disease in the United States" *Journal of the American Society of Nephrology* 14:2902-2907 (2003).
Huang et al. "Parallelization of a local similarity algorithm" *Cabios* 8(2):155-165 (1992).
Kao et al. "*MYH9* is associated with nondiabetic end-stage renal disease in African Americans" *Nature Genetics* 40(10):1185-1192 (2008).
Kiberd et al. "Cumulative Risk for Developing End-Stage Renal Disease in the US Population" *Journal of the American Society of Nephrology* 13:1635-1644 (2002).
Kimura et al. "A Practical Genome Scan for Population-Specific Strong Selective Sweeps That Have Reached Fixation" *PLoS One* 2(3):e286 (2007).
Kinchen et al. "The Timing of Specialist Evaluation in Chronic Kidney Disease and Mortality" *Annals of Internal Medicine* 137(6):479-486 (2002).
Kitiyakara et al. "Trends in the epidemiology of focal segmental glomerulosclerosis" *Seminars in Nephrology* 23(2):172-182 (2003) (Abstract Only).
Kitiyakara et al. "Twenty-One-Year Trend in ESRD Due to Focal Segmental Glomerulosclerosis in the United States" *American Journal of Kidney Diseases* 44(5):815-825 (2004).
Klag et al. "End-stage Renal Disease in African-American and White Men: 16-Year MRFIT Findings" *JAMA* 277(16):23-30 (1997).
Kopp et al. "HIV-associated nephropathy in African Americans" *Kidney International* 63(Suppl. 83):S43-S49 (2003).
Kopp et al. "*MYH9* is a major-effect risk gene for focal segmental glomerulosclerosis" *Nature Genetics* 40(10):1175-1184 (2008).
Lecordier et al. "C-Terminal Mutants of Apolipoprotein L-I Efficiently Kill Both *Trypanosoma brucei brucei* and *Trypanosoma brucei rhodesiense*" *PLoS Pathogens* 5(12):e1000685 (2009).
Levey et al. "A More Accurate Method to Estimate Glomerular Filtration Rate from Serum Creatinine: A New Prediction Equation" *Annals of Internal Medicine* 130(6):461-470 (1999).
McKenzie et al. "*NPHS2* Variation in Sporadic Focal Segmental Glomerulosclerosis" *Journal of the American Society of Nephrology* 18:2987-2995 (2007).
Melamed et al. "25-Hydroxyvitamin D Levels, Race, and the Progression of Kidney Disease" *Journal of the American Society of Nephrology* 20:2631-2639 (2009).
Myers et al. "Detection and Localization of Single Base Changes by Denaturing Gradient Gel Electrophoresis" *Methods in Enzymology* 155:501-527 (1987).
Needleman et al. "A General Method Applicable to the Search for Similarities in the Amino Acid Sequence of Two Proteins" *Journal of Molecular Biology* 48:443-453 (1970).

Nelson et al. "Genomic mismatch scanning: a new approach to genetic linkage mapping" *Nature Genetics* 4:11-18 (1993).
Nelson et al. "Dense mapping of MYH9 localizes the strongest kidney disease associations to the region of introns 13 to 15" *Human Molecular Genetics* 19(9):1805-1815 (2010).
Orita et al. "Detection of polymorphisms of human DNA by gel electrophoresis as single-strand conformation polymorphisms" *Proceedings of the National Academy of Sciences USA* 86:2766-2770 (1989).
Orloff et al. "Variants in the Wilms' tumor gene are associated with focal segmental glomerulosclerosis in the African American population" *Physiological Genomics* 21:212-221 (2005).
Pearson et al. "Improved tools for biological sequence comparison" *Proceedings of the National Academy of Sciences USA* 85:2444-2448 (1988).
Pearson, William R. "Using the FASTA Program to Search Protein and DNA Sequence Databases" *Methods in Molecular Biology* 24:307-331 (1994).
Perez-Morga et al. "Apolipoprotein L-1 Promotes Trypanosome Lysis by Forming Pores in Lysosomal Membranes" *Science* 309(5733):469-472 (2005).
Reference SNP (RefSNP) No. rs11912763 "human (*Homo sapiens*)" *NCBI* (3 pages) (Jun. 7, 2016).
Reference SNP (RefSNP) No. rs2239786 "human (*Homo sapiens*)" *NCBI* (3 pages) (Nov. 28, 2016).
Reference SNP (RefSNP) No. rs71785313 "human (*Homo sapiens*)" *NCBI* (2 pages) (Jun. 7, 2016).
Sabeti et al. "Detecting recent positive selection in the human genome from haplotype structure" *Nature* 419:832-837 (2002).
Saiki et al. "Analysis of enzymatically amplified β-globin and HLA-DQα DNA with allele-specific oligonucleotide probes" *Nature* 324:163-166 (1986).
Shurraw et al. "Glycemic Control and the Risk of Death in 1,484 Patients Receiving Maintenance Hemodialysis" *American Journal of Kidney Diseases* 55(5):875-884 (2010).
Smith et al. "Comparison of Biosequence" *Advances in Applied Mathematics* 2:482-489 (1981).
Tarver-Carr et al. "Excess Risk of Chronic Kidney Disease among African-Americans versus White Subjects in the United States: A Population-Based Study of Potential Explanatory Factors" *Journal of the American Society of Nephrology* 13:2363-2370 (2002).
Toto, Robert D. "Proteinuria and hypertensive nephrosclerosis in African Americans" *Kidney International* 66(Supplement 92):S102-S104 (2004).
Truc et al. "Evaluation of the micro-CATT, CATT/*Trypanosoma brucei gambiense*, and LATEX/*T. b. gambiense* methods for serodiagnosis and surveillance of human African trypanosomiasis in West and Central Africa" *Bulletin of the World Health Organization* 80(11):882-886 (2002).
Vanhamme et al. "Apolipoprotein L-1 is the trypanosome lytic factor of human serum" *Nature* 422:83-87 (2003).
Voight et at. "A Map of Recent Positive Selection in the Human Genome" *PLoS Biology* 4(3):e72 (2006).
Volkova et al. "Neighborhood Poverty and Racial Differences in ESRD Incidence" *Journal of the American Society of Nephrology* 19:356-364 (2008).
Walker et al. "Renal Function Change in Hypertensive Members of the Multiple Risk Factor Intervention Trial: Racial and Treatment Effects" *Jama* 268(21):3085-3091 (1992).
Wu et al. "The Ligation Amplification Reaction (LAR)—Amplification of Specific DNA Sequences Using Sequential Rounds of Template-Dependent Ligation" *Genomics* 4:560-569 (1989).
Xong et al. "A *VSG* Expression Site-Associated Gene Confers Resistance to Human Serum in *Trypanosoma rhodesiense*" *Cell* 95:839-846 (1998).

\* cited by examiner

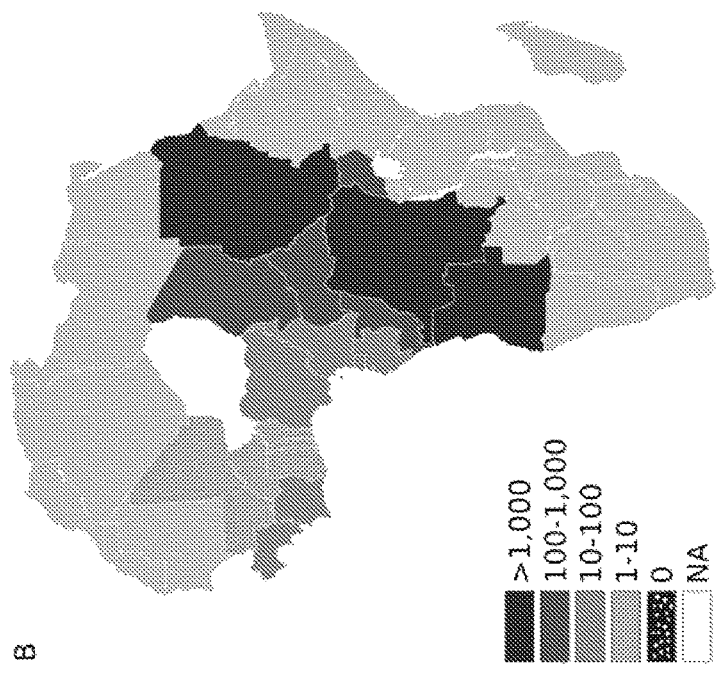
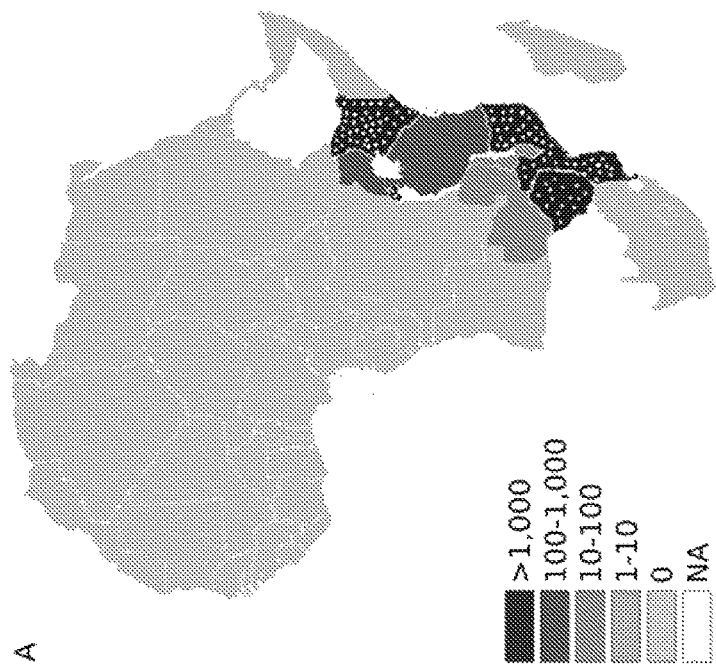
FIG. 3

FIG. 10

|     |          |          |          |          |          |
|-----|----------|----------|----------|----------|----------|
| 181 | AGAACGCCCT | CTGCATAGTC | CCCTGGTGAA | CTGCTGCCCA | APOL1 sequence |
| 241 | GGACTGGGTC | CCCCTTTTAC | CCTTGCTGCA | TGGAGTCCCG |          |
| 241 | AGAAGACAAA | CATCTGTGTG | TCTGAACCCT | GAGACAAAGG |          |
| 301 | CAGGAAAGGC | AAAGAGGGAG | GCGAGTGGCT | TTTGAGGAGG |          |
| 361 | CGGCTTTAGT | ATGAACACTG | CAGGATGGAA | CCCCATCAGG |          |
| 421 | GGCCCCGGGA | ACCACTGACC | TGTTAAAATA | AAGTCTGCAA |          |
| 481 | ACAAAGACCA | GCTGCTGGAA | GTGGTGTGC | CAGGGAGTGC |          |
| 541 | GCAGGAGACAC | ACGGTGAGAA | AAGAACAATG | GTAATGCTTG |          |
| 601 | GAGGCGCGCC | TAACTGGGAT | GGGCCTGAAG | TGGTATTGTT |          |
| 661 | ATTATTATA | GTATCATTAT | TAGTCATTT | CATCTATT |          |
| 721 | GTACCCTCCC | TCTATCTCTT | CTCTCCACCT | TTTCCTAACA |          |
| 781 | TCTATCACC | AGTTTTATGT | CTCCCATTAG | CAACTTGTA |          |
| 841 | GCTGTAAACA | ATTACTTAAC | AACTTCTTTA | TACCCTCAGT | APOL4 sequence |
| 901 | TGTACCAGT | ATTTCTTAAC | TTCCCTCTTT | AAAAATGAC |          |
| 961 | AATATTAATC | CTCTTCTCC | TTGTCAGT | GCTTCGCATC |          |

SEQUENCE LISTING

<160> NUMBER OF SEQ ID NOS: 9

<210> SEQ ID NO 1
<211> LENGTH: 52
<212> TYPE: DNA
<213> ORGANISM: Homo sapiens

<400> SEQUENCE: 1
tcaagctcac ggatgtggcc cctgtargct tctttcttgt gctggatgta gt        52

<210> SEQ ID NO 2
<211> LENGTH: 52
<212> TYPE: DNA
<213> ORGANISM: Homo sapiens

<400> SEQUENCE: 2
caggagctgg aggagaagct aaacatkctc aacaataatt ataagattct gc        52

<210> SEQ ID NO 3
<211> LENGTH: 57
<212> TYPE: DNA
<213> ORGANISM: Homo sapiens
<220> FEATURE:
<221> NAME/KEY: misc_feature
<222> LOCATION: (27)..(32)
<223> OTHER INFORMATION: This region may or may not be present

<400> SEQUENCE: 3
gagaagctaa acattctcaa caataattat aagattctgc aggcggacca agaactg    57

<210> SEQ ID NO 4
<211> LENGTH: 1197
<212> TYPE: DNA
<213> ORGANISM: Homo sapiens

<400> SEQUENCE: 4
atggagggag ctgctttgct gagagtctct gtcctctgca tctggatgag tgcacttttc     60
cttggtgtgg gagtgagggc agaggaagct ggagcgaggg tgcaacaaaa cgttccaagt    120
gggacagata ctggagatcc tcaaagtaag cccctcggtg actgggctgc tggcaccatg    180
gacccagaga gcagtatctt tattgaggat gccattaagt atttcaagga aaaagtgagc    240
acacagaatc tgctactcct gctgactgat aatgaggcct ggaacggatt cgtggctgct    300
gctgaactgc caggaatgaa ggcagatgag ctccgtaaag ctctggacaa ccttgcaaga    360
caaatgatca tgaaagacaa aaactggcac gataaaggcc agcagtacag aaactggttt    420
ctgaaagagt ttcctcggtt gaaaagtgag cttgaggata acataagaag gctccgtgcc    480
cttgcagatg gggttcagaa ggtccacaaa ggcaccacca tcgccaatgt ggtgtctggc    540
tctctcagca tttcctctgg catcctgacc ctcgtcggca tgggtctggc acccttcaca    600
gagggaggca gccttgtact cttggaacct gggatggagt tgggaatcac agccgctttg    660
accgggatta ccagcagtac catggactac ggaaagaagt ggtggacaca agcccaagcc    720
cacgacctgg tcatcaaaag ccttgacaaa ttgaaggagg tgagggagtt tttgggtgag    780
aacatatcca actttctttc cttagctggc aatacttacc aactcacacg aggcattggg    840
aaggacatcc gtgccctcag acgagccaga gccaatcttc agtcagtacc gcatgcctca    900
gcctcacgcc cccgggtcac tgagccaatc tcagctgaaa gcggtgaaca ggtggagagg    960
gttaatgaac ccagcatcct ggaaatgagc agaggagtca agctcacgga tgtggcccct   1020
gtaagcttct ttcttgtgct ggatgtagtc tacctcgtgt acgaatcaaa gcacttacat   1080

```
gagggggcaa agtcagagac agctgaggag ctgaagaagg tggctcagga gctggaggag   1140
aagctaaaca ttctcaacaa taattataag attctgcagg cggaccaaga actgtga      1197
```

<210> SEQ ID NO 5
<211> LENGTH: 398
<212> TYPE: PRT
<213> ORGANISM: Homo sapiens

<400> SEQUENCE: 5

```
Met Glu Gly Ala Ala Leu Leu Arg Val Ser Val Leu Cys Ile Trp Met
1               5                   10                  15

Ser Ala Leu Phe Leu Gly Val Gly Val Arg Ala Glu Glu Ala Gly Ala
            20                  25                  30

Arg Val Gln Gln Asn Val Pro Ser Gly Thr Asp Thr Gly Asp Pro Gln
        35                  40                  45

Ser Lys Pro Leu Gly Asp Trp Ala Ala Gly Thr Met Asp Pro Glu Ser
50                  55                  60

Ser Ile Phe Ile Glu Asp Ala Ile Lys Tyr Phe Lys Glu Lys Val Ser
65                  70                  75                  80

Thr Gln Asn Leu Leu Leu Leu Thr Asp Asn Glu Ala Trp Asn Gly
            85                  90                  95

Phe Val Ala Ala Ala Glu Leu Pro Arg Asn Glu Ala Asp Glu Leu Arg
            100                 105                 110

Lys Ala Leu Asp Asn Leu Ala Arg Gln Met Ile Met Lys Asp Lys Asn
        115                 120                 125

Trp His Asp Lys Gly Gln Gln Tyr Arg Asn Trp Phe Leu Lys Glu Phe
130                 135                 140

Pro Arg Leu Lys Ser Glu Leu Glu Asp Asn Ile Arg Arg Leu Arg Ala
145                 150                 155                 160

Leu Ala Asp Gly Val Gln Lys Val His Lys Gly Thr Thr Ile Ala Asn
                165                 170                 175

Val Val Ser Gly Ser Leu Ser Ile Ser Ser Gly Ile Leu Thr Leu Val
            180                 185                 190

Gly Met Gly Leu Ala Pro Phe Thr Glu Gly Gly Ser Leu Val Leu Leu
        195                 200                 205

Glu Pro Gly Met Glu Leu Gly Ile Thr Ala Ala Leu Thr Gly Ile Thr
210                 215                 220

Ser Ser Thr Met Asp Tyr Gly Lys Lys Trp Trp Thr Gln Ala Gln Ala
225                 230                 235                 240

His Asp Leu Val Ile Lys Ser Leu Asp Lys Leu Lys Glu Val Arg Glu
                245                 250                 255

Phe Leu Gly Glu Asn Ile Ser Asn Phe Leu Ser Leu Ala Gly Asn Thr
            260                 265                 270

Tyr Gln Leu Thr Arg Gly Ile Gly Lys Asp Ile Arg Ala Leu Arg Arg
        275                 280                 285

Ala Arg Ala Asn Leu Gln Ser Val Pro His Ala Ser Ala Ser Arg Pro
290                 295                 300

Arg Val Thr Glu Pro Ile Ser Ala Glu Ser Gly Glu Gln Val Glu Arg
305                 310                 315                 320

Val Asn Glu Pro Ser Ile Leu Glu Met Ser Arg Gly Val Lys Leu Thr
                325                 330                 335

Asp Val Ala Pro Val Ser Phe Phe Leu Val Leu Asp Val Tyr Leu
            340                 345                 350
```

```
Val Tyr Glu Ser Lys His Leu His Glu Gly Ala Lys Ser Glu Thr Ala
            355                 360                 365

Glu Glu Leu Lys Lys Val Ala Gln Glu Leu Glu Lys Leu Asn Ile
    370                 375                 380

Leu Asn Asn Asn Tyr Lys Ile Leu Gln Ala Asp Gln Glu Leu
385                 390                 395

<210> SEQ ID NO 6
<211> LENGTH: 6
<212> TYPE: DNA
<213> ORGANISM: Homo sapiens

<400> SEQUENCE: 6 ttataa                                                                  6

<210> SEQ ID NO 7
<211> LENGTH: 599
<212> TYPE: DNA
<213> ORGANISM: Homo sapiens

<400> SEQUENCE: 7
agacgcccct ctgcatactc ccctggtgaa ctgctgccca ggactgggtc ccccttttac       60
ccttgctgca tggagtcccc agaagacaaa catctgtgtg tctgaaccct gagacaaagg      120
caggaaaggg aaagagggag gcgagtggct tttgaggagg gggctttagt atgagagctg      180
gaggatggaa ccccatcagg gggcccggga accactgagc tgttaaaata aagtctgcaa      240
acaaagacca gctgctggaa gtgggtgtgc cagggagtgc gcagagacac acggtgagaa      300
aagaacaatg gtaatgcttg gagccgcccc taactgggat gggcctgaag tggtattgtt      360
attatttata gtatcattat tagtcatttt catcttattt gtaccctccc tctatctctc      420
tctccacctt ttcctaacat tctatcacca gttttatgtc tcccattagc aactttgtag      480
ctgtaaacaa tttacttaca actttcttat accctcagtt gtaccagta tttcttaact       540 tccctcttta aaaaatgaca atattaatcc tccttctcct ttgttcagtg cttcacatc       599

<210> SEQ ID NO 8
<211> LENGTH: 16
<212> TYPE: DNA
<213> ORGANISM: Homo sapiens

<400> SEQUENCE: 8
agcgtcgggt gagtcc                                                       16

<210> SEQ ID NO 9
<211> LENGTH: 11
<212> TYPE: DNA
<213> ORGANISM: Homo sapiens

<400> SEQUENCE: 9
aacaggatga g                                                            11
```

METHODS OF PREDICTING PREDISPOSITION TO OR RISK OF KIDNEY DISEASE

CROSS-REFERENCE TO RELATED APPLICATIONS

This application is the U.S. National Stage filing under 35 U.S.C. §371 of International Application No. PCT/US2011/032924, filed Apr. 18, 2011, which claims benefit of U.S. Provisional Application No. 61/325,343, filed Apr. 18, 2010.

FIELD OF THE INVENTION

This disclosure relates to the field of individualized medicine, particularly to the determination of risk of a subject to develop renal disease, such as focal segmental glomerulosclerosis (FSGS) or end-stage kidney disease (ESKD). The disclosure also relates to the determination of resistance to disease associated with *Trypanosoma* infection and methods for treating *Trypanosoma* infection in a subject.

BACKGROUND OF THE INVENTION

The prevalence of chronic kidney disease (CKD) in the United States is now estimated at 13%, and is associated with significant morbidity and mortality (Coresh et al., *Am J Kidney Dis* 2003; 41(1):1-12). In particular, approximately 100,000 Americans develop end-stage kidney disease (ESKD) each year. The cumulative life-time risk for ESKD varies by race, and is approximately 7.5% for African-Americans and 2.1% for European Americans (Kiberd et al., *J Am Soc Nephrol* 2002; 13(6):1635-44). In particular, African-Americans have a disproportionate risk for several forms of CKD, among them diabetic nephropathy (Cowie et al., *N Engl J Med* 1989; 321(16):1074-9), hypertensive nephrosclerosis (Toto, *Kidney Int Suppl* 2004(92):S102-4), lupus nephritis (Fernandez et al., *Arthritis Rheum* 2007; 57(4):576-84), focal segmental glomerulosclerosis (Kitiyakara et al., *Am J Kidney Dis* 2004; 44(5):815-25) (FSGS), and HIV-associated nephropathy (a distinct form of FSGS, also termed collapsing glomerulopathy).

FSGS is a clinical syndrome involving podocyte injury and glomerular scarring, and includes genetic forms with Mendelian inheritance, reactive forms associated with other illnesses (including HIV-1 disease) or medications, and an idiopathic form, which accounts for the majority of cases (Barisoni et al., *Clin J Am Soc Nephrol* 2007; 2(3):529-42). African-Americans have a 4-fold increased risk for sporadic FSGS (Kitiyakara et al., *Semin Nephrol* 2003; 23(2):172-82) and an 18-fold to 50-fold increased risk for HIV-1-associated FSGS (Kopp et al., *Kidney Int Suppl* 2003(83):S43-9; Eggers et al., *J Am Soc Nephrol* 2004; 15(9):2477-85). Individuals of African ancestry also have increased risk for FSGS in other geographic regions, suggesting that genetic factors contribute to these disparities (Kitiyakara et al., *Semin Nephrol* 2003; 23(2):172-82).

SUMMARY OF THE INVENTION

A first aspect of the invention features methods for detecting a genetic predisposition to, or an increased risk of, the development of a renal disease, such as focal segmental glomerulosclerosis (FSGS) or hypertensive end-stage kidney disease (ESKD), or both in a human subject. In one embodiment, the human subject is of African (e.g., an African American) or Hispanic ancestry (in preferred embodiments, the subject of Hispanic ancestry also is of African ancestry). In another embodiment, the human subject is of European ancestry. The methods include detecting the presence of at least one APOL1 gene risk allele (e.g., 2, 3 or 4 risk alleles; e.g., the risk allele is at least one single nucleotide polymorphism (SNP) in an APOL1 gene, such as the C-terminal exon of an APOL1 gene, or an inversion in an APOL1 gene (e.g., an inversion in a 5' region of an APOL1 gene, e.g., an inversion in which the 5' region of an APOL1 gene is replaced with a 5' region of an APOL4 gene). In other embodiments, the risk allele is a G1, G2, del6, and/or a G3 allele. The presence of the at least one SNP and/or the at least one inversion determines the genetic predisposition to renal disease, such as focal segmental glomerulosclerosis or hypertensive ESKD, or both. In other embodiments, the inversion in the APOL1 gene replaces all or a portion of up to three exons in APOL1 by sequence from APOL4 (e.g., the inversion may result in replacement of all or a portion of only the first exon, and/or all or a portion of the first and/or second exon, and/or all or a portion of the first, second, and/or all or a portion of the third exon of the APOL1 gene). These three exons may cover a range of 2000-2500 base pairs of genomic DNA (e.g., in a range of from about 100 base pairs to about 3000 base pairs of genomic DNA, such as a range from 1000 base pairs to about 2500 base pairs of genomic DNA), and may encode a maximum of about 420 base pairs of transcript (e.g., a range of from about 20 base pairs to about 500 base pairs of transcript, such as from about 100 base pairs to about 420 base pairs of transcript DNA). The actual coding sequence replaced in the APOL1 protein may only code for about 1 to about 30 amino acids, e.g., about 10 to about 20 amino acids, e.g., about 14 amino acids from APOL4. The substituted amino acids in the APOL1 protein may all appear in the preprotein portion of the hybrid APOL4/APOL1 protein and all or a portion of the replaced amino acids may be cleaved depending upon the extent and actual sequence of the inversion. In an embodiment, the inversion occurs in a coding and/or non-coding region of the APOL1 gene and/or results in a functional gene product.

In other embodiments, the method includes taking a sample from the human subject to be tested. In still other embodiments, the at least one SNP is a G at rs73885319; a G at rs60910145; a 6 base pair deletion at rs71785313; and/or a combination thereof. The at least one SNP may produce an APOL1 polypeptide having a serine to glycine mutation at position 342 (S342G), an isoleucine to methionine mutation at position 384 (I384M), a deletion of amino acids N388 and Y389, and/or a combination thereof (e.g., the at least one SNP produces an APOL1 polypeptide having a S342G and an I384M mutation). In yet other embodiments, the method includes determining the presence of the at least one SNP and/or the at least one inversion on both chromosomes of the subject. In another embodiment, the subject is infected with human immunodeficiency virus (HIV) and is at a greater risk of developing FSGS. In still other embodiments, the subject is homozygous or heterozygous for the at least one SNP and/or the inversion. In an embodiment, a determination that the human subject is homozygous for the at least one SNP and/or the at least one inversion indicates an increased likelihood the human subject will develop renal disease relative to a human subject that is heterozygous for the at least one SNP and/or the at least one inversion.

In another embodiment, the presence of the at least one SNP and/or the at least one inversion indicates the human subject has an increased risk of renal disease following treatment with a therapeutic. For example, a subject having one or more APOL1 gene risk alleles may need to be offered a treatment regimen with respect to blood pressure medications, steroids, and/or immunosuppressive agents that is different from a subject lacking any (or only having, e.g., one) APOL1 gene risk allele. In particular, subjects having one or more APOL1 gene risk alleles are more susceptible to renal damage and/or disease and the risk of kidney damage increases in patients having one or more APOL1 gene risk alleles that are treated with blood pressure medications, steroids, and/or immunosuppressive agents. Thus, in patients having one or more APOL1 gene risk alleles, the concentration of a given blood pressure medication, steroid, and/or immunosuppressive agent and/or the length of treatment may need to be decreased relative to a patient lacking any (or having only one) APOL1 gene risk alleles. Examples of therapeutics include blood pressure medications (e.g., a diuretic (e.g., chlorthalidone, chlorothiazide, furosemide, hydrochlorothiazide, indapamide, metolazone, amiloride hydrochloride, spironolactone, triamterene, bumetanide, or a combination thereof), an alpha adrenergic antagonist (e.g., alfuzosin, doxazosin, prazosin, terazosin, or tamsulosin, or a combination thereof), a central adrenergic inhibitor (e.g., clonidine, guanfacine, or methyldopa, or a combination thereof), an angiotensin converting enzyme (ACE) inhibitor (e.g., benazepril, captopril, enalapril, fosinopril, lisinopril, moexipril, perindopril, quinapril, ramipril, or trandolapril, or combinations thereof), an angiotensin II receptor blocker (e.g., candesartan, eprosartan, irbesartan, losartan, olmesartan, telmisartan, or valsartan, or combinations thereof), an alpha blocker (e.g., doxazosin, prazosin, or terazosin, or a combination thereof), a beta blocker (e.g., acebutolol, atenolol, betaxolol, bisoprolol, carteolol, metoprolol, nadolol, nebivolol, penbutolol, pindolol, propranolol, solotol, or timolol, or a combination thereof), a calcium channel blocker (e.g., amlodipine, bepridil, diltiazem, felodipine, isradipine, nicardipine, nifedipine, nisoldipine, or verapamil, or combination thereof), a vasodilator (e.g., hydralazine or minoxidil, or combination thereof), and a renin inhibitor (e.g., aliskiren), or combinations thereof), a steroid (e.g., a corticosteroid, such as cortisone, prednisone, methylprednisolone, or prednisolone), or an anabolic steroid (anatrofin, anaxvar, annadrol, bolasterone, decadiabolin, decadurabolin, dehydropiandrosterone (DHEA), delatestryl, dianiabol, dihydrolone, durabolin, dymethazine, enoltestovis, equipose, gamma hydroxybutyrate, maxibolin, methatriol, methyltestosterone, parabolin, primobolin, quinolone, therabolin, trophobolene, and winstrol), or an immunosuppressive agent, such as a glucocorticoid, a cytostatic, an antibody, or an anti-immunophilin and/or mychophenolate mofetil (MMF), FK-506, azathioprine, cyclophosphamide, methotrexate, dactinomycin, antithymocyte globulin (AT-GAM), an anti-CD20-antibody, a muromonoab-CD3 antibody, basilizimab, daclizumab, cyclosporin, tacrolimus, voclosporin, sirolimus, an interferon, infliximab, etanercept, adalimumab, fingolimod, and/or myriocin).

In other embodiments, the presence of the at least one SNP and/or the at least one inversion indicates the human subject has an increased risk of kidney failure (and may have a greater need for a kidney transplant) relative to a human subject lacking the at least one SNP and/or the at least one inversion.

A second aspect of the invention features a method of evaluating a human subject (e.g., a potential kidney donor) for their suitability as a transplant donor by determining the presence of at least one human APOL1 gene risk allele (e.g., at least one (e.g., two, three, or four) single nucleotide polymorphism (SNP; e.g., a G at rs73885319 (G1), a G at rs60910145 (G2), a 6 base pair deletion at rs71785313 (del6), and/or a combination thereof) and/or at least one inversion in a human APOL1 gene) in a cell, tissue, or organ of the human subject, in which the presence of the at least one APOL1 gene risk allele indicates the human subject is not suitable as a transplant donor. In other embodiments, the at least one SNP produces an APOL1 polypeptide having a serine to glycine mutation at position 342 (S342G), an isoleucine to methionine mutation at position 384 (I384M), a deletion of amino acids N388 and Y389, and/or a combination thereof (e.g., the at least one SNP produces an APOL1 polypeptide having a S342G and an I384M mutation). In other embodiments, the inversion is, e.g., a substitution of the 5' region of the APOL1 gene with the 5' region of another apolipoprotein gene (e.g., an APOL4 gene)). In yet other embodiments, the method includes determining the presence of the at least one SNP and/or the at least one inversion on both chromosomes of the subject. The human subject may be of African or Hispanic ancestry (e.g., an African American subject). In other embodiments, the method includes detecting the presence of the at least one SNP and the at least one inversion in said APOL1 gene; the inversion includes recombination between the human APOL1 gene and another apolipoprotein gene (e.g., a human APOL4 gene); the inversion occurs in a coding and/or non-coding region of the APOL1 gene; and/or the inversion results in a functional gene product. In still other embodiments, detection of at least two SNPs in the human subject further indicates the human subject is not suitable as a transplant donor. The method may further include determining whether the human subject is homozygous or heterozygous for the at least one SNP and/or the at least one inversion (e.g., a determination that the human subject is homozygous for the at least one SNP and/or the at least one inversion indicates an increased likelihood the human subject will develop renal disease relative to a human subject that is heterozygous for the at least one SNP and/or the at least one inversion).

A third aspect of the invention features methods for detecting a disease associated with *Trypanosoma* spp. infection, such as a disease associated with *T. brucei* infection, such as African trypanosomiasis (sleeping sickness) in a subject (e.g., a human subject) by detecting a resistance allele of an APOL1 gene. In an embodiment, the resistance allele includes at least one (e.g., two, three, or four) SNP in an APOL1 gene, such as the C-terminal exon of an APOL1 gene, and/or at least one inversion in an APOL1 gene (e.g., an inversion in a 5' region of an APOL1 gene, e.g., an inversion in which the 5' region of an APOL1 gene is replaced with a 5' region of an APOL4 gene). In other embodiments, the resistance allele is a G1, G2, del6, and/or a G3 allele. The presence of the SNP and/or the inversion determines resistance of the subject to disease associated with *Trypanosoma* spp. infection.

A fourth aspect of the invention features methods for treating a subject infected with *T. brucei* (such as *T. brucei brucei*, *T. b. rhodesiense*, or *T. b. gambiense*). The methods include administering a therapeutically effective amount of an APOL1 protein (e.g., a human APOL1 protein) that includes at least one resistance allele (e.g., a S342G substitution, an I384M substitution, a deletion of N388 and Y389 and/or an inversion to the subject. In some examples, the APOL1 protein is included in human serum administered to the subject. In other examples, the APOL1 protein is recombinant.

The foregoing and other features of the disclosure will become more apparent from the following detailed description, which proceeds with reference to the accompanying figures.

BRIEF DESCRIPTION OF THE DRAWINGS

FIG. 3 is a pair of maps showing average annual rate of new cases of (A) *Trypanosoma brucei rhodesiense* and (B) *Trypanosoma brucei gambiense* sleeping sickness reported between 1997 and 2006 in Africa.

FIG. 6A shows the mean age at dialysis initiation by G1 risk allele status in subjects with hypertension attributed ESRD (H-ESKD).
FIG. 6B shows age by G1 risk allele status in subjects with other ESRD causes, including HIV, inflammation, toxins, etc. Horizontal bars denote mean age while vertical bars denote standard error.
*significantly different from wild type (Wt+Wt)

FIG. 10 shows the genomic sequence of APOL1 and APOL4 following G3 inversion (SEQ ID NO: 7).

SEQUENCE LISTING

Figure 1A:
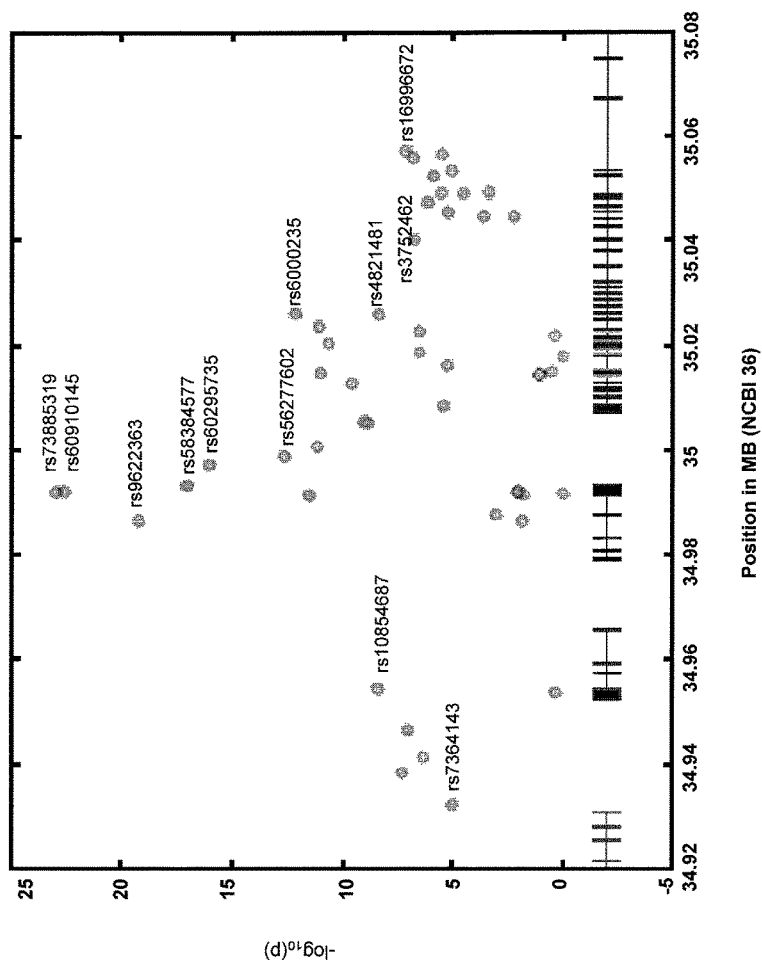
FIG. 1 is a pair of plots showing logistic regression adjusting for APOL1 alleles G1 and G2. Results of association between 205 idiopathic biopsy-proven African-American FSGS cases and 180 African-American controls. On the x-axis and y-axis, genomic position and −log 10 of the p-values are shown. Highlighted are also SNPs rs4821481 and rs3752462 whose combined risk alleles define the E-1 haplotype (Kopp et al., Nature Genet. 40:1175-1184, 2008). (A) Association of the studied variants with FSGS using Fisher's exact test. (B) Association of the studied variants with FSGS after adjusting for allele G1 using logistic regression.

The nucleic acid sequences and amino acid sequences listed are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. It should be noted that single nucleotide polypmorphisms are identified in the leading strand, wherein the risk nucleotide is listed first, and the protective nucleotide is listed second. Due to the complementary nature of DNA, the single nucleotide polymorphism is present in both DNA strands, and thus can also be identified in the lagging strand.

SEQ ID NOs: 1-3 are nucleic acid sequences from the APOL1 gene, each include a single nucleotide polymorphism of interest.

SEQ ID NOs: 4 and 5 are exemplary nucleic acid and amino acid sequences of a human apolipoprotein L1, respectively.

SEQ ID NO: 7 is a genomic sequence of an APOL1 and APOL4 inversion.

DETAILED DESCRIPTION

I. Abbreviations and Terms

APOL1: apolipoprotein L I gene or protein
ESKD: end-stage kidney disease
FSGS: focal segmental glomerulosclerosis
HIV: human immunodeficiency virus
LD: linkage disequilibrium
LOD: logarithm of the odds
MALD: mapping by admixture linkage disequilibrium
NHS: normal human serum
OR: odds ratio
ROC: receiver operator characteristic
SNP: single nucleotide polymorphism
SRA: serum resistance-associated gene or protein Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Administration:

To provide or give a subject an agent by any effective route. Exemplary routes of administration include, but are not limited to, oral, injection (such as subcutaneous, intramuscular, intradermal, intraperitoneal, and intravenous), sublingual, rectal, transdermal, intranasal, vaginal and inhalation routes. Administration of extracorporeal treatment (e.g., dialysis) is also included.

African Ancestry:

An individual whose ancestors are from Sub-Saharan Africa prior to the era of European expansion (prior to about 1500). There are a number of programs that can be used to analyze DNA to determine if an individual is of African ancestry, such as STRUCTURE™ (available on the internet at pritch.bsd.uchicago.edu/structure.html). In one example, African-American individuals are those individuals who reside in the United States and self-identify themselves as being of African origin. In another example, African-Americans are individuals who reside in the United States and self-identify as being of African origin, and are of African ancestry as determined by a program that analyzes DNA ancestry, such as STRUCTURE™.

Allele:

A particular form of a genetic locus, distinguished from other forms by its particular nucleotide sequence, or one of the alternative polymorphisms found at a polymorphic site.

Allele Frequency:

A measure of the relative frequency of an allele at a genetic locus in a population. Usually allele frequency is expressed as a proportion or a percentage. In population genetics, allele frequencies are used to depict the amount of genetic diversity at the individual, population, or species level. There are various databases in the public domain that contain SNPs and a user may for example, determine the relative allele frequency in some instances using such publicly available databases.

In the instant application the allele frequency for a risk allele is greater than 5% in subjects of African ancestry. In a further embodiment, the allele frequency for a risk allele is greater than at least 10%, at least 15%, at least 20%, at least 25%, at least 30%, at least 35%, at least 40%, at least 45%, or at least 50% in subjects of African ancestry. In some embodiments, an unaffected population is used to calculate allele frequency. Risk is elevated in individuals that carry the risk allele.

There are a number of diseases or disorders that are associated with the identification of one or more SNPs or risk alleles. In many cases, the diseases or disorders are autosomal dominant mutations and any associated SNPs are observed only in individuals who present with clinical manifestations of the disease. In other circumstances, the occurrence of a disease-associated SNP is so rare that no-known frequency can be determined (for example, through the use of public domain SNP databases or by comparison with the literature) and these diseases/disorders are correctly defined as having an allele frequency significantly lower than 1%.

Amplification:

To increase the number of copies of a nucleic acid molecule. The resulting amplification products are called "amplicons." Amplification of a nucleic acid molecule (such as a DNA or RNA molecule) refers to use of a technique that increases the number of copies of a nucleic acid molecule in a sample. An example of amplification is the polymerase chain reaction (PCR), in which a sample is contacted with a pair of oligonucleotide primers under conditions that allow for the hybridization of the primers to a nucleic acid template in the sample. The primers are extended under suitable conditions, dissociated from the template, re-annealed, extended, and dissociated to amplify the number of copies of the nucleic acid. This cycle can be repeated. The product of amplification can be characterized by such techniques as electrophoresis, restriction endonuclease cleavage patterns, oligonucleotide hybridization or ligation, and/or nucleic acid sequencing.

Other examples of in vitro amplification techniques include quantitative real-time PCR; reverse transcriptase PCR (RT-PCR); real-time PCR (rt PCR); real-time reverse transcriptase PCR (rt RT-PCR); nested PCR; strand displacement amplification (see U.S. Pat. No. 5,744,311); transcription-free isothermal amplification (see U.S. Pat. No. 6,033,881); repair chain reaction amplification (see PCT Publication No. WO 90/01069); ligase chain reaction amplification (see European patent publication No. EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134), amongst others.

APOL1:

A gene encoding human apolipoprotein L, 1 (OMIM: 603743). This gene encodes a secreted high density lipoprotein which binds to apolipoprotein A-I. Apolipoprotein A-I is a relatively abundant plasma protein and is the major apoprotein of HDL. Several different transcript variants encoding different isoforms have been found for this gene.

Exemplary SNPs observed in APOL1 that are associated with a predisposition to renal disease include a G at rs73885319 ("G1"); a G at rs60910145 ("G2"); or a 6 base pair deletion at rs71785313 ("del6") (incorporated by reference as present in dbSNP (ncbi.nlm.nih.gov/SNP) on Apr. 18, 2010), as well as combinations thereof.

Nucleic acid and protein sequences for human APOL1 are publicly available. For example, GENBANK® Accession No. NC_000022.10 (nucleotides 36649117.36663577) discloses an exemplary human APOL1 genomic sequence (incorporated by reference as provided by GENBANK® on Apr. 18, 2010). In other examples, GENBANK® Accession Nos. AF305224.1, NM_003661.3, NM_145343.2, NM_001136540.1, z82215, and BC127186.1 disclose exemplary human APOL1 nucleic acid sequences, and GENBANK® Accession Nos. CAQ09089, NP_003652, AAI43039.1, and AAI42721.1 disclose exemplary human APOL1 protein sequences, all of which are incorporated by reference as provided by GENBANK® on Apr. 18, 2010.

Caucasian:

A human racial classification traditionally distinguished by physical characteristics such as very light to brown skin pigmentation and straight to wavy or curly hair, which includes persons having origins in any of the original peoples of Europe, North Africa, or the Middle East. Popularly, the word "white" is used synonymously with "Caucasian" in North America. Such persons retain substantial genetic similarity to natives or inhabitants of Europe, North Africa, or the Middle East. In a particular example, a Caucasian is at least 1/64 Caucasian.

Concordance:

The presence of two or more loci or traits (or combination thereof) derived from the same parental chromosome. The opposite of concordance is discordance, that is, the inheritance of only one (of two or more) parental alleles and/or traits associated with a parental chromosome.

Correlation:

A correlation between a phenotypic trait and the presence or absence of a genetic marker (or haplotype or genotype) can be observed by measuring the phenotypic trait and comparing it to data showing the presence or absence of one or more genetic markers. Some correlations are stronger than others, meaning that in some instances subjects with FSGS will display a particular genetic marker (e.g., 100% correlation). In other examples the correlation will not be as strong, meaning that a subject with FSGS will only display a particular genetic marker 90%, 85%, 70%, 60%, 55%, or 50% of the time. In some instances, a haplotype which contains information relating to the presence or absence of multiple markers can also be correlated to a genetic predisposition such as the development of FSGS, or the type of onset. Correlations can be described using various statistical analyses known to the skilled artisan.

Decrease:

Becoming less or smaller, as in number, amount, size, or intensity. In one example, decreasing the risk of a disease (such as FSGS or hypertensive ESKD) includes a decrease in the likelihood of developing the disease by at least about 20%, for example by at least about 30%, 40%, 50%, 60%, 70%, 80%, or 90%. In another example, decreasing the risk of a disease includes a delay in the development of the disease, for example a delay of at least about six months, such as about one year, such as about two years, about five years, or about ten years.

In one example, decreasing the signs and symptoms of FSGS includes decreasing the effects of the disease such as podocyte injury or glomerular scarring by a desired amount, for example by at least 5%, at least 10%, at least 15%, at least 20%, at least 25%, at least 30%, at least 50%, at least 75%, or even at least 90%, as compared to a response in the absence of a therapeutic composition.

In another, decreasing the signs and symptoms of *Trypanosoma* infection, such as sleeping sickness, includes decreasing the effects of the disease such as fever, headache, joint pain, lymph node swelling, anemia, confusion, reduced coordination, or disruption of the sleep cycle by a desired amount, for example by at least 5%, at least 10%, at least 15%, at least 20%, at least 25%, at least 30%, at least 50%, at least 75%, or even at least 90%, as compared to a response in the absence of a therapeutic composition.

DNA (Deoxyribonucleic Acid):

DNA is a long chain polymer which comprises the genetic material of most living organisms (some viruses have genes comprising ribonucleic acid (RNA)). The repeating units in DNA polymers are four different nucleotides, each of which comprises one of the four bases, adenine, guanine, cytosine and thymine bound to a deoxyribose sugar to which a phosphate group is attached. Triplets of nucleotides (referred to as codons) code for each amino acid in a polypeptide, or for a stop signal (termination codon). The term codon is also used for the corresponding (and complementary) sequences of three nucleotides in the mRNA into which the DNA sequence is transcribed.

Unless otherwise specified, any reference to a DNA molecule is intended to include the reverse complement of that DNA molecule. Except where single-strandedness is required by the text herein, DNA molecules, though written to depict only a single strand, encompass both strands of a double-stranded DNA molecule. Thus, a reference to the nucleic acid molecule that encodes a protein, or a fragment thereof, encompasses both the sense strand and its reverse complement. Thus, for instance, it is appropriate to generate probes or primers from the reverse complement sequence of the disclosed nucleic acid molecules.

Dominant Model:

A genetic based model that tests the association of having at least one risk allele (e.g. Dd or DD) versus not having a risk allele at all (dd).

End-Stage Kidney Disease (ESKD) or End-Stage Renal Disease (ESRD):

A stage of kidney impairment that is irreversible and cannot be controlled by conservative management alone. ESKD requires dialysis or kidney transplantation to maintain life.

European Ancestry:

A type of ancestry shared by people who derived from the fertile crescent of the Middle East some 50,000 years ago and spread to occupy Europe, the Middle East, parts of Eurasia and South Asia. There are a number of programs that can be used to analyze DNA to determine if an individual is of African ancestry, such as STRUCTURE™ (available on the internet at pritch.bsd.uchicago.edu/structure.html) and EURODNA™ and ANCESTRYBYDNA™ (available through the DNA print website). In one example, European-American individuals are those individuals who reside in the United States and self-identify themselves as being of European origin. In another example, European-Americans are individuals who reside in the United States and self-identify as being of European origin, and are of European ancestry as determined by a program that analyzes DNA ancestry.

Focal Segmental Glomerulosclerosis (FSGS):

A clinical syndrome involving podocyte injury and glomerular scarring, and includes genetic forms with Mendelian inheritance, reactive forms associated with other illnesses (including HIV-1 disease) or medications, and an idiopathic form, which accounts for the majority of cases. The name refers to the appearance of the kidney tissue on biopsy: focal—only some of the glomeruli are involved; segmental—only part of an entire glomerulus is involved; glomerulosclerosis—scarring of the glomerulus. FSGS presents as a nephrotic syndrome (which is characterized by edema (associated with weight gain), hypoalbuminemia (low serum albumin (a protein) in the blood), hyperlipidemia and hypertension (high blood pressure)). In adults it may also present as kidney failure and proteinuria, without a full-blown nephrotic syndrome.

There are five mutually exclusive variants of FSGS that can be distinguished by the pathologic findings seen on renal biopsy: collapsing variant, glomerular tip lesion variant, cellular variant, perihilar variant, and not otherwise specified (NOS) variant. Determining the type of variant can have prognostic value in individuals with primary FSGS (where no underlying cause is determined). The collapsing variant is associated with higher rate of progression to end-stage renal disease, whereas glomerular tip lesion variant has low rate of progression to end-stage renal disease in most patients. The cellular variant shows a similar clinical presentation to collapsing and glomerular tip variant but has intermediate outcomes between these two variants.

Genetic Predisposition:

Susceptibility of a subject to a disease, such as renal disease, including FSGS and hypertensive end stage renal disease. Detecting a genetic predisposition can include, but does not necessarily include, detecting the presence of the disease itself, such as but not limited to an early stage of the disease process. Detecting a genetic predisposition also includes detecting the risk of developing the disease, and determining the susceptibility of that subject to developing the disease or to having a poor prognosis for the disease. Thus, if a subject has a genetic predisposition to a disease they do not necessarily develop the disease but are at risk for developing the disease.

Genomic Target Sequence:

A sequence of nucleotides located in a particular region in the human genome that corresponds to one or more specific genetic abnormalities, such as a nucleotide polymorphism, a deletion, an insertion, or amplification. The target can be for instance a coding sequence; it can also be the non-coding strand that corresponds to a coding sequence. The target can also be a non-coding sequence, such as an intronic sequence. In some examples, genomic target sequences are genomic sequences of genes that encode apolipoprotein L1(APOL1).

Gene:

A segment of DNA that contains the coding sequence for a protein, wherein the segment may include promoters, exons, introns, and other untranslated regions that control expression.

Genotype:

An unphased 5' to 3' sequence of nucleotide pair(s) found at a set of one or more polymorphic sites in a locus on a pair of homologous chromosomes in an individual. "Genotyping" is a process for determining a genotype of an individual.

Haplotype:

A 5' to 3' sequence of nucleotides found at a set of one or more polymorphic sites in a locus on a single chromosome from a single individual. "Haplotype pair" is the two haplotypes found for a locus in a single individual. With regard to a population, haplotypes are the ordered, linear combination of polymorphisms (e.g., single nucleotide polymorphisms (SNPs)) in the sequence of each form of a gene (on individual chromosomes) that exist in the population. "Haplotyping" is a process for determining one or more haplotypes in an individual and includes use of family pedigrees, molecular techniques and/or statistical inference. "Haplotype data" is the information concerning one or more of the following for a specific gene: a listing of the haplotype pairs in an individual or in each individual in a population; a listing of the different haplotypes in a population; frequency of each haplotype in that or other populations, and any known associations between one or more haplotypes and a trait.

Haplotype Block:

Sites of closely located SNPs which are inherited in blocks. A haplotype block includes a group of SNP locations that do not appear to recombine independently and that can be grouped together. Regions corresponding to blocks have a few common haplotypes which account for a large proportion of chromosomes. Identification of haplotype blocks is a way of examining the extent of linkage disequilibrium (LD) in the genome. The "Hap-Map" project (see the internet at the Hap-Map website) describes the mapping of haplotype blocks in the human genome.

There are programs available on the internet for the identification of haplotype blocks, such as the program HAPBLOCK™ which runs on both PC and Unix and is available from the University of Southern California website on the internet. A further program, which in addition to block identification also has visualization and selection of "tagging" SNPs is HAPLOBLOCKFINDER™, which runs interactively on the web or can be downloaded for local machine use (Unix or PC). It can be accessed at the program website available on the internet.

Hispanic Ancestry:

A person of Mexican, Puerto Rican, Cuban, Dominican, South or Central American, or other Spanish or Portuguese culture or origin, regardless of race.

Hybridization:

Oligonucleotides and their analogs hybridize by hydrogen bonding, which includes Watson-Crick, Hoogsteen or reversed Hoogsteen hydrogen bonding, between complementary bases. Generally, nucleic acids consist of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence. For example, an oligonucleotide can be complementary to a specific genetic locus, so it specifically hybridizes with a mutant allele (and not the reference allele) or so that it specifically hybridizes with a reference allele (and not the mutant allele).

"Specifically hybridizable" and "specifically complementary" are terms that indicate a sufficient degree of complementarity such that stable and specific binding occurs between the oligonucleotide (or its analog) and the DNA or RNA target. The oligonucleotide or oligonucleotide analog need not be 100% complementary to its target sequence to be specifically hybridizable. An oligonucleotide or analog is specifically hybridizable when binding of the oligonucleotide or analog to the target DNA or RNA molecule interferes with the normal function of the target DNA or RNA, and there is a sufficient degree of complementarity to avoid non-specific binding of the oligonucleotide or analog to non-target sequences under conditions where specific binding is desired, for example under physiological conditions in the case of in vivo assays or systems. Such binding is referred to as specific hybridization. In one example, an oligonucleotide is specifically hybridizable to DNA or RNA nucleic acid sequences including an allele of a gene, wherein it will not hybridize to nucleic acid sequences containing a polymorphism.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the Na$^+$ concentration) of the hybridization buffer will determine the stringency of hybridization, though wash times also influence stringency. Calculations regarding hybridization conditions required for attaining particular degrees of stringency are discussed by Sambrook et al. (ed.), *Molecular Cloning: A Laboratory Manual,* 2nd ed., vol. 1-3, Cold Spring Harbor Laboratory Press, Cold Spring Harbor, N.Y., 1989, chapters 9 and 11.

The following is an exemplary set of hybridization conditions and is not limiting:

Very High Stringency (Detects Sequences that Share at Least 90% Identity)

Hybridization: 5×SSC at 65° C. for 16 hours

Wash twice: 2×SSC at room temperature (RT) for 15 minutes each

Wash twice: 0.5×SSC at 65° C. for 20 minutes each

High Stringency (Detects Sequences that Share at Least 80% Identity)

Hybridization: 5×-6×SSC at 65° C.-70° C. for 16-20 hours

Wash twice: 2×SSC at RT for 5-20 minutes each

Wash twice: 1×SSC at 55° C.-70° C. for 30 minutes each

Low Stringency (Detects Sequences that Share at Least 50% Identity)

Hybridization: 6×SSC at RT to 55° C. for 16-20 hours

Wash at least twice: 2×-3×SSC at RT to 55° C. for 20-30 minutes each.

Hypertension:

High blood pressure; transitory or sustained elevation of systemic arterial blood pressure to a level likely to induce cardiovascular damage or other adverse consequences. Hypertension has been arbitrarily defined as a systolic blood pressure above 140 mm Hg or a diastolic blood pressure above 90 mm Hg. Consequences of uncontrolled hypertension include retinal vascular damage (Keith-Wagener-Barker changes), cerebrovascular disease and stroke, left ventricular hypertrophy and failure, myocardial infarction, dissecting aneurysm, and renovascular disease. An underlying disorder (such as renal disease, Cushing syndrome, pheochromocytoma) is identified in fewer than 10% of all cases of hypertension. The remainder, traditionally labeled "essential" hypertension, probably arise from a variety of disturbances in normal pressure-regulating mechanisms (which involve baroreceptors, autonomic influences on the rate and force of cardiac contraction and vascular tone, renal retention of salt and water, formation of angiotensin II under the influence of renin and angiotensin-converting enzyme, and other factors known and unknown), and most are probably genetically conditioned.

Hypertensive Nephropathy (or "hypertensive nephrosclerosis," or "hypertensive renal disease" or "hypertensive kidney disease"): A medical condition referring to damage to the kidney due to chronic high blood pressure. In the kidneys, as a result of benign arterial hypertension, hyaline (pink, amorphous, homogeneous material) accumulates in the wall of small arteries and arterioles, producing the thickening of their walls and the narrowing of the lumens—hyaline arteriolosclerosis. Consequent ischemia produces tubular atrophy, interstitial fibrosis, glomerular alterations (smaller glomeruli with different degrees of hyalinization—from mild to sclerosis of glomeruli) and periglomerular fibrosis. In advanced stages ("end-stage"), renal failure will occur.

Isolated:

An "isolated" biological component (such as a nucleic acid molecule, protein or organelle) has been substantially separated or purified away from other biological components in the cell of the organism in which the component naturally occurs, e.g., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Linkage:

The association of two or more loci at positions on the same chromosome, such that recombination between the two loci is reduced to a proportion significantly less than 50%. The term linkage can also be used in reference to the association between one or more loci and a trait if an allele (or alleles) and the trait, or absence thereof, are observed together in significantly greater than 50% of occurrences. A linkage group is a set of loci, in which all members are linked either directly or indirectly to all other members of the set Linkage Disequilibrium:

Co-occurrence of two genetic loci (e.g., markers) at a frequency greater than expected for independent loci based on the allele frequencies. Linkage disequilibrium (LD) typically occurs when two loci are located close together on the same chromosome. When alleles of two genetic loci (such as a marker locus and a causal locus) are in strong LD, the allele observed at one locus (such as a marker locus) is predictive of the allele found at the other locus (for example, a causal locus contributing to a phenotypic trait). The linkage disequilibrium (LD) measure $r^2$ (the squared correlation coefficient) can be used to evaluate how SNPs are related on a haplotype block. For each tag SNP, the $r^2$ between that tag SNP and each additional SNP in a genotyping set can be calculated. The highest of these values is the maximum $r^2$ value, m. In several embodiments, a haplotype block can be identified by SNPs that have an $r^2$ value of greater than or equal to 0.75, greater than or equal to 0.8, greater than or equal to about 0.85, greater than or equal to 0.9, or greater than or equal to 0.95 from the tag SNP. A low $r^2$ value such as less than or equal to 0.3, less than or equal to 0.2, less than or equal to 0.1, is generally considered to be less predictive than a higher $r^2$ value, which is considered a stronger predictor of linkage disequilibrium, such as greater than or equal to 0.75.

Locus:

A location on a chromosome or DNA molecule corresponding to a gene or a physical or phenotypic feature, where physical features include polymorphic sites.

Mutation:

Any change of a nucleic acid sequence as a source of genetic variation. For example, mutations can occur within a gene or chromosome, including specific changes in non-coding regions of a chromosome, for instance changes in or near regulatory regions of genes. Types of mutations include, but are not limited to, base substitution point mutations (which are either transitions or transversions), deletions, and insertions. Missense mutations are those that introduce a different amino acid into the sequence of the encoded protein; nonsense mutations are those that introduce a new stop codon; and silent mutations are those that introduce the same amino acid often with a base change in the third position of the codon. In the case of insertions or deletions, mutations can be in-frame (not changing the frame of the overall sequence) or frame shift mutations, which may result in the misreading of a large number of codons (and often leads to abnormal termination of the encoded product due to the presence of a stop codon in the alternative frame).

Non-Coding:

A change in nucleotide sequence that does not result in the production of a codon that encodes for an amino acid other than the wild-type human sequence, and therefore does not result in the production of any alteration in polypeptide sequence. In the instant application, the term "non-coding" refers to the exclusion of non-synonymous SNPs or haplotypes. In addition, the term "non-coding" also excludes promoter regions of a gene and is therefore limited to intronic and exonic domains of the gene.

Odds Ratio:

A calculation performed by analysis of a two by two contingency table. In one example, the first column provides a risk indicator in the absence of a disease (e.g., FSGS). The second column provides the same risk indicator in the presence of the same disease. The first row lists the risk indicator in the absence of a risk factor (such as race) and the second row lists the same risk indicator in the presence of the same risk factor (e.g., race). The Odds Ratio (OR) is determined as the product of the two diagonal entries in the contingency table divided by the product of the two off-diagonal entries of the contingency table. An OR of 1 is indicative of no association. Accordingly, very large or very small ORs are indicative of a strong association between the factors under investigation. The OR is independent of the ratio of cases or controls in a study, group or subset.

Oligonucleotide:

An oligonucleotide is a plurality of joined nucleotides joined by native phosphodiester bonds, between about 6 and about 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucicotide. Functional analogs of naturally occurring polynucleotides can bind to RNA or DNA, and include peptide nucleic acid (PNA) molecules.

In several examples, oligonucleotides and oligonucleotide analogs can include linear sequences up to about 200 nucleotides in length, for example a sequence (such as DNA or RNA) that is at least 6 bases, for example at least 8, 10, 15, 20, 25, 30, 35, 40, 45, 50, 100, or even 200 bases long, or from about 6 to about 70 bases, for example about 10-25 bases, such as 12, 15, or 20 bases.

Phased:

As applied to a sequence of nucleotide pairs for two or more polymorphic sites in a locus, phased means the combination of nucleotides present at those polymorphic sites on a copy of the DNA for the locus.

Polymorphism:

A variation in a gene sequence. The polymorphisms can be those variations (DNA sequence differences) which are generally found between individuals or different ethnic groups and geographic locations which, while having a different sequence, produce functionally equivalent gene products. Typically, the term can also refer to variants in the sequence which can lead to gene products that are not functionally equivalent. Polymorphisms also encompass variations which can be classified as alleles and/or mutations which can produce gene products which may have an altered function. Polymorphisms also encompass variations which can be classified as alleles and/or mutations which either produce no gene product or an inactive gene product or an active gene product produced at an abnormal rate or in an inappropriate tissue or in response to an inappropriate stimulus. Alleles are the alternate forms that occur at the polymorphism.

Polymorphisms can be referred to, for instance, by the nucleotide position at which the variation exists, by the change in amino acid sequence caused by the nucleotide variation, or by a change in some other characteristic of the nucleic acid molecule or protein that is linked to the variation.

In the instant application "polymorphism" refers a traditional definition, in that the definition "polymorphism" means that the minor allele frequency must be greater than at least 1%.

A "single nucleotide polymorphism (SNP)" is a single base (nucleotide) polymorphism in a DNA sequence among individuals in a population. Typically in the literature, a single nucleotide polymorphism (SNP) may fall within coding sequences of genes, non-coding regions of genes, or in the intergenic regions between genes. SNPs within a coding sequence will not necessarily change the amino acid sequence of the protein that is produced, due to degeneracy of the genetic code. A SNP in which both forms lead to the same polypeptide sequence is termed "synonymous" (sometimes called a silent mutation). If a different polypeptide sequence is produced they are "nonsynonymous." A non-synonymous change may either be missense or "nonsense," where a missense change results in a different amino acid, while a nonsense change results in a premature stop codon.

A tag SNP is a SNP that by itself or in combination with additional tag SNPs indicates the presence of a specific haplotype, or of one member of a group of haplotypes. The haplotype or haplotypes can indicate a genetic factor is associated with risk for disease, thus a tag SNP or combination of tag SNPs indicates the presence or absence of risk factors for disease. A "tag SNP" is a representative single nucleotide polymorphism (SNP) in a region of the genome with high linkage disequilibrium (the non-random association of alleles at two or more loci) that is associated with a disease, such as renal disease, for example FSGS or ESKD. A tag SNP can be used to identify other SNPs, such as those with a specified $r^2$ value from the tag SNP, which are associated with a disease, such as FSGS or ESKD. Statistical methods to identify a tag SNP are known (see Hoperin et al., Bioinformatics 21 (suppl): i195-i203, 2005, herein incorporated by reference).

Predictive Power:

A characteristic for a dichotomous test (one that will return either a positive or negative result), indicating increased risk with a positive result. Predictive power is measured by sensitivity and specificity. In some examples, the sensitivity of a test is the fraction of people who tested positive for the presence of at least one APOL1 risk allele who will develop renal disease, such as FSGS or hypertensive ESKD and the specificity is the fraction of people who tested negative for the presence of at least one APOL1 risk allele (e.g., absence of at least one risk allele) who will not develop renal disease. A measure of the predictive power of a test is the receiver operator characteristic (ROC) C statistic. The ROC C statistic may be defined as the probability (or fraction of the time) that an individual with the condition has a risk score larger than of an individual without the condition. For a test with no predictive power, the C statistic will be 0.5; for a dichotomous test that can invariably correctly identify positives and negatives (perfect predictive power), the C statistic will be 1.

Probes and Primers:

Isolated nucleic acids of at least ten nucleotides capable of hybridizing to a target nucleic acid. A detectable label or reporter molecule can be attached to a probe or primer. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, for example in Sambrook et al. (In *Molecular Cloning: A Laboratory Manual*, CSHL, New York, 1989) and Ausubel et al. (In *Current Protocols in Molecular Biology*, John Wiley & Sons, New York, 1998).

In a particular example, a probe or primer includes at least one fluorophore, such as an acceptor fluorophore or donor fluorophore. For example, a fluorophore can be attached at the 5'- or 3'-end of the probe/primer. In specific examples, the fluorophore is attached to the base at the 5'-end of the probe/primer, the base at its 3'-end, the phosphate group at its 5'-end or a modified base, such as a T internal to the probe/primer.

Probes are generally at least 15 nucleotides in length, such as at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50 at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, or more contiguous nucleotides complementary to the target nucleic acid molecule, such as 20-70 nucleotides, 20-60 nucleotides, 20-50 nucleotides, 20-40 nucleotides, or 20-30 nucleotides.

Primers are short nucleic acid molecules, for instance DNA oligonucleotides are 10 nucleotides or more in length, which can be annealed to a complementary target nucleic acid molecule by nucleic acid hybridization to form a hybrid between the primer and the target nucleic acid strand. A primer can be extended along the target nucleic acid molecule by a polymerase enzyme. Therefore, primers can be used to amplify a target nucleic acid molecule.

The specificity of a primer increases with its length. Thus, for example, a primer that includes 30 consecutive nucleotides will anneal to a target sequence with a higher specificity than a corresponding primer of only 15 nucleotides. Thus, to obtain greater specificity, probes and primers can be selected that include at least 15, 20, 25, 30, 35, 40, 45, 50, 55, 60, 65, 70 or more consecutive nucleotides. In particular examples, a primer is at least 15 nucleotides in length, such as at least 15 contiguous nucleotides complementary to a target nucleic acid molecule. Particular lengths of primers that can be used to practice the methods of the present disclosure include primers having at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 45, at least 50, at least 55, at least 60, at least 65, at least 70, or more contiguous nucleotides complementary to the target nucleic acid molecule to be amplified, such as a primer of 15-70 nucleotides, 15-60 nucleotides, 15-50 nucleotides, or 15-30 nucleotides.

Primer pairs can be used for amplification of a nucleic acid sequence, for example, by PCR, real-time PCR, or other nucleic-acid amplification methods known in the art. An "upstream" or "forward" primer is a primer 5' to a reference point on a nucleic acid sequence. A "downstream" or "reverse" primer is a primer 3' to a reference point on a nucleic acid sequence. In general, at least one forward and one reverse primer are included in an amplification reaction.

Nucleic acid probes and primers can be readily prepared based on the nucleic acid molecules provided herein (such as APOL1). It is also appropriate to generate probes and primers based on fragments or portions of these disclosed nucleic acid molecules, for instance regions that encompass the identified polymorphisms of interest. PCR primer pairs can be derived from a known sequence by using computer programs intended for that purpose such as Primer (Version 0.5, ©1991, Whitehead Institute for Biomedical Research, Cambridge, Mass.) or PRIMER EXPRESS®Software (Applied Biosystems, AB, Foster City, Calif.).

Recessive Model:

A genetic based model that tests the association of having two risk alleles (e.g. DD) versus having at least one non-risk allele (e.g., Dd or dd). In some examples, it is a genetic based model that tests the association of having two copies of a specified allele versus having at least one copy of the alternate (reference) allele.

Recombinant:

A nucleic acid molecule, protein, cell, or organism that results from the recombination of genes (e.g., a sequence that is not naturally occurring or a sequence that is made by an artificial combination of two otherwise separated segments of sequence), regardless of whether naturally or artificially induced. This artificial combination can be accomplished by chemical synthesis or by the artificial manipulation of isolated segments of nucleic acid molecules, such as by genetic engineering techniques.

Reference Allele:

A genotype that predominates in a natural population of organisms that do not have a disease process, such as renal disease, for example FSGS. In some examples, the reference genotype differs from mutant forms. In other examples, the reference allele is the alternative allele to a specified allele at a specific locus.

Renal Disease (Nephropathy):

A disorder that specifically leads to damage of the kidneys. Renal diseases include but are not limited to FSGS, hypertensive ESKD, nephropathy secondary to systemic lupus erythematosus, diabetic nephropathy, hypertensive nephropathy, IgA nephropathy, nephritis, and xanthine oxidase deficiency.

Renal disease can be chronic or acute. Chronic renal disease, or the type detected with the assays disclosed herein can progress from stage 1 to stage 2, stage 3, stage 4 or stage 5. The stages of chronic renal disease are:

Stage 1:

Slightly diminished kidney function; Kidney damage with normal or increased GFR (>90 mL/min/1.73 m2). Kidney damage is defined as pathologic abnormalities or markers of damage, including abnormalities in blood or urine test or imaging studies.

Stage 2:

Mild reduction in GFR (60-89 mL/min/1.73 m2) with kidney damage. Kidney damage is defined as pathologic abnormalities or markers of damage, including abnormalities in blood or urine test or imaging studies.

Stage 3:

Moderate reduction in GFR (30-59 mL/min/1.73 m2)

Stage 4:

Severe reduction in GFR (15-29 mL/min/1.73 m2)

Stage 5:

Established kidney failure (GFR<15 mL/min/1.73 m2, or permanent renal replacement therapy (RRT)

The disclosed assays can be used to detect renal disease, such as FSGS, at any of these stages, or prior to stage 1.

Risk Allele:

A "risk" allele is an allele associated with a particular type or form of disease. The risk allele identifies a single nucleotide polymorphism that can be used to detect or determine the risk for a disease, such as FSGS or hypertensive ESKD.

Sample:

A sample, such as a biological sample that includes nucleic acid molecules, is a sample obtained from a subject. As used herein, biological samples include all clinical samples useful for detection of renal disease in subjects, including, but not limited to, cells, tissues, and bodily fluids, such as: blood; derivatives and fractions of blood, such as serum; extracted galls; biopsied or surgically removed tissue, including tissues that are, for example, unfixed, frozen, fixed in formalin and/or embedded in paraffin; tears; milk; skin scrapes; surface washings; urine; sputum; cerebrospinal fluid; prostate fluid; pus; or bone marrow aspirates. In a particular example, a sample includes blood obtained from a human subject, such as whole blood or serum. In another particular example, a sample includes buccal cells, for example collected using a swab or by an oral rinse.

Sequence Identity/Similarity:

The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene*, 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

BLASTN is used to compare nucleic acid sequences, while BLASTP is used to compare amino acid sequences. To compare two nucleic acid sequences, the options can be set as follows: -i is set to a file containing the first nucleic acid sequence to be compared (such as C:\seq1.txt); -j is set to a file containing the second nucleic acid sequence to be compared (such as C:\seq2.txt); -p is set to blastn; -o is set to any desired file name (such as C:\output.txt); -q is set to -1; -r is set to 2; and all other options are left at their default setting. For example, the following command can be used to generate an output file containing a comparison between two sequences: C:\Bl2seq -i c:\seq1.txt -j c:\seq2.txt -p blastn -o c:\output.txt -q -1 -r 2.

To compare two amino acid sequences, the options of Bl2seq can be set as follows: -i is set to a file containing the first amino acid sequence to be compared (such as C:\seq1.txt); -j is set to a file containing the second amino acid sequence to be compared (such as C:\seq2.txt); -p is set to blastp; -o is set to any desired file name (such as C:\output.txt); and all other options are left at their default setting. For example, the following command can be used to generate an output file containing a comparison between two amino acid sequences: C:\Bl2seq c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1154 nucleotides is 75.0 percent identical to the test sequence (i.e., 1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (that is, 15÷20*100=75).

One indication that two nucleic acid molecules are closely related is that the two molecules hybridize to each other under stringent conditions, as described above. Nucleic acid sequences that do not show a high degree of identity may nevertheless encode identical or similar (conserved) amino acid sequences, due to the degeneracy of the genetic code. Changes in a nucleic acid sequence can be made using this degeneracy to produce multiple nucleic acid molecules that all encode substantially the same protein. Such homologous nucleic acid sequences can, for example, possess at least 60%, at least 70%, at least 80%, at least 90%, at least 95%, at least 98%, or at least 99% sequence identity (for example to a known APOL1 gene sequence) determined by this method. An alternative (and not necessarily cumulative) indication that two nucleic acid sequences are substantially identical is that the polypeptide which the first nucleic acid encodes is immunologically cross reactive with the polypeptide encoded by the second nucleic acid. One of skill in the art will appreciate that the particular sequence identity ranges are provided for guidance only.

Subject:

Living multi-cellular vertebrate organisms, a category that includes human and non-human mammals (such as laboratory or veterinary subjects).

Therapeutically Effective Amount:

An amount of a therapeutic agent that alone, or together with one or more additional therapeutic agents, induces the desired response. In one example, the desired response is decreasing the risk of developing FSGS or decreasing the signs and symptoms of FSGS. In another example, the desired response is ameliorating signs or symptoms associated with a *Trypanosoma brucei* infection, such as sleeping sickness. For example, a therapeutically effective amount of a human APOL1 protein comprising a S342G substitution, a I384M substitution and/or a deletion removing amino acids N388 and Y389, can be used to decrease symptoms associated with sleeping sickness, such as fever, headache, joint pain, lymph node swelling, anemia, confusion, reduced coordination, and disruption of the sleep cycle.

Ideally, a therapeutically effective amount provides a therapeutic effect without causing a substantial cytotoxic effect in the subject. The preparations disclosed herein are administered in therapeutically effective amounts. In general, a therapeutically effective amount of a composition administered to a human subject will vary depending upon a number of factors associated with that subject, for example the overall health of the subject, the condition to be treated, or the severity of the condition. A therapeutically effective amount of a composition can be determined by varying the dosage of the product and measuring the resulting therapeutic response. The therapeutically effective amount can be dependent on the source applied, the subject being treated, the severity and type of the condition being treated, and the manner of administration.

In one example, a desired response is to prevent the development of FSGS. In another example, a desired response is to delay the development or progression of FSGS, for example, by at least about three months, at least about six months, at least about one year, at least about two years, at least about five years, or at least about ten years. In another example, a desired response is to decrease the signs and symptoms of FSGS, such as the neurological symptoms in the limbs or associated with speaking.

Treatment:

With respect to disease, either term includes (1) preventing the disease, e.g., causing the clinical symptoms of the disease not to develop in an animal that may be exposed to or predisposed to the disease but does not yet experience or display symptoms of the disease, (2) inhibiting the disease, e.g., arresting the development of the disease or one or more of its clinical symptoms, or (3) relieving the disease, e.g., causing regression of the disease or one or more of its clinical symptoms. For example, treatment can refer to relieving one or more symptoms associated with *Trypanosoma* infection, such as sleeping sickness. Treatment of a disease does not require a total absence of disease. For example, a decrease of at least 25% or at least 50% of one or more of the symptoms or undesired consequences of the disease can be sufficient.

*Trypanosoma brucei:*

A parasite that causes African trypanosomiasis (sleeping sickness) in humans and nagana in animals in Africa. The insect vector for *T. brucei* is the tsetse fly. There are three sub-species of *T. brucei: T. b. brucei, T. b. rhodesiense* and *T. b. gambiense*. A "disease associated with *Trypanosoma* infection" includes those diseases that result from infection with *T. brucei*, such as sleeping sickness. For example, infection by *T. brucei gambiense* causes slow onset chronic trypanosomiasis in humans while infection by *T. brucei rhodesiense* causes fast onset acute trypanosomiasis in humans. *T. brucei brucei* infection causes animal African trypanosomiasis.

II. Methods for Detecting a Genetic Predisposition to and/or an Increased Risk of Developing Renal Disease Methods for determining the genetic predisposition to, or an increased risk of, development of a renal disease in a subject are provided herein. Disclosed herein are methods for determining the genetic predisposition to FSGS, as well as methods for determining the genetic predisposition of a subject to hypertensive end-stage kidney disease (EKSD). However, the methods disclosed herein also can be used to detect any form of renal disease, such as, but not limited to, FSGS or EKSD. The methods also can be used to determine the risk of developing renal disease. The methods are also useful in genetic confirmations of a diagnosis of renal disease, or to determine a therapeutic regimen for a subject. The methods are useful not only in determining risk, but for genetic confirmation of suspected chronic renal disease, for example a subject who presents with a reduced glomerular filtration rate (GFR) or other laboratory evidence of renal impairment (such as elevated blood urea nitrogen (BUN) or abnormal renal histology), or someone with clinical presentation (symptoms) of renal disease, such as fatigue and liquid retention. The methods disclosed herein can be used to determine the genetic predisposition, detect, or determine the risk of developing nephropathy secondary to systemic lupus erythematosus and other nephropathies. The methods are also useful for determining a therapeutic regimen in treating a subject of interest, or determining if a subject will benefit from treatment with a therapeutic regimen of interest. In patients having one or more APOL1 gene risk alleles, treatment while the patient is asymptomatic may be warranted.

In some embodiments, the method includes detecting the presence of a genotype (e.g., the presence of at least one risk allele), such as at least one single nucleotide polymorphism (SNP) and/or at least one inversion in a subject (e.g., one or more of the SNPs described herein, such as the G1 and/or G2 risk alleles, or an inversion in the APOL1 gene, such as the G3 allele), such that the presence of the at least one SNP and/or the at least one inversion determines genetic predisposition to (and/or increased risk of developing) renal disease in the subject. In other embodiments, the method includes detecting the presence of a genotype, such that both alleles of the genotype of the subject are risk alleles that indicate a genetic predisposition to renal disease in the subject. In other embodiments, the method includes detecting the presence of a tag SNP. In further embodiments, the method includes detecting the presence of a genotype, such that one of the alleles of the genotype is a risk allele of a tag SNP. In still other embodiments, the method includes determining whether the subject is heterozygous for an APOL1 risk allele (e.g., the subject has one risk and one non-risk allele at a given locus) or whether the subject is homozygous for at least one APOL1 risk allele (e.g., whether both alleles of the subject at a given locus include an APOL1 risk allele). In an embodiment of the method, determination that a subject is heterozygous for an APOL1 risk allele at a given locus indicates the subject has an increased risk of renal disease relative to a subject that is homozygous at that locus for a non-risk APOL1 allele, and determination that a subject is homozygous for an APOL1 risk allele at a given locus indicates the subject has a substantially increased risk of renal disease relative to a subject that is homozygous at that locus for a non-risk APOL1 allele.

In some embodiments, the method uses two or more SNPs and/or tag SNPs (alone or in combination with one or more inversions) to identify the presence in the genome of a subject of one or two or more risk haplotypes. In some embodiments, both of the haplotypes identified as carried by the subject are copies of a risk haplotype. In other embodiments, one of the haplotypes is a risk haplotype.

In some embodiments, the method includes detecting the presence of at least one SNP and at least one inversion in a gene of interest, for example. APOL1.

In some embodiments, the methods disclosed herein can be used to determine the genetic predisposition of a human subject to renal disease, wherein the subject is of African ancestry, such as an African-American subject (a subject who is of African ancestry who resides in the United States) or an African-European subject (a subject who is of African ancestry who resides in Europe) or a subject of Hispanic ancestry. In additional embodiments, the methods disclosed herein can be used to determine the genetic predisposition of a human subject to renal disease, wherein the subject is of European ancestry. The human subject can self-identify themselves (such as on a questionnaire) as being of European ancestry, such as identifying themselves as Caucasian. There are a number of programs available to confirm European ancestry, if such confirmation is desired. These include the program STRUCTURE™ (available on the internet at pritch.bsd.uchicago.edu/structure.html) and the program EURASIANDNA™, version 1.0 and 2.0 (available from DNAPRINT™). In other embodiments, the subject can self-identify themselves (such as on a questionnaire) as being of a specific ancestry. However, there are a number of programs available to confirm ancestry, if such confirmation is desired. These include the program STRUCTURE™ (available on the internet at pritch.bsd.uchicago.edu/structure.html). In several examples, the subject is infected with a human immunodeficiency virus, such as HIV-1 or HIV-2.

In some embodiments, the methods include obtaining a sample including nucleic acids from a human subject of interest, and analyzing the sample for the presence of at least one SNP and/or at least one inversion, or a haplotype including at least one tag SNP in these nucleic acids. In other embodiments, a sample is obtained that contains nucleic acids from a human subject of interest, and the sample is analyzed for the presence of a haplotype including at least two tag SNPs in a non-coding region of a gene of interest. The methods can include selecting a subject in need of detecting the presence of the SNP, and obtaining a sample including nucleic acids from this subject. For example, a subject can be selected who is suspected to possess a genetic predisposition to renal disease, such as FSGS or hypertensive ESKD. In another example, a subject can be selected that is of African ancestry and/or is infected with HIV. In a further example, a subject can be selected who has renal disease, such as, but not limited to FSGS or hypertensive ESKD. Thus, the subject's risk for progressing to another stage of renal disease can be detected. The methods disclosed herein can also be used to confirm the presence of renal disease in the subject. In yet another example, a subject with renal disease is selected to determine if a particular therapeutic regimen is appropriate for the subject. A subject of interest (e.g., an asymptomatic subject) can also be selected for preventative or prophylactic treatment based on the presence of at least one risk allele.

Biological samples include all clinical samples useful for detection of renal disease in subjects, such as cells, tissues, and bodily fluids, for example blood; derivatives and fractions of blood, such as serum; extracted galls; biopsied or surgically removed tissue, including tissues that are, for example, unfixed, frozen, fixed in formalin and/or embedded in paraffin; tears; milk; skin scrapes; surface washings; urine; sputum; cerebrospinal fluid; prostate fluid; pus; or bone marrow aspirates. In a particular example, a sample includes blood obtained from a human subject, such as whole blood or serum. In another particular example, a sample includes buccal cells, for example collected using a swab or by an oral rinse. In additional embodiments, the method includes analyzing DNA sequence data previously obtained from the subject of interest.

APOL1 SNPs and Inversions

In one example, a method for detecting genetic predisposition to, or increased risk of developing, a renal disease, such as FSGS or hypertensive ESKD, in a human subject is performed by detecting the presence of at least one SNP and/or at least one inversion in an APOL1 gene (e.g., an inversion that replaces all or a portion of the first, second, and/or third exon of the APOL1 gene with another apolipoprotein gene, such as the APOL4 gene). In particular examples, specific SNPs of use in identifying a genetic predisposition to renal disease (for example, in a subject of African ancestry, such as an African-American subject) include a G at rs73885319, a G at rs60910145, a 6 bp deletion (−/TTATAA; SEQ ID NO: 6) at rs71785313, and/or combinations thereof. In some examples SNP rs73885319 results in a substitution of glycine for serine at amino acid 342 of an APOL1 protein (S342G). In other examples, SNP rs60910145 results in a substitution of methionine for isoleucine at amino acid 384 of an APOL1 protein (I384). In further examples, SNP rs71785313 results in a deletion of amino acids 388 and 389 of an APOL1 protein. In other examples, a specific inversion is the G3 inversion discussed below).

The method can also include detecting one of more of the APOL1 SNPs and/or inversions disclosed herein. Thus, the method can include detecting at least one, at least two, or at least three different SNPs and/or at least one, two, or three different inversions. In some embodiments, the SNPs can be in any combination, of at least two different SNPs. Detection of all of the SNPs disclosed herein can also be used to detect a genetic predisposition to renal disease, such as FSGS or hypertensive ESKD.

In several embodiments, at least one SNP is detected in a coding region of an APOL1 gene. Thus, the method can include detecting at least one, at least two, or at least three different SNPs in the coding region of an APOL1 gene, wherein at least one or more SNPs in the coding region of the gene is a G at rs73885319, a G at rs60910145, and/or a 6 bp deletion (−/TTATAA; SEQ ID NO: 6) at rs71785313. In some examples, a G at rs73885319 includes an APOL1 nucleic acid having a G at nucleotide 1024 of SEQ ID NO: 4. In some examples, a G at rs60910145 includes an APOL1 nucleic acid having a G at nucleotide 1052 of SEQ ID NO: 4. In some examples, a 6 bp deletion at rs71785313 includes an APOL1 nucleic acid having a deletion of nucleotides 1064-1069 of SEQ ID NO: 4.

With regard to the SNPs, the SNPs can be identified by name. The exact sequence of the SNP can be determined from the database of SNPs available at the NCBI website (ncbi.nlm.nih.gov/SNP, Apr. 18, 2010). The "position" of the nucleotide of interest is the location in the genome of the SNP, referring to the nucleotide position from the p-terminus of the chromosome in the human genome, see the NCBI SNP website, available on the internet. Sequence information for each of the APOL1 SNPs listed above is provided in Table 1.

TABLE 1

APOL1 single nucleotide polymorphisms

| SNP | Risk allele | Reference allele | Flanking sequence |
|---|---|---|---|
| rs73885319 | G | A | TCAAGCTCACGGATGTGGCCCCTGTA[G/A]GCTTCTTTC TTGTGCTGGATGTAGT (SEQ ID NO: 1) |
| rs60910145 | G | T | CAGGAGCTGGAGGAGAAGCTAAACAT[G/T]CTCAACAAT AATTATAAGATTCTGC (SEQ ID NO: 2) |
| rs71785313 | del6 | TTATAA (SEQ ID NO: 6) | GAGAAGCTAAACATTCTCAACAATAA[-/TTATAA]GATT CTGCAGGCGGACCAAGAACTG (SEQ ID NO: 3) |

In Table 1, the "risk" allele identifies the SNP that can be used to detect or determine the risk for renal disease, such as FSGS or hypertensive ESKD. The "reference" allele is a different allele not associated with renal disease, and thus is a "protective allele" as this allele indicates that the subject does not have or is not at risk for developing renal disease, such as FSGS or hypertensive ESKD. In the sequences provided above, the notation "[X/Y]" is used, wherein one of X or Y is the risk allele and one of X or Y is the reference (protective) allele. For each sequence, the allele associated with renal disease (the "risk" allele) is listed. The allele that is associated with a decreased risk (or absence) of renal disease is also listed (the "reference" allele).

Another risk allele that can be used to detect or determine the risk for renal disease, such as FSGS or hypertensive ESKD, is an APOL1 gene chromosomal rearrangement that inverts a segment of DNA including the 5' end of APOL4, all of APOL2, and the 5' end of APOL1, which produces an APOL4/APOL1 hybrid gene. The inversion is referred to herein as the "G3" risk allele.

The disclosed methods can include detecting at least one risk allele (e.g., G1, G2, del6, and/or G3) on one or both chromosomes, detecting the presence of a protective allele on one or both chromosomes, or detecting the absence of the protective allele on one or both chromosomes. In some embodiments, detecting the presence of the risk allele indicates that the subject has a genetic predisposition to renal disease, and detecting the absence of the protective allele indicates that the subject has a genetic predisposition to renal disease. Similarly, detecting the absence of the risk allele indicates that the subject does not have a genetic predisposition to renal disease, and detecting the presence of the protective allele indicates that the subject does not have a genetic predisposition to renal disease.

Thus, the disclosed methods can detect a low risk of developing renal disease, or identify a subject that does not have a genetic pre-disposition to developing renal disease. For example, subjects that have at least one SNP associated with the reference allele are not genetically pre-disposed to developing renal disease, such as FSGS or hypertensive ESKD. These subjects do not have renal disease and/or have a low risk for developing renal disease.

In subjects of African ancestry, the methods include detecting the presence at least one SNP (e.g., G1, G2, and/or del6) in the last (3') exon of the APOL1 gene or at least one inversion in an APOL1 gene (e.g., G3). An exemplary nucleic acid sequence for human apolipoprotein L1 is:

(SEQ ID NO: 4)
```
atggagggag ctgctttgct gagagtctct gtcctctgca tctggatgag tgcactttc
cttggtgtgg gagtgagggc agaggaagct ggagcgaggg tgcaacaaaa cgttccaagt
gggacagata ctggagaLcc tcaaagtaag ccuctoggtg actgggctgc tggcaccatg
gacccagaga gcagtatctt tattgaggat gccattaagt atttcaagga aaaagtgagc
acacagaatc tgctactcct gctgactgat aatgaggcct ggaacggatt cgtggctgct
gctgaactgc ccaggaatga ggcagatgag ctccgtaaag ctctggacaa ccttgcaaga
caaatgatca tgaaagacaa aaactggcac gataaaggcc agcagtacag aaactggttt
ctgaaagagt ttcctcggtt gaaaagtgag cttgaggata acataagaag gctccgtgcc
cttgcagatg gggttcagaa ggtccacaaa ggcaccacca tcgccaatgt ggtgtctggc
tctctcagca tttcctctgg catcctgacc ctcgtcggca tgggtctggc acccttcaca
gagggaggca gccttgtact cttggaacct gggatggagt tgggaatcac agccgctttg
accgggatta ccagcagtac catggactac ggaaagaagt ggtggacaca agcccaagcc
cacgacctgg tcatcaaaag ccttgacaaa ttgaaggagg tgagggagtt tttgggtgag
aacatatcca actttctttc cttagctggc aatacttacc aactcacacg aggcattggg
```

```
aaggacatcc gtgccctcag acgagccaga gccaatcttc agtcagtacc gcatgcctca gcctcacgcc cccgggtcac tgagccaatc tcagctgaaa gcggtgaaca ggtggagagg gttaatgaac ccagcatcct ggaaatgagc agaggagtca agctcacgga tgtggcccct gtaagcttct ttcttgtgct ggatgtagtc tacctcgtgt acgaatcaaa gcacttacat gaggggggcaa agtcagagac agctgaggag ctgaagaagg tggctcagga gctggaggag aagctaaaca ttctcaacaa taattataag attctgcagg cggaccaaga actgtga
```

An exemplary amino acid sequence for human apolipoprotein L1 is:

```
                                                          (SEQ ID NO: 5)
megaallrvs vlciwmsalf lgvgvraeea garvqqnvps gtdtgdpqsk plgdwaagtm dpessified aikyfkekvs tqnllllltd neawngfvaa aelprneade lrkaldnlar qmimkdknwh dkgqqyrnwf lkefprlkse lednirrlra ladgvqkvhk gttianvvsg slsissgilt lvgmglapft eggslvllep gmelgitaal tgitsstmdy gkkwwtqaqa hdlviksldk lkevreflge nisntlslag ntyqltrgig kdiralrrar anlqsvphas asrprvtepi saesgegver vnepsilems rgvkltdvap vsfflvldvv ylvyeskhlh egaksetaee lkkvagelee klnilnnnyk ilgadgel
```

Methods are also disclosed for detection of a genetic predisposition to renal disease, such as FSGS or hypertensive ESKD, or both in a human subject of European ancestry. The assay can be used for early diagnosis, for example before the development of renal insufficiency or renal failure, or for confirming the diagnosis of renal disease. The presence of at least one SNP or at least one inversion in an APOL1 gene that encodes apolipoprotein L1 determines the genetic predisposition to FSGS or hypertensive ESKD or both in the human subject of European ancestry. In one embodiment, the method includes detecting at least one of a G at rs73885319, a G at rs60910145, and/or a 6 bp deletion (−/TTATAA; SEQ ID NO: 6) at rs71785313 and/or at least one inversion. In a further example, the method includes detecting the absence of at least one of a G at rs73885319, a G at rs60910145, and/or a 6 bp deletion (−/TTATAA; SEQ ID NO: 6) at rs71785313 and/or at least one inversion. In some examples, a G at rs73885319 includes an APOL1 nucleic acid having a G at nucleotide 1024 of SEQ ID NO: 4. In some examples, a G at rs60910145 includes an APOL1 nucleic acid having a G at nucleotide 1052 of SEQ ID NO: 4. In some examples, a 6 bp deletion at rs71785313 includes an APOL1 nucleic acid having a deletion of nucleotides 1064-1069 of SEQ ID NO: 4.

In a further embodiment, the frequency of the risk allele in subjects of African ancestry is at least 5%, at least 10%, at least 15%, at least 20%, at least 25%, at least 30%, at least 35%, at least 40% or at least 50%. In several instances, the SNP and/or inversion is in a coding region of an APOL1 gene. In several embodiments, the SNP used to identify the frequency of the risk allele in subjects of African ancestry is set forth in Table 1 and also may include at least one inversion. In one embodiment, the subject of African ancestry is African-American.

In other embodiments, the risk of renal disease in a subject of African or Hispanic ancestry increases if the subject has at least one risk allele (e.g., at least one of a G1, G2, del6, and/or G3 allele). Subjects of African or Hispanic ancestry that have at least two (or more) of APOL1 gene risk alleles exhibit a significantly increased risk of developing renal disease. The methods of the invention may further include assaying the subject for the presence of a wild type allele (relative to an APOL1 gene risk allele) as a means for determining whether the subject has a moderate or increased risk of renal disease. For example, a subject that is heterozygous at a given locus for one or more of the APOL1 gene risk alleles may have a greater risk of renal disease relative to a subject lacking any APOL1 gene risk alleles. A subject that is homozygous at a given locus for one or more APOL1 gene risk alleles may have a risk of renal disease that is greater than that of a subject that is heterozygous for an APOL1 gene risk allele at that locus and a subject that lacks any risk alleles in an APOL1 gene. The presence of two or more (e.g., three, four, or more) risk alleles at different loci further increases the likelihood of renal disease in a subject.

In other embodiments, a subject having one or more (e.g., two, three, or four or more) APOL1 gene risk alleles (e.g., at least one SNP, e.g., G1, G2, and/or del6, and/or at least one inversion, such as the G3, risk allele; the subject may also be heterozygous or homozygous for one or more of these risk alleles) may be offered a treatment regimen that is different from that of a subject having no or only one APOL1 gene risk alleles. For example, a subject having one or more APOL1 gene risk alleles may be treated with a medication or therapy to reduce or prevent renal disease while the subject is asymptomatic (e.g., the subject may be subjected to a change in diet, an increase in exercise, a reduction in the intake of NSAIDs, a regimen of blood pressure medication(s) (see list below) that do not produce a renal toxicity profile, hemodialysis, peritoneal dialysis, or transplantation). The treatment of such a patient may begin at a time point that is earlier than that for a subject having no or only one APOL1 gene risk allele; the amount of medication that is prescribed to such a patient may be increased or decreased in order to avoid further harm to the kidneys; or the type(s) of medication(s) may be adjusted, relative to a subject having no or only one APOL1 risk allele.

In other embodiments, a subject having one or more APOL1 gene risk alleles may be offered a treatment regimen with respect to blood pressure medications, steroids, and/or immunosuppressive agents, that is different from a subject lacking any (or only having, e.g., one) APOL1 gene risk allele. In particular, subjects having one or more APOL1 gene risk alleles are more susceptible to renal damage and/or disease and the risk of kidney damage increases in patients having one or more APOL1 gene risk alleles that are treated with blood pressure medications, steroids, and/or immunosuppressive agents that exhibit renal toxic side effects. Thus, in patients having one or more APOL1 gene risk alleles, the concentration of a given blood pressure medication, steroid, and/or immunosuppressive agent and/or the length of treatment may be decreased relative to a patient lacking any (or having only one) APOL1 gene risk alleles to avoid damage to the patient's kidneys. The change in therapeutic regimen in patients having one or more APOL1 gene risk alleles may occur while the patients are asymptomatic.

Examples of therapeutics include blood pressure medications (e.g., a diuretic (e.g., chlorthalidone, chlorothiazide, furosemide, hydrochlorothiazide, indapamide, metolazone, amiloride hydrochloride, spironolactone, triamterene, bumetanide, or a combination thereof), an alpha adrenergic antagonist (e.g., alfuzosin, doxazosin, prazosin, terazosin, or tamsulosin, or a combination thereof), a central adrenergic inhibitor (e.g., clonidine, guanfacine, or methyldopa, or a combination thereof), an angiotensin converting enzyme (ACE) inhibitor (e.g., benazepril, captopril, enalapril, fosinopril, lisinopril, moexipril, perindopril, quinapril, ramipril, or trandolapril, or combinations thereof), an angiotensin II receptor blocker (e.g., candesartan, eprosartan, irbesartan, losartan, olmesartan, telmisartan, or valsartan, or combinations thereof), an alpha blocker (e.g., doxazosin, prazosin, or terazosin, or a combination thereof), a beta blocker (e.g., acebutolol, atenolol, betaxolol, bisoprolol, carteolol, metoprolol, nadolol, nebivolol, penbutolol, pindolol, propranolol, solotol, or timolol, or a combination thereof), a calcium channel blocker (e.g., amlodipine, bepridil, diltiazem, felodipine, isradipine, nicardipine, nifedipine, nisoldipine, or verapamil, or combination thereof), a vasodilator (e.g., hydralazine or minoxidil, or combination thereof), and a renin inhibitor (e.g., aliskiren), or combinations thereof), a steroid (e.g., a corticosteroid, such as cortisone, prednisone, methylprednisolone, or prednisolone), or an anabolic steroid (anatrofin, anaxvar, annadrol, bolasterone, decadiabolin, decadurabolin, dehydropiandrosterone (DHEA), delatestryl, dianiabol, dihydrolone, durabolin, dymethazine, enoltestovis, equipose, gamma hydroxybutyrate, maxibolin, methatriol, methyltestosterone, parabolin, primobolin, quinolone, therabolin, trophobolene, and winstrol), or an immunosuppressive agent, such as a glucocorticoid, a cytostatic, an antibody, or an anti-immunophilin and/or mychophenolate mofetil (MMF), FK-506, azathioprine, cyclophosphamide, methotrexate, dactinomycin, antithymocyte globulin (AT-GAM), an anti-CD20-antibody, a muromonoab-CD3 antibody, basilizimab, daclizumab, cyclosporin, tacrolimus, voclosporin, sirolimus, an interferon, infliximab, etanercept, adalimumab, fingolimod, and/or myriocin).

Subjects having African ancestry (including some subjects of Hispanic ancestry) exhibit a 35-45% increased risk of renal disease when that subject is determined to have at least one APOL1 gene risk allele (e.g., G1, G2, del6, and or G3). The risk of FSGS increases by 10-fold in these subjects. Surprisingly, the risk of HIV-associated nephropathy increases by 50-fold in subjects having at least one risk allele. In addition, the risk of ESKD increases by 7-8 fold in subjects having at least one risk allele. These risk factors are not seen in non-African patients lacking one or more of these risk alleles.

In a typical population of subjects of African ancestry, at least 10-15% of the population is at high risk of renal disease due to the presence of one or more risk alleles. Thirty percent of these subjects are at slight or increased risk, while 55% are at low risk of renal disease. Those subjects having two risk alleles are at the greatest risk of renal disease. The rate of renal disease in subjects of non-African ancestry is essentially the same for subjects of African ancestry with 0 or, in some instances, 1 risk allele. Thus, the presence of APOL1 risk alleles account for most of the large increase in renal disease risk in black compared to white individuals.

Kidney Transplantation

A subject in need of kidney transplantation can also be genotyped for the presence of at least one risk allele in the APOL1 gene disclosed herein. It is known that individuals of African ancestry, including those individuals of Hispanic ancestry and, in particular, African-Americans, have an elevated risk for carrying one or two copies of at least one risk allele the APOL1 gene, which increases their risk of developing idiopathic kidney disease. Thus, in one embodiment, a kidney recipient can be genotyped to determine if the recipient carries one or two copies of at least one of the disclosed risk alleles the APOL1 gene. Additionally, a kidney selected for transplantation can undergo genotyping prior to surgery to establish the genotype status of the organ.

In some embodiments, if the recipient is negative for risk alleles in the APOL1 gene and the donor kidney is positive for risk alleles in the APOL1 gene, then the recipient is given pre- and/or post-transplantation treatment regimens that reduce the risk of the donated kidney undergoing subsequent kidney failure. Additionally, it may be necessary to treat a subject who is to receive a kidney that is positive for one or more risk alleles in the APOL1 gene differently from a subject who is to receive a kidney that does not possess an APOL1 risk allele. Therapeutic treatment and regimens can therefore be developed after genotyping of a subject or an organ for APOL1 genotype. These treatment regimens may include decreasing the dosage of, or the length of treatment with, one or more therapeutics in those individuals having at least one (e.g., two or more) risk alleles. These therapeutics include blood pressure medications, steroids, and immunosuppressive agents (see list above).

In other embodiments, the determination that a potential transplantation donor has one or more risk alleles in the APOL1 gene (e.g., at least one risk allele at a given locus on one or both chromosomes) indicates that an organ (e.g., a kidney) of the donor is not suitable or has a lower suitability for transplant into a recipient relative to a potential transplant donor that lacks one or more risk alleles in the APOL1 gene (e.g., at least one risk allele at a given locus on one or both chromosomes).

III. Methods for Identifying Resistance to Infection by *Trypanosoma*

APOL1 is a trypanolytic factor of human serum (Vanhamme et al., *Nature* 422:83-87, 2003; Perez-Morga et al., *Science* 309:469-472, 2005). The APOL1 variants disclosed herein exhibit the ability to kill *Trypanosoma brucei*, the parasite responsible for sleeping sickness disease. Therefore, the disclosed APOL1 variants can be used to detect resistance of a subject (for example, a mammal, such as a human subject) to a disease associated with *Trypanosoma* infection.

*Trypanosoma brucei* is a heterotrophic species from the *Trypanosoma* genus. It exists in two forms: an insect vector, and once inside the bloodstream, a mammalian host. *T. brucei* exists as its insect vector in the tsetse fly, a large, biting fly originating in Africa. Once the tsetse fly bites a mammal, the microbe enters the bloodstream where it transforms into the mammalian host form, and is then capable of mutating and invading the central nervous system, (CNS). Once inside the CNS, it has the ability to inflict African trypanosomiasis, (sleeping sickness).

There are three sub-species of *T. brucei: T. b. brucei, T. b. gambiense,* and *T. b. rhodesiense. T. b. gambiense* causes slow onset chronic trypanosomiasis in humans. It is most common in central and western Africa, where humans are thought to be the primary reservoir. *T. brucei rhodesiense* and/or the inversions disclosed herein can also be used to detect resistance to a disease associated with *Trypanosoma* infection (e.g., G1, G2, del6, and/or G3).

In several embodiments, at least one SNP and/or at least one inversion is detected in a coding region of an APOL1 gene. Thus, the method can include detecting at least one, at least two, or at least three different SNPs and/or inversions in the coding region of an APOL1 gene, wherein at least one or more SNPs in the coding region of the gene is a G at rs73885319, a G at rs60910145, or a 6 bp deletion (−/TTATAA; SEQ ID NO: 6) at rs71785313, and/or one of the inversions is G3. Sequence information for each of the APOL1 SNPs listed above is provided in Table 2.

TABLE 2

APOL1 single nucleotide polymorphisms

| SNP | Resistance allele | Reference allele | Flanking sequence |
|---|---|---|---|
| rs73885319 | G | A | TCAAGCTCACGGATGTGGCCCCTGTA[G/A]GCTTCT TTCTTGTGCTGGATGTAGT (SEQ ID NO: 1) |
| rs60910145 | G | T | CAGGAGCTGGAGGAGAAGCTAAACAT[G/T]CTCAAC AATAATTATAAGATTCTGC (SEQ ID NO: 2) |
| rs71785313 | del6 | TTATAA (SEQ ID NO: 6) | GAGAAGCTAAACATTCTCAACAATAA[-/TTATAA] GATTCTGCAGGCGGACCAAGAACTG (SEQ ID NO: 3) | causes fast onset acute trypanosomiasis in humans and is most common in southern and eastern Africa, where game animals and livestock are thought to be the primary reservoir. *T. brucei brucei* causes animal African trypanosomiasis. *T. b. brucei* is generally not human infective due to its susceptibility to lysis by human apolipoprotein L1. *T. b. gambiense* parasites can further be divided into two types, type 1, which is homogeneous and clearly distinct from *T. b. rhodesiense,* and type 2, which is heterogeneous and shares characteristics with *T. b. rhodesiense.*

In one example, a method for detecting resistance to a disease associated with *Trypanosoma* (such as sleeping sickness) in a human subject is performed by detecting the presence of at least one SNP or at least one inversion in an APOL1 gene (e.g., G1, G2, del6, and/or G3). In particular examples, specific SNPs of use in identifying resistance to a disease associated with *Trypanosoma* (for example, in a subject of African ancestry) include a G at rs73885319, a G at rs60910145, a 6 bp deletion (−/TTATAA; SEQ ID NO: 6) at rs71785313, and combinations thereof. In some examples SNP rs73885319 results in a substitution of glycine for serine at amino acid 342 of an APOL1 protein (S342G). In other examples, SNP rs60910145 results in a substitution of methionine for isoleucine at amino acid 384 of an APOL1 protein (I384). In further examples, SNP rs71785313 results in a deletion of amino acids 388 and 389 of an APOL1 protein.

The method can also include detecting one of more of the APOL1 SNPs or inversions disclosed herein. Thus, the method can include detecting at least one, at least two, or at least three different SNPs (such as 1, 2, or 3 SNPs or inversions). In some embodiments, the SNPs and/or inversion can be in any combination (e.g., a combination of at least two different SNPs alone or in combination with an inversion). Detection of one or more (e.g., all) of the SNPs In Table 2, the "resistance" allele identifies the SNP that can be used to detect or determine resistance to a disease associated with *Trypanosoma* infection, such as sleeping sickness. The "reference" allele is a different allele not associated with disease resistance. In the sequences provided above, the notation "[X/Y]" is used, wherein one of X or Y is the resistance allele and one of X or Y is the reference allele. For each sequence, the allele associated with resistance to disease associated with *Trypanosoma* infection (the "resistance" allele) is listed. The allele that is not associated with a resistance to disease is also listed (the "reference" allele).

The disclosed methods can include detecting the resistance allele on one or both chromosomes, detecting the presence of a reference allele on one or both chromosomes, or detecting the absence of the resistance allele on one or both chromosomes. In some embodiments, detecting the presence of the resistance allele indicates that the subject has a resistance to disease associated with *Trypanosoma* infection, and detecting the absence of the reference allele indicates that the subject has a resistance to disease associated with *Trypanosoma* infection. In particular examples, detecting the presence of the resistance allele indicates that the subject has a resistance to disease associated with *T. b. rhodesiense* infection (such as disease associated with infection with type 1 *T. b. rhodesiense* or type 2 *T. b. rhodesiense*). Similarly, detecting the absence of the resistance allele indicates that the subject does not have a resistance to disease associated with *Trypanosoma* infection (such as disease associated with infection with type 1 *T. b. rhodesiense* or type 2 *T. b. rhodesiense*), and detecting the presence of the reference allele indicates that the subject does not have a resistance to disease associated with *Trypanosoma* infection.

Thus, the disclosed methods can detect resistance to disease associated with *Trypanosoma* infection, such as decreased risk of developing *Trypanosoma*-associated disease, or identify a subject that does not have a resistance to disease associated with *Trypanosoma* infection. For example, subjects that have at least one APOL1 SNP associated with the resistance allele are genetically pre-disposed to resistance to disease associated with *Trypanosoma* infection. In particular examples, the subject is of African or Hispanic ancestry. In further examples, the subject is African-American.

Methods are also disclosed for detection of a resistance to disease associated with *Trypanosoma* infection in a human subject of European ancestry. The presence of at least one SNP in an APOL1 gene that encodes apolipoprotein L1 determines the genetic predisposition to resistance to disease associated with *Trypanosoma* infection in the human subject of European ancestry. In one embodiment, the method includes detecting at least one of a G at rs73885319, a G at rs60910145, and/or a 6 bp deletion (–/TTATAA; SEQ ID NO: 6) at rs71785313, and/or at least one inversion in the APOL1 gene (e.g., G3). In a further example, the method includes detecting the absence of at least one of a G at rs73885319, a G at rs60910145, and/or a 6 bp deletion (–/TTATAA; SEQ ID NO: 6) at rs71785313 and/or at least at least one inversion in the APOL1 gene (e.g., G3).

IV. Methods and Compositions for Treating Disease Associated with *Trypanosoma* Infection It has been discovered that human plasma from individuals expressing variant APOL1 proteins (for example, S342G/I384M and/or del N388/Y389 and/or the G3 inversion) lyses *Trypanosoma brucei* parasites (such as SRA– or SRA+ *T. brucei*) in vitro. Therefore, disclosed herein are methods for treating a subject infected with *Trypanosoma brucei* (such as *T. b. brucei*, *T. b. rhodesiense*, or *T. b. gambiense*) utilizing the variant APOL1 proteins described herein. In some embodiments, the method includes administering to a subject a therapeutically effective amount of a variant APOL1 protein, such as an APOL1 protein with a S342G substitution, an I384M substitution and/or a deletion removing amino acids N388 and Y389 and/or an APOL1 with a G3 inversion. For example, a therapeutically effective amount of a human APOL1 protein including 1, 2, 3 or all 4 of these mutations can be used. For example, a therapeutically effective amount of a human APOL1 protein including a S342G substitution, an I384M substitution and/or a deletion removing amino acids N388 and Y389 and/or an APOL1 with a G3 inversion, can be used to decrease symptoms associated with sleeping sickness, such as fever, headache, joint pain, lymph node swelling, anemia, confusion, reduced coordination, and disruption of the sleep cycle. In particular examples, the subject is infected with *T. b. rhodesiense* (for example, type 1 *T. b. rhodesiense* or type 2 *T. b. rhodesiense*).

A subject infected with *T. brucei* is identified by standard diagnostic methods. In some examples, diagnosis includes demonstrating presence of trypanosomes in the subject, for example by microscopic examination of chancre fluid, lymph node aspirates, blood, bone marrow, or, in the late stages of infection, cerebrospinal fluid. In some examples, a wet preparation is examined for motile trypanosomes and a smear is fixed, stained with Giemsa (or Field), and examined. In other examples, a serological test is used to detect presence of anti-trypanosome antibodies. Particular serological tests include agglutination tests, such as micro-CATT, wb-CATT, and wb-LATEX (e.g., Truc et al., *Bull: World Health Org.* 80:882-886, 2002). In further examples, a diagnosis is based on clinical symptoms, including non-specific symptoms (such as fever, fatigue, headache, arthralgia, and pruritus), enlarged cervical lymph nodes in the posterior cervical triangle (Winterbottom's sign), and neuropsychiatric symptoms and signs (such as mental disturbance, disturbance of the sleep-wake cycle, rigidity and tremor, dysarthria, and ataxia).

Disclosed herein are methods of treating a subject infected with *T. brucei* which include administering to the subject a therapeutically effective amount of a variant APOL1 protein, such as an APOL1 protein including a S342G substitution, an I384M substitution and/or a deletion removing amino acids N388 and Y389, and/or an APOL1 with a G3 inversion. In some embodiments, the method includes administering a therapeutically effective amount of human serum or HDL particles including at least one APOL1 variant protein (such as an APOL1 protein including a S342G substitution, an I384M substitution and/or a deletion removing amino acids N388 and Y389, and/or an APOL1 protein with a G3 inversion).

Appropriate human donors for obtaining human serum or HDL particles containing APOL1 variant protein can be identified utilizing the genotyping methods described herein. In some examples, a donor is an individual with an APOL1 gene having at least one of a G at rs73885319, a G at rs60910145, and/or a 6 base pair deletion at rs71785313 and/or an APOL1 gene with a G3 inversion.

In some examples, a therapeutically effective amount of human serum includes at least a 10-fold dilution of serum from a donor with an APOL1 protein including a S342G substitution, an I384M substitution and/or a deletion removing amino acids N388 and Y389 and/or an APOL1 protein with a G3 inversion (such as at least a 100-fold, 1000-fold, 10,000-fold, 100,000-fold or more dilution). It will be appreciated that these dosages are examples only, and an appropriate dose can be determined by one of ordinary skill in the art using only routine experimentation.

In other embodiments, the method includes administering a therapeutically effective amount of a recombinant APOL1 protein, including at least one APOL1 variant (such as an APOL1 protein including a S342G substitution, an I384M substitution and/or a deletion removing amino acids N388 and Y389 and/or an APOL1 protein with a G3 inversion.). In some examples, a therapeutically effective amount of recombinant APOL1 variant protein includes about 0.1 mg/kg to about 1000 mg/kg (such as about 1 mg/kg to 1000 mg/kg, about 10 mg/kg to 500 mg/kg, about 10 mg/kg to 100 mg/kg, about 50 mg/kg to 500 mg/kg, or about 100 mg/kg to 1000 mg/kg). Administration can be accomplished by single or multiple doses. The dose required will vary from subject to subject depending on the species, age, weight and general condition of the subject, the particular therapeutic agent being used and its mode of administration. It will be appreciated that these dosages are examples only, and an appropriate dose can be determined by one of ordinary skill in the art using only routine experimentation.

The preparation of recombinant proteins is well known to those skilled in the art. See, e.g., Sambrook et al. (In *Molecular Cloning: A Laboratory Manual*, CSHL, New York, 1989); Ausubel et al. (In *Current Protocols in Molecular Biology*, John Wiley & Sons, New York, 1998); and *The Recombinant Protein Handbook*, GE Lifesciences, Code 18-1142-75.

Also disclosed herein are pharmaceutical compositions that include a variant APOL1 protein (such as APOL1 protein including a S342G variant, an I384M variant, and/or a del N388/Y389 variant, and/or an APOL1 protein with a G3 inversion, or a combination thereof), such as a recombinant APOL1 protein. In some embodiments, the composition includes a pharmaceutically acceptable carrier. Pharmaceutically acceptable carriers are determined in part by the particular composition being administered, as well as by the particular method used to administer the composition. Accordingly, there is a wide variety of suitable formulations of pharmaceutical compositions of the present disclosure. See, e.g., Remington: The Science and Practice of Pharmacy, The University of the Sciences in Philadelphia, Editor, Lippincott, Williams, & Wilkins, Philadelphia, Pa., 21$^{st}$ Edition (2005).

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

V. Molecular Methods

Generally, the methods disclosed herein involve an assessment of nucleic acid sequence. Molecular techniques of use in all of these methods are disclosed below.

Preparation of Nucleic Acids for Analysis:

Nucleic acid molecules can be prepared for analysis using any technique known to those skilled in the art. Generally, such techniques result in the production of a nucleic acid molecule sufficiently pure to determine the presence or absence of one or more variations at one or more locations in the nucleic acid molecule. Such techniques are described for example, in Sambrook, et al., Molecular Cloning: A Laboratory Manual (Cold Spring Harbor Laboratory, New York) (1989), and Ausubel, et al., Current Protocols in Molecular Biology (John Wiley and Sons, New York) (1997), incorporated herein by reference.

When the nucleic acid of interest is present in a cell, it can be necessary to first prepare an extract of the cell and then perform further steps, such as differential precipitation, column chromatography, extraction with organic solvents and the like, in order to obtain a sufficiently pure preparation of nucleic acid. Extracts can be prepared using standard techniques in the art, for example, by chemical or mechanical lysis of the cell. Extracts then can be further treated, for example, by filtration and/or centrifugation and/or with chaotropic salts such as guanidinium isothiocyanate or urea or with organic solvents such as phenol and/or chloroform to denature any contaminating and potentially interfering proteins. When chaotropic salts are used, it can be desirable to remove the salts from the nucleic acid-containing sample. This can be accomplished using standard techniques in the art such as precipitation, filtration, size exclusion chromatography and the like. In some examples, nucleic acids can be isolated using commercially available kits (e.g., Qiagen, Valencia, Calif.; Life Technologies/Invitrogen, Carlsbad, Calif.; Epicentre, Madison, Wis.).

In some instances, messenger RNA can be extracted from cells. Techniques and material for this purpose are known to those skilled in the art and can involve the use of oligo dT attached to a solid support such as a bead or plastic surface. In some embodiments, the mRNA can be reverse transcribed into cDNA using, for example, a reverse transcriptase enzyme. Suitable enzymes are commercially available from, for example, Life Technologies/Invitrogen (Carlsbad, Calif.). Optionally, cDNA prepared from mRNA can also be amplified.

Amplification of Nucleic Acid Molecules:

Optionally, the nucleic acid samples obtained from the subject are amplified prior to detection. Target nucleic acids are amplified to obtain amplification products, including a SNP or sequences from a haplotype block including a tag SNP, can be amplified from the sample prior to detection. Typically, DNA sequences are amplified, although in some instances RNA sequences can be amplified or converted into cDNA, such as by using RT PCR.

Any nucleic acid amplification method can be used. An example of in vitro amplification is the polymerase chain reaction (PCR), in which a biological sample obtained from a subject is contacted with a pair of oligonucleotide primers, under conditions that allow for hybridization of the primers to a nucleic acid molecule in the sample. The primers are extended under suitable conditions, dissociated from the template, and then re-annealed, extended, and dissociated to amplify the number of copies of the nucleic acid molecule. Other examples of in vitro amplification techniques include quantitative real-time PCR, strand displacement amplification (see U.S. Pat. No. 5,744,311); transcription-free isothermal amplification (see U.S. Pat. No. 6,033,881); repair chain reaction amplification (see PCT Publication No. WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

In specific examples, the target sequences to be amplified from the subject include at least one APOL1 SNP, one or more different haplotype blocks including a tag SNP, or a nucleotide sequence of interest including the tag SNP. In certain embodiments, target sequences containing one or more of SEQ ID NOs: 1-3, or a subset thereof, are amplified. In an embodiment, a single SNP with exceptionally high predictive value is amplified, or a nucleic acid encoding the SNP is amplified.

A pair of primers can be utilized in the amplification reaction. One or both of the primers can be labeled, for example with a detectable radiolabel, fluorophore, or biotin molecule. The pair of primers includes an upstream primer (which binds 5' to the downstream primer) and a downstream primer (which binds 3' to the upstream primer). The pair of primers used in the amplification reactions are selective primers which permit amplification of a size related marker locus. Primers can be selected to amplify a nucleic acid including a SNP, a haplotype block including a tag SNP, or a nucleic acid including a tag SNP. Numerous primers can be designed by those of skill in the art simply by determining the sequence of the desired target region of APOL1, for example, using well known computer assisted algorithms that select primers within desired parameters suitable for annealing and amplification.

If desired, an additional pair of primers can be included in the amplification reaction as an internal control. For example, these primers can be used to amplify a "housekeeping" nucleic acid molecule, and serve to provide confirmation of appropriate amplification. In another example, a target nucleic acid molecule including primer hybridization sites can be constructed and included in the amplification reactor. One of skill in the art will readily be able to identify primer pairs to serve as internal control primers.

Primer Design Strategy:

Increased use of polymerase chain reaction (PCR) methods has stimulated the development of many programs to aid in the design or selection of oligonucleotides used as primers for PCR. Four examples of such programs that are freely available via the Internet are: PRIMER™ by Mark Daly and Steve Lincoln of the Whitehead Institute (UNIX, VMS, DOS, and Macintosh), Oligonucleotide Selection Program by Phil Green and LaDeana Hiller of Washington University in St. Louis (UNIX, VMS, DOS, and Macintosh), PGEN™ by Yoshi (DOS only), and Amplify by Bill Engels of the University of Wisconsin (Macintosh only). Generally these programs help in the design of PCR primers by searching for bits of known repeated-sequence elements and then optimizing the $T_m$ by analyzing the length and GC content of a putative primer. Commercial software is also available and primer selection procedures are rapidly being included in most general sequence analysis packages.

Designing oligonucleotides for use as either sequencing or PCR primers requires selection of an appropriate sequence that specifically recognizes the target APOL1, and then testing the sequence to eliminate the possibility that the oligonucleotide will have a stable secondary structure. Inverted repeats in the sequence can be identified using a repeat-identification or RNA-folding programs. If a possible stem structure is observed, the sequence of the primer can be shifted a few nucleotides in either direction to minimize the predicted secondary structure. When the amplified sequence is intended for subsequence cloning, the sequence of the oligonucleotide can also be compared with the sequences of both strands of the appropriate vector and insert DNA. A sequencing primer only has a single match to the target DNA. It is also advisable to exclude primers that have only a single mismatch with an undesired target DNA sequence. For PCR primers used to amplify genomic DNA, the primer sequence can be compared to the sequences in the GEN-BANK™ database to determine if any significant matches occur. If the oligonucleotide sequence is present in any known DNA sequence or, more importantly, in any known repetitive elements, the primer sequence should be changed.

Detection of Alleles:

The nucleic acids obtained from the sample can be genotyped to identify the particular allele present for a marker locus. A sample of sufficient quantity to permit direct detection of marker alleles from the sample can be obtained from the subject. Alternatively, a smaller sample is obtained from the subject and the nucleic acids are amplified prior to detection. Any APOL1 nucleic acid that is informative for a SNP or inversion or chromosome haplotype can be detected. Generally, the target nucleic acid corresponds to a tag SNP described above (SEQ ID NOs: 1-3). Any method of detecting a nucleic acid molecule can be used, such as hybridization and/or sequencing assays.

Hybridization is the binding of complementary strands of DNA, DNA/RNA, or RNA. Hybridization can occur when primers or probes bind to target sequences such as target sequences within genomic DNA. Probes and primers that are useful generally include nucleic acid sequences that hybridize (for example under high stringency conditions) with a nucleic acid sequence including a SNP or inversion of interest, but do not hybridize to a reference allele, or that hybridize to the reference allele, but do not hybridize to the SNP or inversion. Physical methods of detecting hybridization or binding of complementary strands of nucleic acid molecules, include but are not limited to, such methods as DNase I or chemical footprinting, gel shift and affinity cleavage assays, Southern and Northern blotting, dot blotting and light absorption detection procedures. The binding between a nucleic acid primer or probe and its target nucleic acid is frequently characterized by the temperature ($T_m$) at which 50% of the nucleic acid probe is melted from its target. A higher ($T_m$) means a stronger or more stable complex relative to a complex with a lower ($T_m$).

Generally, complementary nucleic acids form a stable duplex or triplex when the strands bind, (hybridize), to each other by forming Watson-Crick, Hoogsteen or reverse Hoogsteen base pairs. Stable binding occurs when an oligonucleotide molecule remains detectably bound to a target nucleic acid sequence under the required conditions.

Complementarity is the degree to which bases in one nucleic acid strand base pair with the bases in a second nucleic acid strand. Complementarity is conveniently described by percentage, that is, the proportion of nucleotides that form base pairs between two strands or within a specific region or domain of two strands. For example, if 10 nucleotides of a 15-nucleotide oligonucleotide form base pairs with a targeted region of a DNA molecule, that oligonucleotide is said to have 66.67% complementarity to the region of DNA targeted.

In the present disclosure, "sufficient complementarity" means that a sufficient number of base pairs exist between an oligonucleotide molecule and a target nucleic acid sequence (such as a tag SNP) to achieve detectable and specific binding. When expressed or measured by percentage of base pairs formed, the percentage complementarity that fulfills this goal can range from as little as about 50% complementarity to full (100%) complementary. In general, sufficient complementarity is at least about 50%, for example at least about 75% complementarity, at least about 90% complementarity, at least about 95% complementarity, at least about 98% complementarity, or even at least about 100% complementarity. The qualitative and quantitative considerations involved in establishing binding conditions that allow one skilled in the art to design appropriate oligonucleotides for use under the desired conditions is provided by Beltz et al. *Methods Enzymol* 100:266-285, 1983, and by Sambrook et al. (ed.), *Molecular Cloning: A Laboratory Manual,* 2nd ed., vol. 1-3, Cold Spring Harbor Laboratory Press, Cold Spring Harbor, N.Y., 1989.

Hybridization conditions resulting in particular degrees of stringency will vary depending upon the nature of the hybridization method and the composition and length of the hybridizing nucleic acid sequences. Generally, the temperature of hybridization and the ionic strength (such as the Na$^+$ concentration) of the hybridization buffer will determine the stringency of hybridization. Calculations regarding hybridization conditions for attaining particular degrees of stringency are discussed in Sambrook et al., (1989) *Molecular*

*Cloning: A Laboratory Manual*, second edition, Cold Spring Harbor Laboratory, Plainview, N.Y. (chapters 9 and 11). Exemplary hybridization conditions are provided above.

Methods for labeling nucleic acid molecules so they can be detected are well known. Examples of such labels include non-radiolabels and radiolabels. Non-radiolabels include, but are not limited to an enzyme, chemiluminescent compound, fluorescent compound (such as FITC, Cy3, and Cy5), metal complex, hapten, enzyme, colorimetric agent, a dye, or combinations thereof. Radiolabels include, but are not limited to, $^{125}$I, $^{32}$P and $^{35}$S. For example, radioactive and fluorescent labeling methods, as well as other methods known in the art, are suitable for use with the present disclosure. In one example, primers used to amplify the subject's nucleic acids are labeled (such as with biotin, a radiolabel, or a fluorophore). In another example, amplified target nucleic acid samples are end-labeled to form labeled amplified material. For example, amplified nucleic acid molecules can be labeled by including labeled nucleotides in the amplification reactions.

Nucleic acid molecules corresponding to one or more APOL1 SNPs and/or inversions, or haplotypes blocks, including a tag SNP, can also be detected by hybridization procedures using a labeled nucleic acid probe, such as a probe that detects only one alternative allele at a marker locus. Most commonly, the target nucleic acid (or amplified target nucleic acid) is separated based on size or charge and transferred to a solid support. The solid support (such as membrane made of nylon or nitrocellulose) is contacted with a labeled nucleic acid probe, which hybridizes to it complementary target under suitable hybridization conditions to form a hybridization complex.

Hybridization conditions for a given combination of array and target material can be optimized routinely in an empirical manner close to the $T_m$ of the expected duplexes, thereby maximizing the discriminating power of the method. For example, the hybridization conditions can be selected to permit discrimination between matched and mismatched oligonucleotides. Hybridization conditions can be chosen to correspond to those known to be suitable in standard procedures for hybridization to filters (and optionally for hybridization to arrays). In particular, temperature is controlled to substantially eliminate formation of duplexes between sequences other than an exactly complementary allele of the selected marker. A variety of known hybridization solvents can be employed, the choice being dependent on considerations known to one of skill in the art (see U.S. Pat. No. 5,981,185).

Once the target nucleic acid molecules have been hybridized with the labeled probes, the presence of the hybridization complex can be analyzed, for example by detecting the complexes.

Methods for detecting hybridized nucleic acid complexes are well known in the art. In one example, detection includes detecting one or more labels present on the oligonucleotides, the target (e.g., amplified) sequences, or both. Detection can include treating the hybridized complex with a buffer and/or a conjugating solution to effect conjugation or coupling of the hybridized complex with the detection label, and treating the conjugated, hybridized complex with a detection reagent. In one example, the conjugating solution includes streptavidin alkaline phosphatase, avidin alkaline phosphatase, or horseradish peroxidase. Specific, non-limiting examples of conjugating solutions include streptavidin alkaline phosphatase, avidin alkaline phosphatase, or horseradish peroxidase. The conjugated, hybridized complex can be treated with a detection reagent. In one example, the detection reagent includes enzyme-labeled fluorescence reagents or calorimetric reagents. In one specific non-limiting example, the detection reagent is enzyme-labeled fluorescence reagent (ELF) from Molecular Probes, Inc. (Eugene, Oreg.). The hybridized complex can then be placed on a detection device, such as an ultraviolet (UV) transilluminator (manufactured by UVP, Inc. of Upland, Calif.). The signal is developed and the increased signal intensity can be recorded with a recording device, such as a charge coupled device (CCD) camera. In particular examples, these steps are not performed when radiolabels are used. In particular examples, the method further includes quantification, for instance by determining the amount of hybridization.

Allele Specific PCR:

Allele-specific PCR differentiates between target regions differing in the presence of absence of a variation or polymorphism. PCR amplification primers are chosen based upon their complementarity an APOL1 sequence, such as nucleic acid sequence in a SNP or inversion, haplotype block including a tag SNP, a specified region of an allele including a tag SNP, or to the tag SNP itself. The primers bind only to certain alleles of the target sequence. This method is described by Gibbs, *Nucleic Acid Res.* 17:12427 2448, 1989, herein incorporated by reference.

Allele Specific Oligonucleotide Screening Methods:

Further screening methods employ the allele-specific oligonucleotide (ASO) screening methods (e.g. see Saiki et al., *Nature* 324:163-166, 1986). Oligonucleotides with one or more base pair mismatches are generated for any particular allele or haplotype block. ASO screening methods detect mismatches between one allele (or haplotype block) in the target genomic or PCR amplified DNA and the other allele (or haplotype block), showing decreased binding of the oligonucleotide relative to the second allele (e.g., the other allele) oligonucleotide. Oligonucleotide probes can be designed that under low stringency will bind to both polymorphic forms of the allele, but which at high stringency, only bind to the allele to which they correspond. Alternatively, stringency conditions can be devised in which an essentially binary response is obtained. For example, an ASO corresponding to a variant form of the target gene will hybridize to that allele (haplotype block), and not to the reference allele (haplotype block).

Ligase Mediated Allele Detection Method:

Ligase can also be used to detect point mutations, such as the SNPs disclosed herein, in a ligation amplification reaction (e.g. as described in Wu et al., *Genomics* 4:560-569, 1989). The ligation amplification reaction (LAR) utilizes amplification of specific DNA sequence using sequential rounds of template dependent ligation (e.g., as described in Wu, supra, and Barany, *Proc. Nat. Acad. Sci.* 88:189-193, 1990).

Denaturing Gradient Gel Electrophoresis:

Amplification products generated using the polymerase chain reaction can be analyzed by the use of denaturing gradient gel electrophoresis. Different SNPs or alleles (haplotype blocks) can be identified based on the different sequence-dependent melting properties and electrophoretic migration of DNA in solution. DNA molecules melt in segments, termed melting domains, under conditions of increased temperature or denaturation. Each melting domain melts cooperatively at a distinct, base-specific melting temperature ($T_m$). Melting domains are at least 20 base pairs in length, and can be up to several hundred base pairs in length.

Differentiation between SNPs or alleles (haplotype blocks) based on sequence specific melting domain differences can be assessed using polyacrylamide gel electrophoresis, as described in Chapter 7 of Erlich, ed., *PCR Technology, Principles and Applications for DNA Amplification*, W. H. Freeman and Co., New York (1992).

Generally, a target region to be analyzed by denaturing gradient gel electrophoresis is amplified using PCR primers flanking the target region. The amplified PCR product is applied to a polyacrylamide gel with a linear denaturing gradient as described in Myers et al., *Meth. Enzymol.* 155:501-527, 1986, and Myers et al., in *Genomic Analysis, A Practical Approach*, K. Davies Ed. IRL Press Limited, Oxford, pp. 95 139, 1988. The electrophoresis system is maintained at a temperature slightly below the $T_m$ of the melting domains of the target sequences.

In an alternative method of denaturing gradient gel electrophoresis, the target sequences can be initially attached to a stretch of GC nucleotides, termed a GC clamp, as described in Chapter 7 of Erlich, supra. In one example, at least 80% of the nucleotides in the GC clamp are either guanine or cytosine. In another example, the GC clamp is at least 30 bases long. This method is particularly suited to target sequences with a high $T_m$.

Generally, the target region is amplified by polymerase chain reaction. One of the oligonucleotide PCR primers carries at its 5' end, the GC clamp region, at least 30 bases of the GC rich sequence, which is incorporated into the 5' end of the target region during amplification. The resulting amplified target region is run on an electrophoresis gel under denaturing gradient conditions. DNA fragments differing by a single base change will migrate through the gel to different positions, which can be visualized by ethidium bromide staining.

Temperature Gradient Gel Electrophoresis:

Temperature gradient gel electrophoresis (TGGE) is based on the same underlying principles as denaturing gradient gel electrophoresis, except the denaturing gradient is produced by differences in temperature instead of differences in the concentration of a chemical denaturant. Standard TGGE utilizes an electrophoresis apparatus with a temperature gradient running along the electrophoresis path. As samples migrate through a gel with a uniform concentration of a chemical denaturant, they encounter increasing temperatures. An alternative method of TGGE, temporal temperature gradient gel electrophoresis (TTGE or tTGGE) uses a steadily increasing temperature of the entire electrophoresis gel to achieve the same result. As the samples migrate through the gel the temperature of the entire gel increases, leading the samples to encounter increasing temperature as they migrate through the gel. Preparation of samples, including PCR amplification with incorporation of a GC clamp, and visualization of products are the same as for denaturing gradient gel electrophoresis.

Single-Strand Conformation Polymorphism Analysis:

Target sequences, such as alleles or haplotype blocks can be differentiated using single-strand conformation polymorphism analysis, which identifies base differences by alteration in electrophoretic migration of single stranded PCR products, for example as described in Orita et al., *Proc. Nat. Acad. Sci.* 85:2766-2770, 1989. Amplified PCR products can be generated as described above, and heated or otherwise denatured, to form single stranded amplification products. Single-stranded nucleic acids can refold or form secondary structures which are partially dependent on the base sequence. Thus, electrophoretic mobility of single-stranded amplification products can detect base-sequence difference between alleles or haplotype blocks.

Chemical or Enzymatic Cleavage of Mismatches:

Differences between target sequences, such as alleles or haplotype blocks, can also be detected by differential chemical cleavage of mismatched base pairs, for example as described in Grompe et al., *Am. J. Hum. Genet.* 48:212-222, 1991. In another method, differences between target sequences, such as alleles or haplotype blocks, can be detected by enzymatic cleavage of mismatched base pairs, as described in Nelson et al., *Nature Genetics* 4:11-18, 1993. Briefly, genetic material from an animal and an affected family member can be used to generate mismatch free heterohybrid DNA duplexes. As used herein, "heterohybrid" means a DNA duplex strand comprising one strand of DNA from one animal, and a second DNA strand from another animal, usually an animal differing in the phenotype for the trait of interest. Positive selection for heterohybrids free of mismatches allows determination of small insertions, deletions or other polymorphisms.

Non-Gel Systems:

Other possible techniques include non-gel systems such as TaqMan™ (Perkin Elmer). In this system oligonucleotide PCR primers are designed that flank the mutation in question and allow PCR amplification of the region. A third oligonucleotide probe is then designed to hybridize to the region containing the base subject to change between different alleles of the gene. This probe is labeled with fluorescent dyes at both the 5' and 3' ends. These dyes are chosen such that while in this proximity to each other the fluorescence of one of them is quenched by the other and cannot be detected. Extension by Taq DNA polymerase from the PCR primer positioned 5' on the template relative to the probe leads to the cleavage of the dye attached to the 5' end of the annealed probe through the 5' nuclease activity of the Taq DNA polymerase. This removes the quenching effect allowing detection of the fluorescence from the dye at the 3' end of the probe. The discrimination between different DNA sequences arises through the fact that if the hybridization of the probe to the template molecule is not complete (there is a mismatch of some form) the cleavage of the dye does not take place. Thus only if the nucleotide sequence of the oligonucleotide probe is completely complimentary to the template molecule to which it is bound will quenching be removed. A reaction mix can contain two different probe sequences each designed against different alleles that might be present thus allowing the detection of both alleles in one reaction.

Non-PCR Based Allele Detection:

The identification of a DNA sequence can be made without an amplification step, based on polymorphisms including restriction fragment length polymorphisms in a subject and a control, such as a family member. Hybridization probes are generally oligonucleotides which bind through complementary base pairing to all or part of a target nucleic acid. Probes typically bind target sequences lacking complete complementarity with the probe sequence depending on the stringency of the hybridization conditions. The probes can be labeled directly or indirectly, such that by assaying for the presence or absence of the probe, one can detect the presence or absence of the target sequence. Direct labeling methods include radioisotope labeling, such as with $^{32}P$ or $^{35}S$. Indirect labeling methods include fluorescent tags, biotin complexes which can be bound to avidin or streptavidin, or peptide or protein tags. Visual detection methods include photoluminescents, Texas red, rhodamine and its derivatives, red leuco dye and 3,3',5,5'-tetramethylbenzidine (TMB), fluorescein, and its derivatives, dansyl, umbelliferone and the like or with horse radish peroxidase, alkaline phosphatase and the like.

Hybridization probes include any nucleotide sequence capable of hybridizing to a nucleic acid sequence wherein a polymorphism is present that is associated with FSGS or hypertensive ESKD, such as an APOL1 SNP and/or inversion, or a tag SNP, and thus defining a genetic marker, including a restriction fragment length polymorphism, a hypervariable region, repetitive element, or a variable number tandem repeat. Hybridization probes can be any gene or a suitable analog. Further suitable hybridization probes include exon fragments or portions of cDNAs or genes known to map to the relevant region of the chromosome.

Exemplary tandem repeat hybridization probes for use in the methods disclosed are those that recognize a small number of fragments at a specific locus at high stringency hybridization conditions, or that recognize a larger number of fragments at that locus when the stringency conditions are lowered.

The disclosure is illustrated by the following non-limiting Examples.

EXAMPLES

Example 1

APOL1 Variants Associated with Focal Segmental Glomerulosclerosis

Methods

FSGS Genotype Experiment:

Variants for the initial FSGS genotype study were selected by accessing 1000 Genomes Project (1000genomes.org/) data using the Integrative Genomics Viewer (broadinstitute.org/igv). All variants in the region 34,930 kb-35,060 kb (NCBI 36) with estimated minor allele frequency greater than 15% in Yoruba and minor allele frequency less than 10% in Europeans were selected, together with some additional ones with biological relevance, and sent for genotyping using Sequenom technology (sequenom.com). A small amount of SNPs were dropped due to Multiple eXTEND hits for scanned primer triplets and some failed genotyping (<20%). Overall three plexes were used for the FSGS analysis. Association of genotype data and association controlling for allelles G1 and G2 were performed with plink (pngu.mgh.harvard.edut~purcell/plink; Purcell et al., Am. J. Hum. Genet. 81:559-575, 2007) using Fisher's exact test and logistic regression.

Bounds on Causal Variant(s):

Due to the high frequency differentiation between frequency of alleles G1 and G2 in cases and controls, some formal arguments can be made to discard other variants as causal. Define with $A_1$ the combined allele G1 and G2 and with $A_2$ the wild type allele. Define with $B_1$ the risk version of the combined causal alleles and with $B_2$ the non-risk version. Assume that in controls the frequency of haplotype $A_1B_1$ is $x_{11}$, $A_1B_2$ is $x_{12}$, $A_2B_1$ is $x_{21}$, and $A_2B_2$ is $x_{22}$. Define the frequency in controls of allele $A_1$ as $p_1=x_{11}+x_{12}$, and $B_1$ as $q_1=x_{11}+x_{21}$. Say $p'_1$ and $q'_1$ for the frequencies of $A_1$ and $B_1$ in cases with $p'_1>p_1$ and $q'_1>q_1$. Think of $x_{11}/q_1$ as the fraction of haplotypes containing $B_1$ which also contain $A_1$ and $x_{12}/(1-q_1)$ as the fraction of haplotypes containing $B_2$ which also contain $A_1$. We can then write:

$$p_1=(x_{11}/q_1)q_1+x_{12}/(1-q_1)(1-q_1),$$

$$p'_1=(x_{11}/q_1)q'_1+x_{12}/(1-q_1)(1-q_1).$$

By subtracting one equation from the other:

$$p'_1-p_1=x_{11}/q_1(q'_1+q_1)°x_{12}/(1-q_1)(1-q'_1-1+q_1),$$

$$p'_1-p_1=(x_{11}/q_1-x_{12}/(1-q_1))(q'_1-q_1).$$

From this equation, since $q'_1<1$ and $x_{11}<p_1$, we get the inequality:

$$p'_1-p_1<p_1/q_1(1-q_1),$$

$$q_1<p_1/p'_1.$$

In the NIH FSGS cohort, $p_1=33\%$ and $p'_1=72\%$, from which we get the bound $q_1<46\%$. The rationale behind this argument is that if the frequency of the causal allele is too high in controls, then even if it was 100% in cases, this difference would not be able to explain the disparity observed for alleles in APOL1.

Continuing from the previous equation:

$$p'_1-p_1=(x_{11}-x_{11}q_1-x_{12}q_1)/(q_1(1-q_1))(q'_1-q_1).$$

Dividing both sides by \sqrt($p_1(1-p_1)$) we get:

$$(p'_1-p_1)/\sqrt(p_1(1-p_1))=(x_{11}-p_1q_1)/(\sqrt(p_1(1-p_1)q_1(1-q_1))(q'_1-q_1)/\sqrt(q_1(1-q_1)).$$

Define r as the correlation coefficient between the combined allele G1 and G2 and the combined causal alleles. By the definition of correlation coefficient, the previous equation can be written as:

$$(p'_1-p_1)/\sqrt(p_1(1-p_1))=r(q'_1-q_1)/\sqrt(q_1(1-q_1)),$$

$$r=(p'_1-p_1)/\sqrt(p_1(1-p_1))\sqrt(q_1(1-q_1))/(q'_1-q_1).$$

Given that $q'_1-q_1<1-q_1$, $$r>(p'_1-p_1)/\sqrt(p_1(1-p_1))\sqrt(q_1/(1-q_1)),$$

$$r^2>(p'_1-p_1)^2/(p_1(1-p_1))q_1/(1-q_1).$$

In the NIH FSGS cohort, $p_1=33\%$ and $p'_1=72\%$. If we assume that $q_1>30\%$, we get an estimate $r^2>29\%$, that could be only explained by a short distance between the two variants.

Results

More than 50 genetic variants spanning the region including APOL1, without bias towards either gene were selected for fine mapping. Because the kidney disease risk allele(s) should have a high frequency in African-Americans, as suggested by previous studies (Kopp et al., Nature Genet. 40:1175-1184, 2008; Kao et al., Nature Genet. 40:1185-1192, 2008), causal alleles should be present in the sequence data of Africans available from the 1000 Genomes Project (available on the web at 1000genomes.org). The data was searched for variants that were highly polymorphic in Yoruba that were rare or absent in Europeans, as disease-causing variants are expected to have this property. In addition, a single 6 bp deletion (rs71785313) in the coding region of APOL1 also identified by the 1000 Genomes Project that was observed in three of the Yoruba samples was studied. Many of these variants have not been genotyped by the HapMap project.

An association analysis was performed with each of these variants and disease, using DNA from 205 African-Americans with biopsy proven FSGS and no family history of FSGS and 180 African-American controls. Association between disease and each variant showed that the strongest associations were all clustered in a 10 kb region centered on the last exon of APOL1 (Table 3). These findings are summarized in FIG. 1A. The strongest association was obtained for the haplotype termed "G1" consisting of the two derived alleles for rs73885319 (S342G) and rs60910145 (I384M), in the last exon of APOL1. These two alleles were found to be in perfect linkage disequilibrium (LD) ($r^2=1$).

The G1 compound allele (342G:384M) had a frequency of 52% in the combined set of FSGS cases and 18% in controls (Table 4).

Figure 1B:
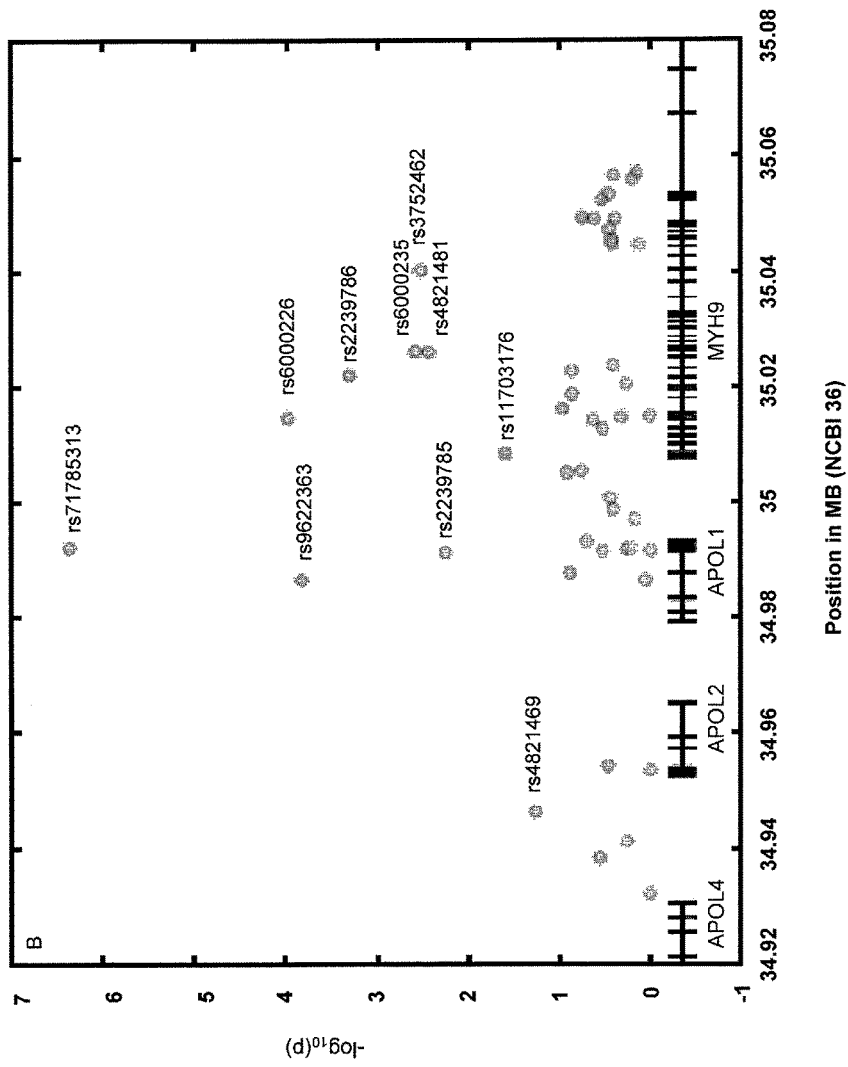

When logistic regression controlling for rs73885319 was performed, a second strong signal was detected for a 6 bp deletion termed "G2" recently entered into dbSNP as rs71785313 (−/TTATAA; SEQ ID NO: 6) that removes amino acids N388 and Y389 (Table 5). Due to the extremely close proximity of rs73885319, rs60910145, and rs71785313, the two alleles G1 and G2 are mutually exclusive, as recombination between them is very unlikely. FIG. 1B highlights variants which still showed statistically significant associations. These results are in accordance with recent studies (Freedman et al., *Kidney Int.* 75:736, 2009; Nelson et al., *Hum. Mol. Genet.* 19:1805-1815, 2010; Behar et al., *Hum. Mol. Genet.* 19:1816-1827, 2010), which also identified multiple different independent signals of association. Allele G2 had a frequency of 23% in the combined set of cases and 15% in the controls (Table 4).

Among the FSGS cases, all proven by kidney biopsy, 53 individuals were recruited through the Brigham and Women's Hospital (BWH) from medical centers in the northeastern United States, and 152 individuals were recruited in the US National Institutes of Health (NIH) FSGS Genetic Study from 22 academic medical centers in the United States (MacKenzie et al., *J. Am. Soc. Nephrol.* 18:2987, 2007; Orloff et al., *Physiol. Genom.* 21:212, 2005). As controls, DNA from 180 individuals from the NIH Blood Bank and the National Cancer Institute-Frederick normal donor programs were used.

Odds ratios for disease were computed using the NIH samples, as these samples were the best matched geographically. Table 6 shows the count for each one of the six possible compound genotypes observable in each cohort of cases and controls. By combining the two risk alleles G1 and G2, a $\chi^2$ squared test showed no association with FSGS between samples with no risk alleles and one risk alleles (p=0.81). This supports a completely recessive model. A second analysis comparing samples with one or no risk alleles and samples with two risk alleles provided an odds ratio for FSGS of 10.5 (CI 6.0-18.4).

When comparing the number of samples with two risk alleles among the BWH cases and the NIH cases, as shown in Table 3, significant statistical differences were observed among frequencies of alleles G1 and G2 using a Fisher's exact test (p=0.04). This disparity cannot be explained by a difference in the amount of African ancestry, as presence of risk alleles implies African ancestry at the relevant locus, but may simply reflect a difference in the frequency of allele G1 in the north eastern United States.

Example 2

Replication in Hypertension-Attributed EKSD

Methods

Selection criteria for controls and hypertension-attributed ESKD cases are described in detail in Freedman et al. (*Kidney Int.* 75:736, 2009). Briefly, self-reported African-Americans from North Carolina, South Carolina, Georgia, Virginia, or Tennessee were recruited. Hypertension-attributed ESKD cases were diagnosed with hypertension prior to initiation of renal replacement therapy, and demonstrated hypertensive target end-organ damage (retinopathy or left ventricular hypertrophy) and low grade or absence of proteinuria. Only a minority of cases had quantified urinary protein excretion. Patients with diabetic (type 1 and 2) ESKD were excluded, as were known cases of cystic kidney disease, hereditary nephritis, and urologic causes of ESKD.

Geographically similar controls all denied a history of kidney disease and diabetes, or first-degree relatives with these diseases. Most controls did not have direct measurements of arterial blood pressure or renal function indices. Consequently, some controls may have had occult kidney disease, which would underestimate the effect size between cases and controls.

Results

Association of APOL1 variants and renal disease was tested in a much larger cohort of 1030 African-American cases with putative hypertensive ESKD and 1025 geographically matched African-American controls from Wake Forest University. In this cohort 36 variants were investigated that were chosen based on strongest signals of positive selection in a broader region, nearby coding variants together with rs73885319 (G1) and rs71785313 (G2). The strongest association found was again for rs73885319 (p=1.1×10$^{-39}$, Table 7). Upon controlling for rs73885319, the strongest association was again for rs71785313 (p=8.8×10$^{-18}$, Table 8). Frequencies for these alleles are shown in Table 3.

With this larger population the mode of inheritance of G1 and G2 was explored. Cases and controls were partitioned into the six possible genotypes. One risk allele was associated with only a small increase in renal disease risk (odds ratio 1.26, CI 1.01-1.56, p=0.047). Two risk alleles versus zero risk alleles yielded an odds ratio of 7.3 (CI 5.6-9.5). Two risk alleles versus one risk allele gave an odds ratio of 5.8 (CI 4.5-7.5). Overall, a recessive model best explains these findings and is in agreement with the analysis of FSGS samples.

Example 3

Evidence of Natural Selection

Methods

Test for Genetic Divergence in African Populations:

To test for statistically significant differentiation of allele frequency in between two populations we assume that the difference in frequencies for a given polymorphism has mean 0 and variance cp(1−p), where p is the ancestral frequency and c=2×$F_{ST}$ (Ayodo et al., *Am. J. Hum. Genet.* 81:234-242. 2007). Given the small size of the samples in the two populations analyzed, it is also important to model sampling noise, which has variance p(1−p)(1/$N_1$+$N_2$), where $N_1$ and $N_2$ are the total count for the alleles for the two populations. Therefore, to test for differentiation of frequency at a given allele, we model the difference as a normal random variable with mean 0 and variance p(1−p)(c+1/$N_1$+1/$N_2$) and we compute for each allele a $\chi^2$ statistic with 1 df.

Estimation of the Age of the Selected Allele:

Because of the presence of a recombination hotspot in between APOL1 and MYH9 (Frazer et al., *Nature* 449:851-861, 2007), SNP rs11912763, the variant most correlated with G1 available in Hapmap, has genetic distance of about 0.2 centimorgans from APOL1 cSNPs rs73885319 and rs60910145, despite a physical distance of less than 25 kb from APOL1. The derived allele for SNP rs11912763, absent outside of Africa, has a prevalence of about p=73% in haplotypes containing the G1 allele. If we assume that the G1 allele arose in a haplotype already containing the rs11912763 derived allele, then the prevalence of the derived allele for rs11912763 in haplotypes containing the G1 allele could not have decreased at a rate faster than the expected frequency of recombination 1−c per generation. This leads to an estimate for the number t of generations $(1-c)^t \leq p$, $t \geq \log(p)/\log(1-c)$, from which we obtain a lower bound of about 150 generations, using the values for c and p as above. If we assume an average of 20 years per generation, this estimate suggests an age of at least 3,000 years for allele G1. Given the prevalence of about p=72% for the rs2239786 derived allele in haplotypes containing the G2 allele, a similar estimate also holds for the age of allele G2.

Results

Figure 2:
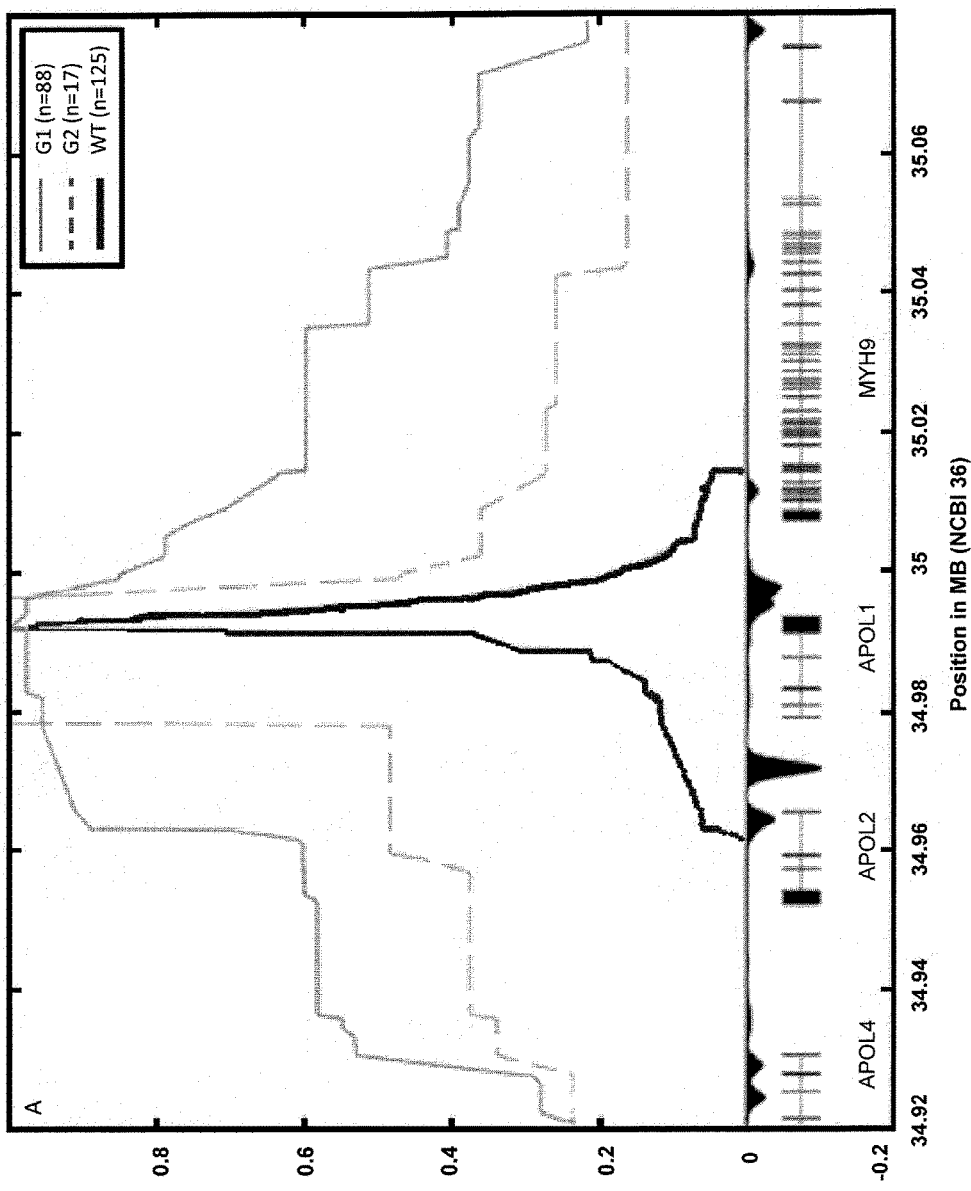
FIG. 2 is a graph showing extended haplotype homozygosity (EHH) values for the three APOL1 alleles computed after combining Hapmap phase 2 genotype data with genotype data for alleles G1 and G2 for Yoruba samples. This suggests an older age for allele G2, although large uncertainty is introduced by the fact that only 8 haplotypes with the G2 allele were found in the Yoruba sample set.

The chromosomal region where APOL1 resides has previously been shown to be a candidate for positive selection in the Yoruba population using the long-range haplotype method (LRH) (Frazer et al., *Nature* 449:851-861, 2007), the integrated haplotype score (iHS) (Voight et al., *PLoS Biol.* 4:446, 2006; Barreiro et al., *Nature Genet.* 40:340-345, 2008), the rMHH (Kimura et al., *PLoS One* 2:e286, 2007), and the composite of multiple signals (CMS) (Grossman et al., *Science* 327:883, 2010). The G1 and G2 allele was present in all the Yoruba Hapmap samples and the extended haplotype homozygosity (EHH) (Sabeti et al., *Nature* 419: 832-837, 2002) was computed for each one of the three alleles after phasing the data using Beagle (Browning and Browning, *Am. J. Hum. Genet.* 84:210-223, 2009) (FIG. 2). The iHS score was not computed, as the proximity of a recombination hotspot makes this particular computation unstable.

The frequency of allele G1 was also compared in Yoruba samples from Nigeria and Luhya samples from Kenya to verify statistically significant differences in these two populations. The Yoruba population from Nigeria (YRI) and the Luhya population from Kenya (LWK), despite being respectively from West Africa and East Africa, are very closely related genetically with $F_{ST}=0.0043$. To test for selection, a model of allele-frequency differentiation between two populations was used (Ayodo et al., *Am. J. Hum. Genet.* 81:234-242. 2007), which corrects for genetic drift. The results showed that differentiation for rs73885319, whose frequencies are 38% in the Yoruba and 5% in the Luhya, is highly significant ($F_{ST}=0.16$ and $p-3.53 \times 10^{-9}$). Interestingly, variant rs73885319 was the second most highly differentiated variant in these two populations across the whole genome. The frequencies of variant rs71785313, respectively 0.08 and 0.07, did not show any significant differentiation. Results of this analysis for the region in between 34,900 kb and 35,100 kb (NCBI 36) are shown in Table 9.

By analyzing the pattern of linkage disequilibrium between these SNPs, it appears likely that alleles G1 and G2 are at least 3,000 years old. The true age is likely older than this number, but not by orders of magnitude, and it might coincide with the Bantu expansion event, a series of migrations across sub-Saharan Africa that is estimated to have taken place between 4,500 and 5,000 years ago (Excoffier et al., *Am. J. Phys. Anthropol.* 30:151-194, 2005). In particular, frequency differentiation of allele G1 between two populations from West and East Africa points to natural selection having acted after the Bantu expansion, either to raise the frequency in Yoruba or to decrease the frequency in Luhya.

Example 4

APOL1 and Resistance Against Trypanosome

Methods

Expression of ApoL1 Proteins:

Two independent systems were used for expression of recombinant ApoL1 in *Escherichia coli* and in 293T cells. The various ApoL1 mutants were generated by site-directed mutagenesis and expressed in *E. coli* essentially as described in Lecordier et al. (*PLoS Pathog.* 5:e1000685, 2009), except that the pStaby1.2 plasmid (Delphi Genetics, Gosselies, Belgium) was used. For production of ApoL1 protein in 293T cells with and without the G1 and G2 risk mutations, an image clone containing the ApoL1 cDNA lacking the G1 and G2 mutations (reference sequence BC141823) was purchased from Open Biosystems (Huntsville, Ala.). This cDNA was provided in the pCMV-SPORT6 expression vector. The G1 and G2 mutations were introduced by synthesis of cDNA minigene fragments (Integrated DNA Technologies, Coralville, Iowa) containing the corresponding mutations flanked with 5' AleI and 3' XbaI restriction sequences. The minigene fragments were then cloned into the parental vector replacing the sequence between the AleI and XbaI restriction sites. The resultant vectors were used to transfect 293T cells using Fugene (Promega, Madison, Wis.). The transfection media was replaced with OPTI-MEM reduced serum media without phenol red (Life Technologies/Invitrogen, Carlsbad, Calif.) at 12 hours post transfection. At 72 hours post transfection the supernatants were harvested and concentrated 100 fold using an Amicon Ultracel—10K centrifugal filter unit (Millipore, Billerica, Mass.). The media was exchanged by centrifugation within the Ultracel filters with fresh Iscove's Modified Dulbecco's Medium for compatibility with the trypanosome killing assay.

Trypanolytic Assays:

The evaluation of trypanolytic activity of the various ApoL1 mutants was performed as described in Lecordier et al. (*PLoS Pathog.* 5:e1000685, 2009).

Results

ApoL1 is the trypanolytic factor of human serum (Vanhamme et al., *Nature* 422:83-87, 2003; Perez-Morga et al., *Science* 309:469, 2005) and confers resistance to the *Trypanosoma brucei brucei* parasite. *T. b. brucei* has evolved into two forms, *Trypanosoma brucei gambiense* and *Trypanosoma brucei rhodesiense* (Gibson *Parasitol. Today* 9:255-257, 1986; Gibson *Trends Parasitol.* 18:486-490, 2002) which have both acquired the ability to infect humans. FIGS. 3A and B show the relative distribution of infections by *T. b. rhodesiense* and *T. b. gambiense*. Since these parasites exist only in sub-Saharan Africa, it is plausible that the APOL1 gene had undergone natural selective pressure to counteract the trypanosome adaptations.

*T. b. rhodesiense* can grow in humans because of a serum resistance-associated (SRA) protein that interacts with the C-terminal helix of ApoL1 and inhibits its anti-trypanosomal activity (Xong et al., *Cell* 6:839-846, 1998; Vanhamme et al., *Nature* 422:83-87, 2003). A recent study showed that mutations and deletions engineered into this helix prevent SRA from binding to ApoL1 (Lecordier et al., *PLoS Pathog.* 5:e1000685, 2009). The 6 bp deletion rs71785313 defining the G2 allele is located exactly at the SRA binding site in the ApoL1 C-terminal helix.

Figure 4:
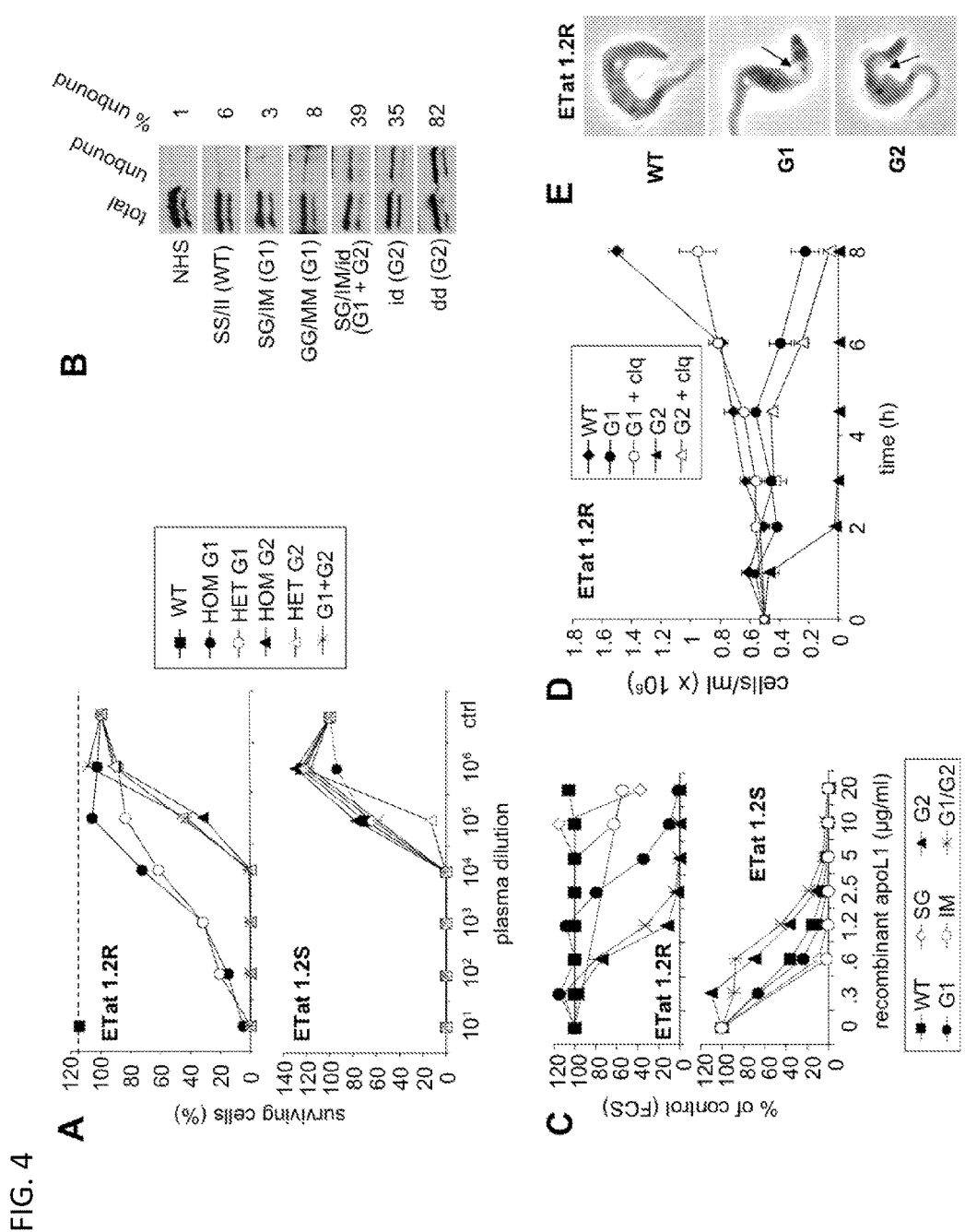
FIG. 4 is a series of panels showing trypanolytic potential of ApoL1 variants on NHS-resistant (SRA+) and NHS-sensitive (SRA−) *T. b. rhodesiense* ETat 1.2 (Edinburgh Trypanozoon antigenic type 1, clone 2) clones. (A) Titration of trypanolytic activity in plasma samples after overnight incubation (ctrl=control incubation in fetal calf serum without plasma; hom, het=homozygous and heterozygous mutations, respectively). (B) ApoL1 content of various plasma samples before and after affinity chromatography through SRA column (NHS=normal human serum; WT=wild type apoL1; S=serine 342; G=glycine 342; I=isoleucine 384; M=methionine 384; i=insertion of N388/Y389; d=deletion of N388/Y389). (C) Trypanolytic activity of various recombinant ApoL1 variants after overnight incubation (FCS=fetal calf serum). (D) Kinetics of trypanolysis by 20 μg/ml recombinant ApoL1 variants in the presence or absence of 25 μM chloroquine (clq). (E) Phenotype of ETat1.2R trypanosomes incubated with various recombinant ApoL1 (20 μg/ml; 1 h30 and 6 h incubation, for G1 and G2 respectively; the arrows point to the swelling lysosome).

Analysis of the in vitro lytic potential of 77 human plasma samples was conducted on *T. b. brucei*, *T. b. rhodesiense*, and *T. b. gambiense*. While all samples efficiently lysed *T. b. brucei*, none lysed *T. b. gambiense* and 46 lysed normal human serum (NHS)-resistant *T. b. rhodesiense* clones. All *T. b. rhodesiense* lytic samples belonged to G1, G2 or both genotypes. As measured by titration upon serial dilution, the lytic potential of these plasmas against NHS-resistant (SRA+) *T. b. rhodesiense* was higher for G2 than for G1, whereas it was similar for both genotypes against NHS-sensitive (SRA−) parasites (FIG. 4A). While lysis of *T. b. rhodesiense* by G2 could be explained by the incapacity of this mutant ApoL1 to bind SRA, this conclusion did not hold for G1 plasmas, where ApoL1 still efficiently bound to SRA (FIG. 4B).

These results were confirmed with recombinant ApoL1 proteins. The S342G/I384M (G1) and delN388/Y389 (G2) variants killed both NHS-sensitive (SRA−) and NHS-resistant (SRA+) *T. b. rhodesiense* parasites (FIG. 4C), but not *T. b. gambiense*. While G2 was more active than G1 on NHS-resistant *T. b. rhodesiense*, the reverse was true on NHS-sensitive parasites. ApoL1 variants with either S342G or I384M alone were less lytic against *T. b. rhodesiense* than was the combination of the two mutations, whereas the S342G/I384M/delN388/Y389 variant was not more active than delN388/Y389 alone (FIG. 4C). As shown in FIGS. 4D and E, all measured features of the *T. b. rhodesiense* lysis process (kinetics, transient inhibition by chloroquine, typical swelling of the lysosome) were similar to those observed on *T. b. brucei* with either NHS or recombinant ApoL1 (Perez-Morga et al., *Science* 309:469-472, 2005). Therefore, deletion of N388/Y389 was necessary and sufficient to prevent interaction with SRA and to allow ApoL1 to kill *T. b. rhodesiense*, whereas the combination of S342G and I384M was required for maximal ability to kill *T. b. rhodesiense* despite the binding of SRA. None of these mutations affected the resistance of *T. b. gambiense*.

Example 5

Predictive Power of APOL1 SNPs

HIV negative individuals carrying one APOL1 risk allele at rs73885319 and one APOL1 risk allele at rs71785313 have a predicted 4.3 fold increase in risk of FSGS over the (African American) population average. 40% of these individuals have a predicted 1.6 fold increased, while the remaining 60% have a predicted 5.6 fold predicted risk; the individuals receiving an exaggerated prediction of risk represent 22 out of 1000 individuals tested. Similar although smaller improvements in risk estimates occur for other APOL1 risk strata.

The ROC C statistic was calculated for FSGS. For FSGS, the C statistic for at least one APOL1 risk allele was 0.822. In HIV positive individuals, the C statistic for FSGS for at least one APOL1 risk allele was 0.865. This increase in the C statistic represents a 3% reduction in residual ignorance of FSGS risk.

Example 6

Nucleic Acid-Based Analysis of Genetic Predisposition to Renal Disease

The methods disclosed herein are used for evaluating if a subject has or is at risk for developing renal disease. For example, the methods can be used to determine if a subject is at risk for FSGS, or is at risk for hypertensive ESKD. One skilled in the art will appreciate that methods that deviate from these specific methods can also be used to successfully determine if a subject is at risk for renal disease.

In one example, a sample including nucleic acids can be obtained from a subject who is suspected to have a genetic predisposition to renal disease, such as FSGS or hypertensive ESKD. The subject can have family members who have had FSGS or hypertensive renal disease. In another example, a sample including nucleic acids can be obtained from a subject that is of African ancestry. In a further example, a sample including nucleic acids is obtained from a subject with African (such as African-American) ancestry who is infected with HIV.

In a further example, a sample including nucleic acids is obtained from a subject who has renal disease, wherein it is of interest to determine if the subject has hypertensive ESKD. For example, a sample can be obtained from a subject who presents with a reduced glomerular filtration rate (GFR) or other laboratory evidence of renal impairment (such as elevated blood urea nitrogen (BUN) or abnormal renal histology), or someone with the clinical presentation (symptoms) of renal disease, such as fatigue and liquid retention. Additional indicators of renal disease that can suggest chronic renal failure include hyperkalemia, acidemia, elevated serum creatinine levels and/or the uremic syndrome. A renal biopsy can be obtained from the subject to determine if the subject has FSGS or hypertensive nephrosclerosis.

In some particular embodiments of the method, the subject is seropositive for the HIV virus, and the test is performed to predict whether the subject is likely to develop renal disease, such as chronic renal failure, such as renal failure caused by FSGS. In other embodiments, the subject is someone who has clinical and laboratory evidence of early renal disease and the genetic test is performed to confirm the diagnosis of renal disease. For example, the subject may be an African-American with clinical evidence of early renal failure without a known etiology. Alternatively, the subject may have had a renal biopsy performed with inconclusive or ambiguous results. In these instances, the genetic test is performed to arrive at a diagnosis of chronic renal disease (or FSGS) with a higher degree of clinical certainty than would otherwise be possible. The genetic test can be used in association with other clinical signs and symptoms to assign a diagnosis, and from the diagnosis greater prognostic certainty can be provided to the subject. Alternatively, the genetic test can be used to provide a more specific diagnosis or etiology for chronic renal failure, as may be needed in research studies or for the selection of an appropriate therapeutic regimen.

In some examples a sample including nucleic acids is obtained from a subject with lupus nephritis or sickle cell anemia. These subjects can be tested to determine their haplotype at the time of diagnosis. In other examples a sample including nucleic acids is obtained from a subject with diabetes mellitus (type 1 or type 2), IgA nephropathy, and/or renal vasculitis.

The finding of a susceptibility haplotype can initiate screening annually or biannually for protein, using albumin/creatinine ratio, such as beginning at about age 12 or about age 15. For example, subjects who are found to have a condition that is associated with renal injury, including prematurity, small birth weight, obesity, hypertension, systemic lupus erythematosus, sickle cell anemia, diabetes mellitus, and HIV-1 infection can be screened using the methods disclosed herein.

To perform the method, a biological sample of the subject is assayed. The sample can, for example, be a blood sample or a buccal sample. Methods of isolating nucleic acid molecules from a biological sample are routine, for example using a commercially available kit to isolate DNA. Nucleic acid molecules isolated from PBMCs or any other biological sample can be amplified (for example, by PCR) using routine methods to form nucleic acid amplification products.

It is determined if the individual has an APOL1 SNP (such as a G at rs73885319, a G at rs60910145, and/or a 6 base pair deletion at rs71785313) using standard methods, such as real-time PCR (for example, a TAQMAN® assay), allele-specific PCR, or sequence analysis. The presence of at least one APOL1 SNP indicates that the subject is at risk for developing renal disease. For example, the methods can be used to determine if a subject is at risk for FSGS, or is at risk for hypertensive ESKD.

Thus, in some cases, it is determined if the individual has an APOL1 SNP (such as a G at rs73885319, a G at rs60910145, and/or a 6 base pair deletion at rs71785313) using standard methods, such as real-time PCR (for example, a TAQMAN® assay), allele-specific PCR, or sequence analysis. The presence of at least one APOL1 SNP indicates that the subject is at risk for developing renal disease. For example, the methods can be used to determine if a subject is at risk for FSGS, or is at risk for hypertensive ESKD.

In another embodiment, the methods can be used to identify protective alleles in a subject that are associated with the absence of renal disease. In this instance, the detection of protective alleles in a biological sample may be indicative of a lower risk for developing renal disease in the subject.

Example 7

Nucleic Acid-Based Analysis of Resistance to *Trypanosoma*

The methods disclosed herein are used for evaluating if a subject has a resistance to disease associated with *Trypanosoma* infection. For example, the methods can be used to determine if a subject has resistance to African trypanosomiasis (sleeping sickness) caused by *T. brucei*. One skilled in the art will appreciate that methods that deviate from these specific methods can also be used to successfully determine if a subject has a resistance to disease associated with *Trypanosoma* infection.

In one example, a sample including nucleic acids can be obtained from a subject who is suspected to be at risk for disease associated with *Trypanosoma* infection. The subject can live in, have traveled to, or plan to travel to an area where *Trypanosoma* parasites are endemic, for example, sub-Saharan Africa.

To perform the method, a biological sample of the subject is assayed. The sample can, for example, be a blood sample or a buccal sample. Methods of isolating nucleic acid molecules from a biological sample are routine, for example using a commercially available kit to isolate DNA. Nucleic acid molecules isolated from PBMCs or any other biological sample can be amplified (for example, by PCR) using routine methods to form nucleic acid amplification products.

It is determined if the individual has an APOL1 SNP (such as a G at rs73885319, a G at rs60910145, and/or a 6 base pair deletion at rs71785313) using standard methods, such as real-time PCR (for example, a TAQMAN® assay), allele-specific PCR, or sequence analysis. The presence of at least one APOL1 SNP indicates that the subject has a resistance to disease associated with *Trypanosoma* infection. For example, the methods can be used to determine if a subject is has resistance to disease associated with infection with *T. brucei*.

In another embodiment, the methods can be used to identify APOL1 SNPs (such as an A at rs73885319, a T at rs60910145, and absence of a 6 base pair deletion at rs71785313) in a subject that are associated with decreased resistance or susceptibility to disease associated with *Trypanosoma* infection. In this instance, the detection of these SNPs in a biological sample may be indicative of decreased resistance or increased susceptibility of the subject to disease associated with *Trypanosoma* infection.

Example 8

Genetic Variation in APOL1 and Age at Hemodialysis Initiation in African Americans African Americans have a markedly higher incidence of end-stage renal disease (ESRD) compared with other racial groups. Two coding sequence risk alleles in the APOL1 gene, found only in individuals of recent African ancestry, have been identified as risk alleles for renal disease in African Americans. We tested whether these risk alleles were also linked to age of initiation of chronic hemodialysis.

Methods:

We performed a cross-sectional study of 407 non-diabetic African-Americans with ESRD who participated in Accelerated Mortality on Renal Replacement (ArMORR), a prospective cohort study of incident chronic hemodialysis subjects from across the United States. We examined age of initiation of chronic hemodialysis according to APOL1 risk alleles (G1 and G2). Analysis of variance was used to compare mean age at dialysis initiation, and multivariate linear regression modeling was used to adjust for potential confounders.

Results:

African American subjects carrying two copies of the G1 risk allele initiated chronic hemodialysis at a mean age of 49.0±14.9 years, significantly earlier than subjects with one copy of the G1 allele (55.9±16.7 years: p=0.014) or those without any risk allele (61.8±17.1 years; p=6.2×10$^{-7}$). The G1 relationships remained statistically significant in multivariate analysis adjusting for socio-demographic and other potential confounders. G2 risk allele was not linked to age of chronic hemodialysis initiation; however, limited sample size in this analysis precluded definitive conclusions.

Conclusion:

Genetic variations in the APOL1 gene identify African Americans that initiate chronic hemodialysis at an earlier age. Early interventions to prevent progression of kidney disease may benefit this high-risk population.

Introduction

African Americans have a four-fold greater risk of end stage renal disease (ESRD) compared with white Americans (Klag et al., *JAMA* 277:1293-1298, 1997; System, *N.I.o. D.a.D.a.K.D.* National Institutes of Health, Editorial, 2010). In 2009, the mean age for African Americans at the start of renal replacement treatment was 59.2 years, compared with 66.8 years in Caucasians (System, supra). This may be due in part to an accelerated progression of renal disease in African Americans (Hsu et al., *J. Am. Soc. Nephrol.* 14:2902-2907, 2003; Walker et al., *JAMA* 268:3085-3091, 1992; Derose et al., *Kidney Int.* 76:329-637). Several studies have found that the high prevalence of ESRD in African Americans cannot be fully explained by socioeconomic differences or differences in access to medical care (Klag et al., supra; Tarver-Carr et al., *J. Am. Soc. Nephrol.* 13:2363-2370, 2002). Thus, it is thought that biologic factors, such as genetic differences, contribute to this disparity. Indeed, previous studies have demonstrated strong familial aggregation of kidney disease in African Americans (Freedman et al., *J. Am. Soc. Nephrol.* 8:1942-1945, 1997). Two recent studies used genetic admixture mapping to identify a region of chromosome 22 that explained the increased kidney disease risk in African Americans (Kao et al., *Nat. Genet.* 40:1185-1192, 2008; Genovese et al., *Science* 329:841-845, 2010).

Genovese et al. identified sequence variants in apolipoprotein L-1 (APOL1) as risk alleles for focal segmental glomerulosclerosis (FSGS) and hypertension-attributed ESRD (H-ESKD) in African Americans (Genovese et al., *Science*, supra; Genovese et al., *Kidney Int.* 78:698-704, 2010). APOL1 is located adjacent to the MYH9 gene on chromosome 22, a locus that has previously been reported to explain the high risk of renal disease in African Americans (Kao et al., supra). Interestingly, APOL1 risk proteins have lytic activity against a subspecies of trypanosomes known to cause African sleeping sickness. Carrier status may have provided a selective evolutionary advantage and thus maintained these risk alleles in the African population. The two risk alleles found to confer an elevated risk for FSGS and H-ESRD includes "G1," a two locus allele found in a 10-kb region in the last exon of APOL1, and "G2," a six base pair deletion located in close proximity to the G1 risk allele (Genovese et al., *Science* 329:841-845, 2010). These risk alleles in APOL1 are only found in individuals of African descent with allele frequencies of 38% for G1 and 8% for G2 in the African Yoruba population. These alleles appear to act in a recessive manner, with a 7 to 10 fold increased risk of H-ESKD or FSGS conferred by the presence of a risk-associated allele in both copies of APOL1.

Given the association between APOL1 risk alleles and non-diabetic renal disease in African Americans, we tested whether African Americans with ESRD and who are homozygous for APOL1 risk alleles progress to ESRD at an earlier age than those who do not have these risk alleles. The tests were performed in a cohort of non-diabetic African American subjects initiating chronic hemodialysis in the United States.

Results

Subject characteristics, including demographic information, income, vascular access, cause of ESRD and laboratory values are summarized in Table 10. The mean age of hemodialysis initiation among all subjects was 55.2±17.1 years.

Figure 5:
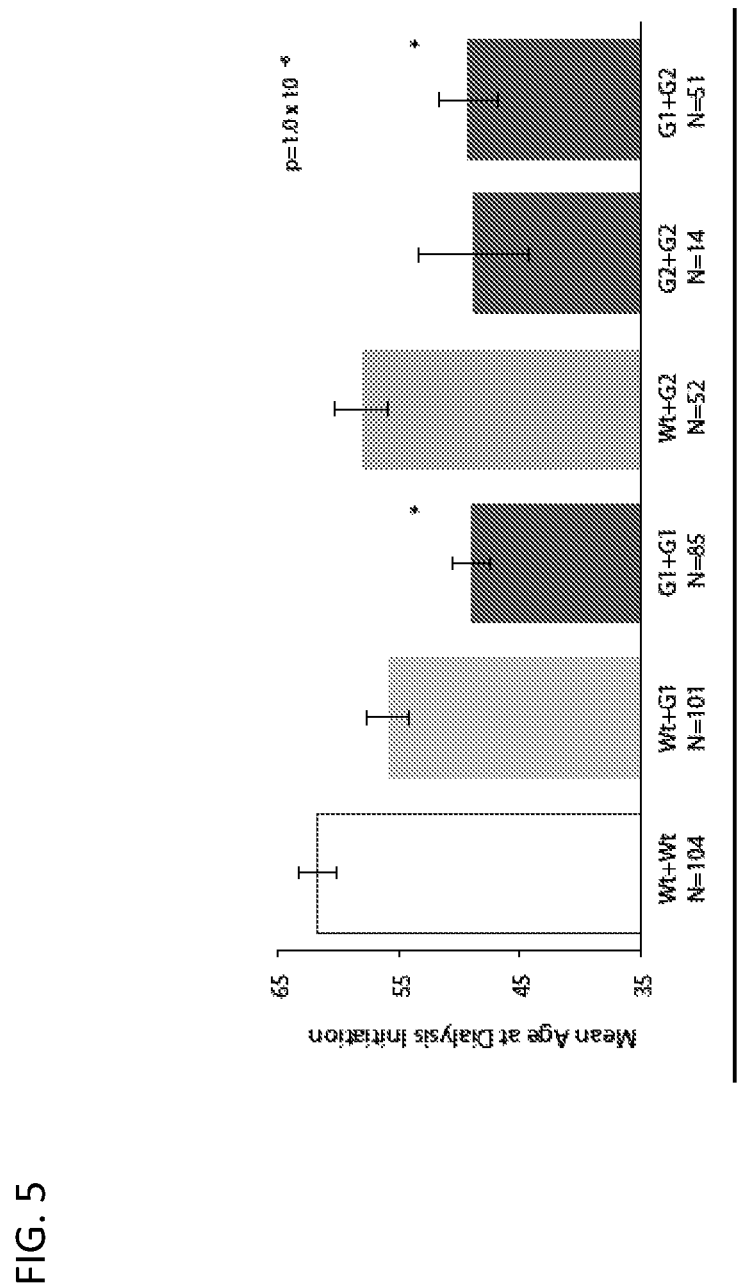
FIG. 5 shows the mean age at dialysis initiation for subjects by APOL1 risk allele status. Due to the proximity of the alleles it is not expected for a diploid sample to have more then two risk alleles, only six groups existed within this dataset; Wt+Wt, Wt+G1, G1+G1, Wt+G2, G2+G2, G1+G2. Bar height is the mean age. Error bars denote the standard error. *significantly different from wild type (Wt+Wt)

When subjects were stratified into six unique groups according to the number of G1 or G2 risk alleles, only subjects with two G1 risk alleles had significantly lower mean age at hemodialysis initiation compared to subjects without these APOL1 risk alleles (Wt+Wt=61.8±17.0 vs. Wt+G1=55.9±16.7 [p=0.152]; vs. G1+G1=49.0±14.9 [p=3.0×10$^{-6}$]; vs. G1+G2=49.3±17.0 [p=1.83×10$^{-4}$], FIG. 5). In contrast, subjects with one or two G2 risk alleles, but no G1 risk alleles, did not begin hemodialysis at an earlier age compared with subjects who lacked the G1 or G2 risk alleles (Wt+G2=58.1±16.3 [p=0.96], G2+G2=48.9±15.3 [p=0.09]). However, the number of individuals with the G2+G2 risk alleles was small. We therefore conducted subsequent analyses only with G1 risk alleles. Decreased power from exclusion of subjects with G2 risk alleles did not dramatically change the results of the analysis. Including all subjects, regardless of G2 risk, mean age at hemodialysis was significantly lower among those with two G1 risk alleles compared to those without G1 risk alleles (p=1.0×10$^{-6}$).

Table 11 shows subject characteristics according to whether subjects had zero, one, or two copies of the G1 risk allele. The p-values in Table 11 represent comparisons between the genotypes. G1 homozygotes, heterozygotes, and subjects without the G1 risk allele had a similar proportion of male subjects and similar income distribution, and similar locations of hemodialysis initiation. Subjects with and without G1 alleles had similar systolic and diastolic blood pressures, parathyroid hormone levels, calcium levels, hemoglobin concentration, and albumin concentrations. Subjects with G1 risk alleles tended to have higher serum creatinine levels (p=1.0×10$^{-6}$), perhaps due to their age. To investigate possible confounders between G1 risk allele and age at hemodialysis initiation, we also investigated factors independently correlated with mean age at hemodialysis initiation; BMI (r=−0.224, p=1.2×10$^{-4}$); serum creatinine (r=−0.439, p=1.5×10$^{-14}$); systolic blood pressure (r=−0.188, p=1.3×10$^{-3}$); diastolic blood pressure (r=−0.490, p=9.2×10$^{-19}$). We estimated eGFR levels using the MDRD formula and found that subjects with G1 risk alleles had lower eGFR levels at ESRD initiation (p=8.1×10$^{-5}$).

Figure 6:
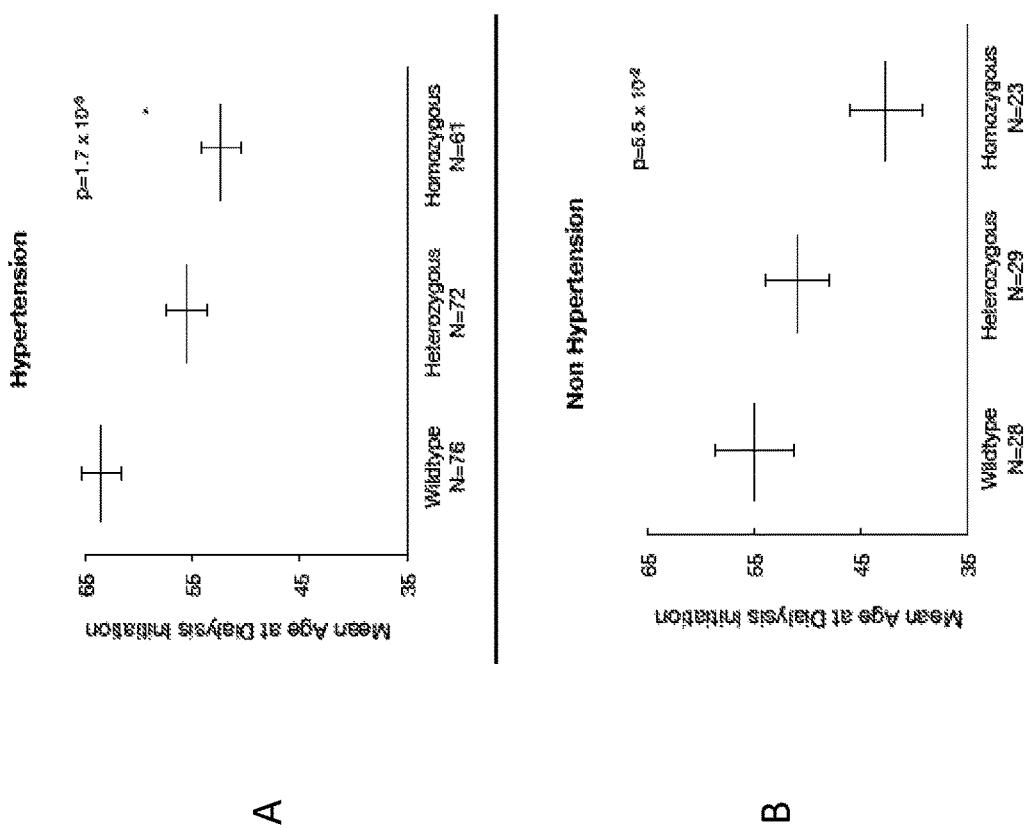
FIGS. 6A and 6B show the mean age at dialysis for subjects with a G1 risk allele.

In consonance with other U.S. renal study populations, in nearly three-fourths of our subjects ESRD was caused by hypertension. Other causes of ESRD in our population, including HIV, inflammation, toxins, etc. were grouped together as 'other.' In stratified analyses by cause of ESRD, the mean age at initiation of hemodialysis remained younger in H-ESRD subjects with G1 risk alleles but not in subjects with other reported causes of ESRD, FIG. 6.

Subjects with ESRD due to causes other than hypertension initiated chronic hemodialysis at an earlier mean age than subjects with H-ESRD (50.6±18.0 years vs. 58.1±16.3 years, p=7.8×10$^{-4}$). In multivariate regression models, the presence of G1 risk alleles remained significantly associated with early hemodialysis initiation after adjustment for demographic and socioeconomic variables and cause of ESRD among non-diabetics (Table 12). The average values in Table 12 represent the predicted values estimated from multivariate regression equations controlling for socio-demographic and clinical characteristics. In a similar model, when we did not stratify by cause of ESRD (hypertension vs other), we found that the G1 allele remained associated with age of hemodialysis initiation.

Discussion

We aimed to determine if the G1 or G2 sequence risk alleles of the APOL1 gene (which are associated with an increased risk of renal disease in African Americans) are associated with initiating chronic hemodialysis at a younger age—a marker of the severity of progressive CKD. We found that African Americans with two copies of the G1 risk allele initiated chronic hemodialysis approximately ten years earlier than those without this allele. Subjects with one copy of the G1 allele initiated hemodialysis an average of six years earlier. These estimates were unchanged after adjustment for a variety of socio-demographic factors. The presence of the G2 allele may be associated with the initiation of hemodialysis at a younger age.

APOL1 risk alleles are associated with FSGS and H-ESKD (Genovese et al., *Kidney Int*, supra). This study shows that these risk alleles are also associated with age at first start of chronic hemodialysis, a measure we used as a surrogate for age of developing ESRD. Our data support the conceptual model that APOL1 risk alleles either trigger onset of renal disease at an earlier age, or once initiated, alter the rate of progression.

Several factors may influence increased risk for ESRD in African Americans. Milder forms of kidney disease, CKD stages are less prevalent in African Americans while stage 1V CKD and ESRD are much more common (System, supra; Hsu et al., supra; Volkova et al., *J. Am. Soc. Nephrol.* 19:356-364, 2008). Consistent with this, in the ArMORR study, the overall mean age at hemodialysis initiation for Caucasians is 65.5±14.9 years, compared to 57.8±15.4 years in African Americans (p<1.0×10$^{-4}$) (Shurraw et al., *Am. J. Kidney Dis.* 55:875-884, 2010). This is consistent with an accelerated progression of ESRD in these subjects. This could also be explained by an alternative pathogenesis for ESRD in some African Americans, leading to early clinical onset of ESRD, potentially mediated by mutations in the APOL1 gene. Several factors have been associated with the rate of progression to ESRD in African Americans, including, e.g., proteinuria, 25-hydroxyvitamin D levels, and late referral to specialty care. One or more of these risk factors may mediate the relationship between APOL1 risk alleles and ESRD in this population (Melamed et al., *J. Am. Soc. Nephrol.* 20:2631-2639, 2009). In this study we found that body mass index and income were unlikely to confound the association between APOL1 genetic risk alleles and earlier age at hemodialysis initiation.

Subjects with two copies of the G2 risk allele may initiate hemodialysis at a younger age, while subjects with one copy of the G2 risk allele appear to initiate hemodialysis at approximately the same age as subjects without any risk alleles.

As there was less power to detect effects of the rarer G2 risk allele, it is less clear to what extent this characteristic affects age at hemodialysis initiation. Post-hoc power analysis revealed a sample size of 34 per G2 risk allele group is required to obtain a power of 0.8, and 45 to obtain a power of 0.9. Based on our current sample sizes it is likely that homozygous G2 risk allele groups were underpowered to find any significant differences between age of hemodialysis initiation. Also, just one copy of the G1 allele was associated with a younger age at hemodialysis initiation.

In conclusion, genetic variation in APOL1 is associated with earlier onset of ESRD in African Americans without diabetes mellitus as the etiology of end stage renal failure, and thus APOL1 genetic screening can be used to identify patients at risk so that preventative interventions can be initiated much earlier than is currently practiced.

Methods

Subjects

Subjects were African Americans with non-diabetic ESRD enrolled in Accelerated Mortality on Renal Replacement (ArMORR), a prospective cohort study of 10,044 subjects who initiated chronic hemodialysis at any of 1056 US hemodialysis centers operated by Fresenius Medical Care, North America between June 2004 and August 2005. [15] The study was approved by the Institutional Review Board (IRB) of the Massachusetts General Hospital (MGH), which waived the need for informed consent of this respository. Blood samples from 407 non-diabetic African Americans were available for DNA extraction.

Data Collection

Data were collected prospectively by care-givers and included demographics, body mass index, co-morbidities, hemodialysis access (catheter, graft, or fistula), and reported cause of ESRD. Laboratory tests on blood samples collected within 14 days of hemodialysis initiation were performed by a central laboratory (Spectra East, Rockland, N.J.) and included albumin, creatinine, calcium, phosphate, and hemoglobin, measured using standard multisample automated analyzers. Intact parathyroid hormone (PTH) was measured using Nichols Bio-intact assay of full-length 1-84 PTH. Subject's eGFR levels were estimated using the Modification of Diet in Renal Disease (MDRD) formula (Levey et al., *Ann. Intern. Med.* 130:461-470, 1999).

Each subject received chronic hemodialysis at an outpatient Fresenius Medical Center North American facility. Because age of initiation of chronic hemodialysis may differ by region and income, median household income of African Americans living in the zip code for each facility was determined from U.S. Census data for the year 2000 and used as an estimate of socioeconomic status. (Kinchen et al., *Ann. Intern. Med.* 137:479-486, 2002.) We divided subjects into three equally sized groups (high, medium, and low socioeconomic status) based on median household income of African Americans in the zip code in which they initiated dialysis. We also assigned subjects to one of three geographic regions based on their hemodialysis facility's zip code and U.S. Census Regions (U.S. Census, available from: http://factfinder.census.gov/servlet/DTTable?_bm=y&-context=dt&-ds_name=DEC_2000_SF3_U&-CONTEXT=dt&-mt_name=DEC_2000_SF3_U_P151B&-tree_id=403&-redoLog=false&-all_geo_types=N&-geo_id=01000US&-geo_id=02000US1&-geo_id=02000US2&-geo_id=02000US3&-geo_id=02000US4&-search_results=01000US&-format=&-_lang=en, retrieved 2002). These regions included Northeast (Connecticut, Massachusetts, Maine, New Hampshire, New Jersey, Pennsylvania, Puerto Rico, Rhode Island), Midwest/West (Arizona, Colorado, Illinois, Kansas, New Mexico, Missouri, Minnesota, Montana, Ohio, Wisconsin), and South (Alabama, Arkansas, Washington D.C., Delaware, Florida, Georgia, Kentucky, Louisiana, Maryland, Mississippi, North Carolina, Oklahoma, South Carolina, Tennessee, Texas, Virginia, and West Virginia). Puerto Rico and the Island Areas are not part of any census region or census division. For this reason, Puerto Rico was assigned to the North East region based on Standard Federal Regions where Puerto Rico is grouped in Region III with New York and New Jersey (*Federal Regions*, available from: http://www.atsdr.cdc.gov/WebMaps/helpcontent/MapOptionsAdvance.asp#regions, retrieved 2010).

Genotyping

Genomic DNA was extracted from whole blood stored in PaxGene tubes using a protocol adapted from PreAnalytix using a QiagenAutoPure extraction robot (Harvard Partners Center for Genetics and Genomics, Cambridge, Mass., USA). In all samples, DNA quality was assessed with 260/280 OD ratios. The patients' DNA samples were diluted in water to 10 nanograms per microliter, and 300 nanograms of each DNA sample were sent to Polymorphic DNA Technologies in Alameda, Calif., which provided assay design, oligonucleotide primers, PCR amplification, DNA sequencing and data analysis. Polymorphic DNA Technologies uses Sanger dideoxy DNA sequencing and employs automated high throughput capillary electrophoresis DNA sequencing instruments and is less prone to error rates, especially when two alleles, such as G1 and G2, are juxtaposed close to each other.

We considered both G1 and G2 risk alleles and classified the subjects by APOL1 risk allele status into groups depending on the number of G1 or G2 alleles present. This created six unique groups (WT+WT, G1+WT, G1+G1, G2+WT, G2+G2, G1+G2). Due to mutual exclusivity of G1 and G2, no subjects had more than two risk alleles in total (FIG. 5). We then considered G1 and G2 risk alleles separately and compared the age of hemodialysis initiation in subjects with zero, one, or two copies of each allele.

Statistical Analysis

Analysis of variance (ANOVA) with Sidak post-hoc tests was used to compare mean ages at hemodialysis initiation and other relevant continuous variables across genotypic groups. Pearson correlation coefficients were used to examine the associations between continuous variables. Chi-squared tests were used for categorical variables. Multivariate linear regression modeling was used to obtain the average predicted age of hemodialysis initiation for G1 risk alleles, excluding G2 risk alleles, after adjustment for socio-economic, demographic and clinical factors. All statistical analyses were performed using SAS version 9.2 software (Cary, N.C.) and STATA version 11 (College Station, Tex.). Two-tailed p-values of <0.05 were considered significant.

Example 9

An APOL1 Gene Inversion as a Risk/Resistance Allele

Figure 7:
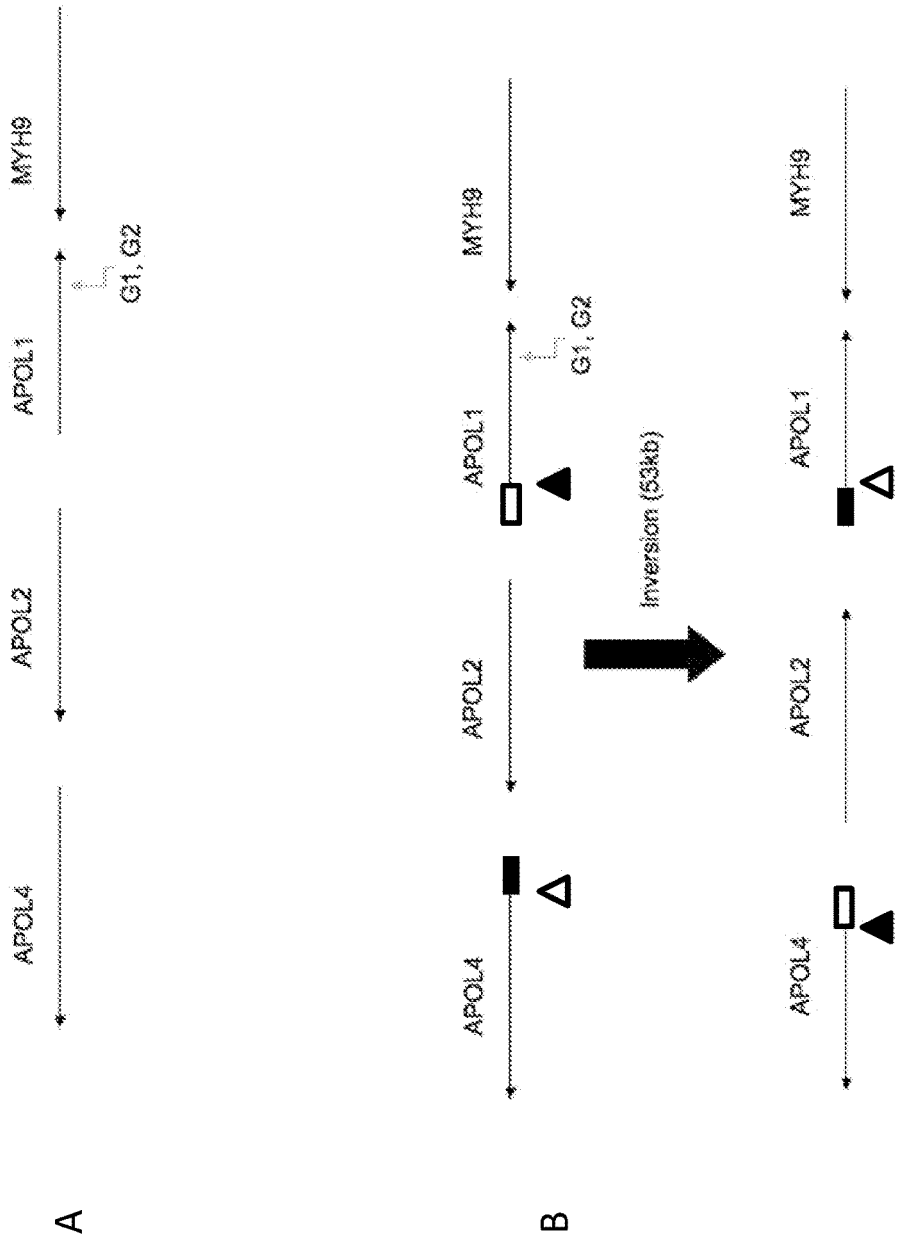
FIG. 7A is a schematic showing the relationship of the APOL1, APOL2, and APOL4 genes on chromosome 22. The G1 and G2 alleles are also shown.
FIG. 7B is a schematic showing the inversion of a segment of DNA including the 5' end of APOL4, all of APOL2, and the 5' end of APOL1.

As discussed above, the G1 and G2 variants are located in the C-terminal end of the APOL1 gene product. APOL1, APOL2, and APOL4 are located in close proximity to one another on chromosome 22 (see FIG. 7A, not to scale).

Figure 8:
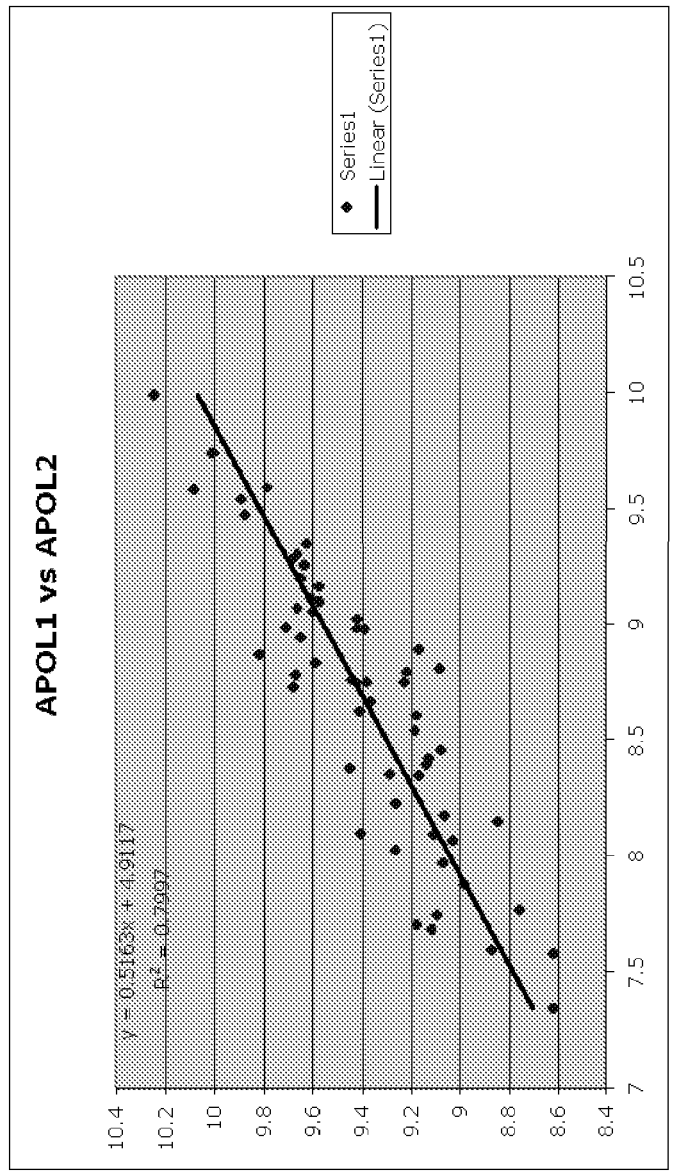
FIG. 8 is a graph of HapMap gene expression data that showing the coordinated regulation of APOL1 and APOL2.

The tail to tail (5' to 5') arrangement of APOL1 and APOL2 suggests coordinated regulation, a prediction that has been confirmed with HapMap gene expression data (see FIG. 8).

Using bioinformatics, we discovered another APOL1 gene risk/resistance allele that is a chromosomal rearrangement. The chromosomal rearrangement inversion is predicted to invert a segment of DNA including the 5' end of APOL4, all of APOL2, and the 5' end of APOL1 (see FIG. 7B). Individuals with the rearrangement inversion on a given chromosome have several important changes:

a) The reference APOL4 gene is replaced by an APOL1/APOL4 hybrid gene;
b) The reference APOL1 gene is replaced by an APOL4/APOL1 hybrid gene;
c) APOL4 expression is driven by the reference APOL1 promoter, and APOL1 is driven by the reference APOL4 promoter; and
d) APOL1 and APOL2 coordinated expression may now be unlinked.

Figure 9:
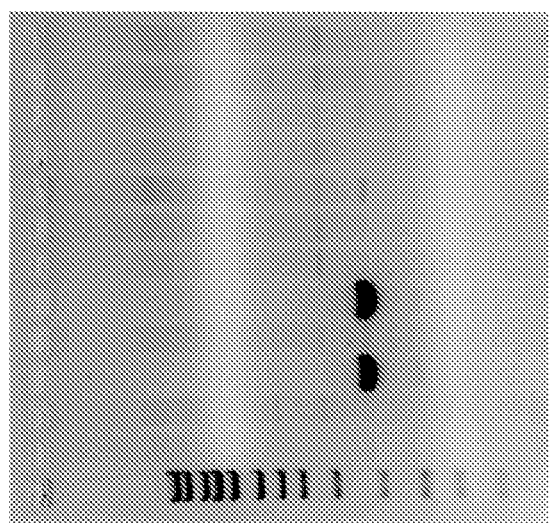
FIG. 9 is a photograph of a gel showing the presence of a APOL1-APOL4 hybrid gene following PCR amplification from 12 human samples. Lane 1 shows a size ladder. Lanes 4 and 6 show the inversion.

We validated the existence of the inversion at the APOL1/APOL4 junction using PCR in human samples (see FIG. 9).

The inversion in the APOL1 gene may result in replacement of up to three exons in APOL1 by sequence from APOL4 (e.g., the inversion may result in replacement of all or a portion of only the first exon, all or a portion of the first and/or second exon, and/or all or a portion of the first, second, or third exon of the APOL1 gene). These three exons may cover a range of 2000-2500 base pairs of genomic DNA (e.g., in a range of from about 100 base pairs to about 3000 base pairs of genomic DNA, such as a range from 1000 base pairs to about 2500 base pairs of genomic DNA), and may encode a maximum of about 420 base pairs of transcript (e.g., a range of from about 20 base pairs to about 500 base pairs of transcript, such as from about 100 base pairs to about 420 base pairs of transcript DNA). The actual coding sequence replaced in the APOL1 protein may only code for 1 to about 30 amino acids, e.g., about 10 to about 20 amino acids, e.g., about 14 amino acids from APOL4. These substituted amino acids may all appear in the preprotein portion of the hybrid APOL4/APOL1 protein and all or a portion of the replaced amino acids may be cleaved depending upon the extent and actual sequence of the inversion.

As shown in FIG. 10, the sequence in the inverted chromosome is reference APOL1 at the 5' end and reference APOL4 at the 3' end. The breakpoints on hg18 are at approximately chr22:34,981,580 to chr22:34,981,980 at the APOL1 end, and chr22:34,927,460 to chr22:34,927,060 at the APOL4 end.

Figure 11:
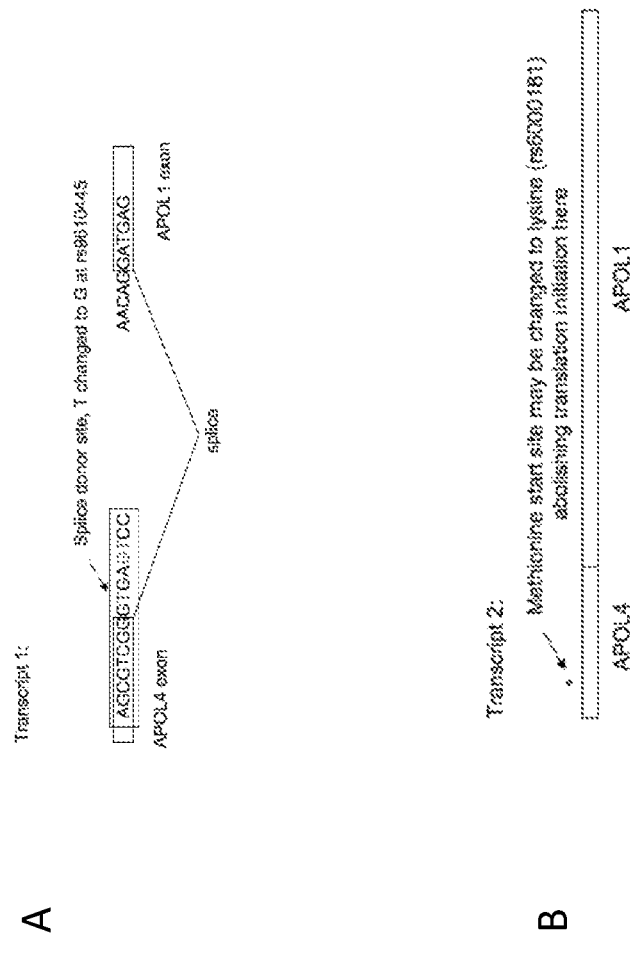
FIG. 11A shows a potential transcript formed in individuals with the G3 inversion and another SNP, rs9610445 (the C allele), in which an essential splice site is eliminated. The donor splice site sequence of APOL4 (SEQ ID NO: 8) and the acceptor splice site of APOL1 (SEQ ID NO: 9) are shown.
FIG. 11B is a potential transcript formed in individuals with the G3 inversion and another SNP, rs6000181 T (minor) allele, in which a methionine start site is eliminated.

The functional consequences of the inversion are predicted to be one or more of the following:

a) the native APOL1 promoter is eliminated, and replaced by a promoter that either expresses APOL1 at much lower levels or may not express APOL1 at all;
b) in individuals with the inversion and another SNP, rs9610445 (the C allele), an essential splice site is eliminated, causing an alteration in the transcript with potential functional consequences (see FIG. 11A);
c) in individuals with the inversion and another SNP, rs6000181 T (minor) allele, a methionine start site is eliminated, potentially altering translation of APOL1 (see FIG. 11B).
d) APOL1 and APOL2 expression are no longer coordinated; and/or
e) The N-termini of ApoL1 and ApoL4 proteins are exchanged. Under normal conditions, this may have no effect, as APOL1 has a signal peptide that is cleaved prior to export from the cell, effectively removing the amino acids contributed by APOL4. However, in the setting of dramatic APOL1 upregulation that we have observed when cells are exposed to inflammatory factors, the APOL4-encoded region may not be efficiently cleaved and could affect molecular function.

Despite the unusually large odds ratio for renal disease associated with 2 APOL1 renal risk variants (G1 and G2), some individuals with 2 risk variants do not develop disease, while some with 0 or 1 variant do develop disease. The functional properties of the inversion may be a "G3" that will improve predictive value of APOL1 testing. Thus, the identification of the G1, G2, and/or G3 risk alleles in a human subject is predictive of a genetic predisposition to and/or increased risk of the development of renal disease in the human subject.

In addition, for the reasons given herein, G3 may also be a resistance allele that can be detected alone or in combination with G1 and/or G3 in a human subject to determine a resistance to a disease associated with infection by a *Trypanosoma* spp. in the human subject.

OTHER EMBODIMENTS

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth.

All publications and patent applications mentioned in this specification, including the priority application, U.S. Application Ser. No. 61/325,343, are herein incorporated by reference to the same extent as if each independent publication or patent application was specifically and individually indicated to be incorporated by reference in their entirety.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

TABLE 3

Association of variants on chromosome 22 with FSGS using Fisher's exact test

| Variant | Position (NCBI 36) | Derived allele | Frequency derived allele in cases | Frequency derived allele in controls | Ancestral allele | P-value |
|---|---|---|---|---|---|---|
| rs11089781 | 34886714 | A | 0.32 | 0.21 | G | 0.001341 |
| rs7364143 | 34932129 | T | 0.56 | 0.4 | G | 9.904e−06 |
| rs7289037 | 34938336 | A | 0.53 | 0.33 | G | 5.118e−08 |
| rs8136528 | 34941252 | T | 0.52 | 0.34 | C | 4.977e−07 |
| rs4821469 | 34946391 | C | 0.7 | 0.51 | T | 9.835e−08 |
| rs73885303 | 34953617 | T | 0 | 0 | C | 0.4759 |
| rs10854687 | 34954365 | A | 0.51 | 0.3 | C | 4.117e−09 |
| rs9622362 | 34986390 | A | 0.04 | 0.09 | C | 0.01488 |
| rs9622363 | 34986501 | G | 0.82 | 0.51 | A | 6.112e−20 |
| rs41297245 | 34987686 | A | 0.01 | 0.05 | G | 0.000927 |
| rs2239785 | 34991276 | A | 0.14 | 0.35 | G | 3.081e−12 |
| rs136175 | 34991512 | A | 0.97 | 0.93 | G | 0.01712 |
| rs73403889 | 34991637 | A | 0 | 0 | G | 1 |
| rs16996616 | 34991837 | A | 0.03 | 0.08 | G | 0.00933 |
| rs73885319 | 34991852 | G | 0.53 | 0.19 | A | 1.07e−23 |
| rs60910145 | 34991980 | G | 0.52 | 0.18 | T | 2.591e−23 |
| rs71785313 | 34991997 | D | 0.23 | 0.15 | I | 0.008882 |
| rs58384577 | 34993159 | C | 0.49 | 0.19 | T | 9.782e−18 |
| rs60295735 | 34997100 | A | 0.5 | 0.2 | G | 9.128e−17 |
| rs56277602 | 34998706 | G | 0.5 | 0.76 | T | 2.359e−13 |
| rs73885325 | 35000629 | T | 0.49 | 0.25 | A | 6.903e−12 |
| SNP 2bp after rs136196 | 35005098 | A | 0.44 | 0.22 | G | 1.482e−09 |
| rs73405714 | 35005359 | G | 0.44 | 0.22 | A | 9.451e−10 |
| rs11703176 | 35008422 | A | 0.48 | 0.31 | C | 3.782e−06 |
| rs58168942 | 35012680 | A | 0.4 | 0.19 | G | 2.652e−10 |
| rs5756130 | 35014277 | T | 0.06 | 0.1 | C | 0.08136 |
| rs6000226 | 35014513 | T | 0.32 | 0.26 | C | 0.09085 |
| rs11912763 | 35014668 | A | 0.41 | 0.19 | G | 9.573e−12 |
| rs11549907 | 35014926 | T | 0.06 | 0.08 | C | 0.2976 |
| rs6000229 | 35016105 | T | 0.2 | 0.36 | C | 5.378e−06 |
| rs6000223 | 35017908 | 0 | 0 | 0 | A | 1 |
| rs73405726 | 35018652 | C | 0.47 | 0.29 | G | 3.09e−07 |
| rs73405727 | 35020433 | T | 0.42 | 0.19 | C | 2.243e−11 |
| rs2239786 | 35021873 | C | 0.32 | 0.29 | G | 0.4288 |
| rs16996648 | 35022698 | C | 0.47 | 0.29 | T | 3.09e−07 |
| rs56339459 | 35023558 | T | 0.42 | 0.19 | C | 8.107e−12 |
| rs4821481 | 35025888 | T | 0.17 | 0.36 | C | 4.398e−09 |
| rs6000235 | 35026033 | T | 0.78 | 0.53 | C | 7.393e−13 |
| rs3752462 | 35040129 | T | 0.87 | 0.72 | C | 1.82e−07 |
| rs2239784 | 35044581 | T | 0.72 | 0.63 | C | 0.005961 |
| rs8141189 | 35044656 | T | 0.57 | 0.7 | A | 0.0002506 |
| rs7285770 | 35045413 | A | 0.41 | 0.25 | G | 5.869e−06 |
| rs55816447 | 35047283 | T | 0.42 | 0.25 | C | 7.291e−07 |
| rs55670830 | 35049098 | C | 0.61 | 0.76 | A | 2.948e−05 |
| rs16996668 | 35049131 | G | 0.58 | 0.75 | C | 2.92e−06 |
| rs12160045 | 35049306 | G | 0.55 | 0.68 | A | 0.0004368 |
| rs11912139 | 35052407 | T | 0.41 | 0.25 | C | 1.34e−06 |
| rs11912881 | 35053384 | A | 0.41 | 0.25 | T | 8.857e−06 |
| rs16996672 | 35055916 | T | 0.45 | 0.27 | C | 1.611e−07 |
| rs16996674 | 35056598 | T | 0.41 | 0.25 | C | 3.157e−06 |
| rs16996677 | 35057229 | A | 0.45 | 0.26 | G | 6.587e−08 |

TABLE 4

Number and frequencies of APOL1 genotypes and alleles in FSGS and hypertension-attributed ESKD cases and controls

| | FSGS Cases and Controls | | | | Hypertension-attributed ESKD | |
|---|---|---|---|---|---|---|
| | BWH Cases | NIH Cases | Total Cases | NIH Controls | WFU Cases | WFU Controls |
| Genotype | | | | | | |
| WT + WT | 3 | 26 | 29 | 77 | 239 | 409 |
| WT + G1 | 6 | 21 | 27 | 41 | 173 | 250 |
| WT + G2 | 0 | 9 | 9 | 36 | 124 | 155 |
| G1 + G1 | 25 | 35 | 60 | 9 | 219 | 41 |
| G1 + G2 | 15 | 38 | 53 | 8 | 203 | 50 |
| G2 + G2 | 3 | 11 | 14 | 5 | 44 | 18 |
| Total | 52 | 140 | 192 | 176 | 1002 | 923 |

TABLE 4-continued

Number and frequencies of APOL1 genotypes and alleles in FSGS and hypertension-attributed ESKD cases and controls

|  | FSGS Cases and Controls | | | | Hypertension-attributed ESKD | |
|---|---|---|---|---|---|---|
|  | BWH Cases | NIH Cases | Total Cases | NIH Controls | WFU Cases | WFU Controls |
| Allele | | | | | | |
| G1 Freq. | 0.68 | 0.47 | 0.52 | 0.18 | 0.41 | 0.21 |
| G2 Freq. | 0.19 | 0.25 | 0.23 | 0.15 | 0.21 | 0.13 |

Samples for which either the G1 or G2 assay failed are not reported

TABLE 5

Association of different variants on chromosome 22 with FSGS after controlling for variant rs73885319 (which co-segregates with rs60910145) using logistic regression

| Variant | Position (NCBI 36) | P-value |
|---|---|---|
| rs11089781 | 34886714 | 0.925 |
| rs7364143 | 34932129 | 0.9919 |
| rs7289037 | 34938336 | 0.2779 |
| rs8136528 | 34941252 | 0.5498 |
| rs4821469 | 34946391 | 0.05454 |
| rs73885303 | 34953617 | 0.9993 |
| rs10854687 | 34954365 | 0.3387 |
| rs9622362 | 34986390 | 0.8758 |
| rs9622363 | 34986501 | 0.0001509 |
| rs41297245 | 34987686 | 0.1298 |
| rs2239785 | 34991276 | 0.00566 |
| rs136175 | 34991512 | 0.2976 |
| rs73403889 | 34991637 | 0.9993 |
| rs16996616 | 34991837 | 0.5397 |
| rs73885319 | 34991852 | NA |
| rs60910145 | 34991980 | 0.6051 |
| rs71785313 | 34991997 | 4.377e−07 |
| rs58384577 | 34993159 | 0.1982 |
| rs60295735 | 34997100 | 0.6759 |
| rs56277602 | 34998706 | 0.3886 |
| rs73885325 | 35000629 | 0.3589 |
| SNP 2bp after rs136196 | 35005098 | 0.1207 |
| rs73405714 | 35005359 | 0.1746 |
| rs11703176 | 35008422 | 0.02567 |
| rs58168942 | 35012680 | 0.2972 |
| rs5756130 | 35014277 | 0.2318 |
| rs6000226 | 35014513 | 0.0001059 |
| rs11912763 | 35014668 | 0.4741 |
| rs11549907 | 35014926 | 0.9798 |
| rs6000229 | 35016105 | 0.1074 |
| rs6000223 | 35017908 | NA |
| rs73405726 | 35018652 | 0.1368 |
| rs73405727 | 35020433 | 0.5361 |
| rs2239786 | 35021873 | 0.0005036 |
| rs16996648 | 35022698 | 0.1368 |
| rs56339459 | 35023558 | 0.3864 |
| rs4821481 | 35025888 | 0.003736 |
| rs6000235 | 35026033 | 0.002684 |
| rs3752462 | 35040129 | 0.003073 |
| rs2239784 | 35044581 | 0.743 |
| rs8141189 | 35044656 | 0.3762 |
| rs7285770 | 35045413 | 0.3736 |
| rs55816447 | 35047283 | 0.3485 |
| rs55670830 | 35049098 | 0.2393 |
| rs16996668 | 35049131 | 0.4054 |
| rs12160045 | 35049306 | 0.1751 |
| rs11912139 | 35052407 | 0.289 |
| rs11912881 | 35053384 | 0.3462 |
| rs16996672 | 35055916 | 0.6268 |

TABLE 5-continued

Association of different variants on chromosome 22 with FSGS after controlling for variant rs73885319 (which co-segregates with rs60910145) using logistic regression

| Variant | Position (NCBI 36) | P-value |
|---|---|---|
| rs16996674 | 35056598 | 0.3884 |
| rs16996677 | 35057229 | 0.7119 |

TABLE 6

Association of different variants on chromosome 22 with FSGS after controlling for variant rs73885319 and rs71785313 using logistic regression

| Variant | Position (NCBI 36) | P-value |
|---|---|---|
| rs11089781 | 34886714 | 0.2439 |
| rs7364143 | 34932129 | 0.1461 |
| rs7289037 | 34938336 | 0.8734 |
| rs8136528 | 34941252 | 0.3631 |
| rs4821469 | 34946391 | 0.3533 |
| rs73885303 | 34953617 | 0.9993 |
| rs10854687 | 34954365 | 0.4109 |
| rs9622362 | 34986390 | 0.13 |
| rs9622363 | 34986501 | 0.8217 |
| rs41297245 | 34987686 | 0.5326 |
| rs2239785 | 34991276 | 0.9337 |
| rs136175 | 34991512 | 0.8123 |
| rs73403889 | 34991637 | 0.9993 |
| rs16996616 | 34991837 | 0.3839 |
| rs73885319 | 34991852 | NA |
| rs60910145 | 34991980 | 0.7417 |
| rs71785313 | 34991997 | NA |
| rs58384577 | 34993159 | 0.3419 |
| rs60295735 | 34997100 | 0.9987 |
| rs56277602 | 34998706 | 0.5788 |
| rs73885325 | 35000629 | 0.5589 |
| SNP 2bp after rs136196 | 35005098 | 0.285 |
| rs73405714 | 35005359 | 0.3297 |
| rs11703176 | 35008422 | 0.1264 |
| rs58168942 | 35012680 | 0.4001 |
| rs5756130 | 35014277 | 0.5038 |
| rs6000226 | 35014513 | 0.1419 |
| rs11912763 | 35014668 | 0.529 |
| rs11549907 | 35014926 | 0.4356 |
| rs6000229 | 35016105 | 0.9112 |
| rs6000223 | 35017908 | NA |
| rs73405726 | 35018652 | 0.3053 |
| rs73405727 | 35020433 | 0.5282 |
| rs2239786 | 35021873 | 0.1924 |
| rs16996648 | 35022698 | 0.3063 |
| rs56339459 | 35023558 | 0.4316 |
| rs4821481 | 35025888 | 0.2728 |
| rs6000235 | 35026033 | 0.4815 |
| rs3752462 | 35040129 | 0.1644 |
| rs2239784 | 35044581 | 0.1031 |
| rs8141189 | 35044656 | 0.5344 |
| rs7285770 | 35045413 | 0.5092 |
| rs55816447 | 35047283 | 0.4334 |
| rs55670830 | 35049098 | 0.3437 |
| rs16996668 | 35049131 | 0.5467 |
| rs12160045 | 35049306 | 0.45 |
| rs11912139 | 35052407 | 0.3368 |
| rs11912881 | 35053384 | 0.4146 |
| rs16996672 | 35055916 | 0.8562 |
| rs16996674 | 35056598 | 0.4494 |
| rs16996677 | 35057229 | 0.954 |

TABLE 7

Association of variants on chromosome 22 with hypertensive ESKD using basic association test

| Variant | Position (NCBI 36) | Derived allele | Frequency derived allele in cases | Frequency derived allele in controls | Ancestral allele | P-value |
|---|---|---|---|---|---|---|
| rs5999985 | 34452302 | A | 0.05 | 0.04 | G | 0.3545 |
| rs41283201 | 34452326 | A | 0.07 | 0.06 | T | 0.2416 |
| rs2157258 | 34672336 | C | 0.31 | 0.33 | T | 0.2191 |
| rs16996299 | 34778586 | T | 0.41 | 0.34 | C | 3.215e−06 |
| rs6000152 | 34868999 | A | 0.08 | 0.07 | G | 0.3209 |
| rs7284379 | 34881360 | T | 0.28 | 0.19 | C | 8.155e−11 |
| rs11089781 | 34886714 | A | 0.29 | 0.21 | G | 1.327e−10 |
| rs132653 | 34886769 | T | 0.44 | 0.48 | G | 0.01523 |
| rs6000173 | 34917169 | T | 0.74 | 0.66 | G | 2.658e−08 |
| rs61730819 | 34917292 | T | 0.08 | 0.11 | C | 0.000395 |
| rs2016708 | 34948899 | T | 0.42 | 0.25 | C | 1.448e−29 |
| rs1001293 | 34960895 | T | 0.45 | 0.31 | C | 3.059e−20 |
| rs9622363 | 34986501 | G | 0.72 | 0.53 | A | 6.125e−34 |
| rs136168 | 34990788 | A | 0.44 | 0.54 | G | 2.395e−10 |
| rs16996616 | 34991837 | A | 0.05 | 0.08 | G | 0.000549 |
| rs73885319 | 34991852 | G | 0.41 | 0.21 | A | 1.097e−39 |
| rs71785313 | 34991997 | D | 0.21 | 0.13 | I | 7.276e−10 |
| rs7078 | 35007860 | G | 0.1 | 0.15 | A | 3.42e−05 |
| rs12107 | 35007928 | A | 0.07 | 0.11 | G | 1.731e−05 |
| rs16996639 | 35008348 | A | 0.1 | 0.08 | G | 0.0599 |
| rs11089787 | 35008399 | G | 0.48 | 0.38 | C | 1.642e−10 |
| rs735853 | 35009159 | G | 0.07 | 0.11 | C | 1.144e−06 |
| rs58168942 | 35012680 | A | 0.34 | 0.2 | G | 7.018e−24 |
| rs5756129 | 35014038 | C | 0.15 | 0.21 | T | 6.297e−07 |
| rs11912763 | 35014668 | A | 0.34 | 0.19 | G | 8.035e−24 |
| rs56020676 | 35020066 | C | 0.4 | 0.26 | T | 1.324e−19 |
| rs73885341 | 35021424 | A | 0.4 | 0.27 | G | 5.333e−17 |
| rs4821480 | 35025193 | T | 0.26 | 0.4 | G | 6.622e−21 |
| rs2032487 | 35025374 | T | 0.25 | 0.38 | C | 3.941e−20 |
| rs4821481 | 35025888 | T | 0.26 | 0.4 | C | 8.434e−21 |
| rs2413396 | 35038030 | C | 0.72 | 0.58 | T | 1.114e−16 |
| rs5750250 | 35038429 | G | 0.68 | 0.5 | A | 2.757e−26 |
| rs3752462 | 35040129 | T | 0.81 | 0.73 | C | 5.73e−09 |
| rs11912881 | 35053384 | A | 0.34 | 0.25 | T | 5.993e−11 |
| rs16996674 | 35056598 | T | 0.34 | 0.23 | C | 6.825e−13 |
| rs16996677 | 35057229 | A | 0.36 | 0.27 | G | 1.709e−10 |

TABLE 8

Association of different variants on chromosome 22 with hypertensive ESKD after controlling for variant rs73885319 using logistic regression

| Variant | Position (NCBI 36) | P-value |
|---|---|---|
| rs5999985 | 34452302 | 0.2828 |
| rs41283201 | 34452326 | 0.3638 |
| rs2157258 | 34672336 | 0.02322 |
| rs16996299 | 34778586 | 0.0567 |
| rs6000152 | 34868999 | 0.2081 |
| rs7284379 | 34881360 | 0.004519 |
| rs11089781 | 34886714 | 0.006513 |
| rs132653 | 34886769 | 0.5453 |
| rs6000173 | 34917169 | 0.0008435 |
| rs61730819 | 34917292 | 0.1326 |
| rs2016708 | 34948899 | 9.595e−06 |
| rs1001293 | 34960895 | 0.006298 |
| rs9622363 | 34986501 | 6.124e−08 |
| rs136168 | 34990788 | 0.01352 |
| rs16996616 | 34991837 | 0.5301 |
| rs73885319 | 34991852 | NA |
| rs71785313 | 34991997 | 8.798e−18 |
| rs7078 | 35007860 | 0.1648 |
| rs12107 | 35007928 | 0.05038 |
| rs16996639 | 35008348 | 0.002146 |
| rs11089787 | 35008399 | 0.156 |
| rs735853 | 35009159 | 0.0159 |
| rs58168942 | 35012680 | 0.9944 |
| rs5756129 | 35014038 | 0.06101 |
| rs11912763 | 35014668 | 0.3702 |
| rs56020676 | 35020066 | 0.5497 |
| rs73885341 | 35021424 | 0.9711 |
| rs4821480 | 35025193 | 6.763e−06 |
| rs2032487 | 35025374 | 2.137e−05 |
| rs4821481 | 35025888 | 8.516e−06 |
| rs2413396 | 35038030 | 0.0006269 |
| rs5750250 | 35038429 | 4.145e−08 |
| rs3752462 | 35040129 | 0.02872 |
| rs11912881 | 35053384 | 0.8152 |
| rs15996674 | 35056598 | 0.47 |
| rs16996677 | 35057229 | 0.9985 |

TABLE 9

Frequency differentiation analysis of variants near APOL1 for two African populations, Yoruba from Nigeria and Luhya from Kenya

| Variant | Position (NCBI 36) | Reference allele | Non reference allele | Frequency reference allele in YRI | Frequency non-reference allel in LWK | $F_{ST}$ | P-value |
|---|---|---|---|---|---|---|---|
| rs12185880 | 34900774 | C | G | 0.86 | 0.76 | 0.02 | 0.0453 |
| rs132681 | 34904713 | A | G | 0.07 | 0.05 | 0 | 0.5108 |
| rs132683 | 34905610 | G | A | 0.67 | 0.58 | 0.01 | 0.1986 |
| rs132686 | 34906596 | A | G | 1 | 0.97 | 0.02 | 0.0815 |
| rs132688 | 34906886 | G | A | 1 | 0.97 | 0.01 | 0.1726 |
| rs6000164 | 34907077 | C | T | 0.89 | 0.8 | 0.02 | 0.0869 |
| rs132689 | 34907092 | G | A | 0.9 | 0.95 | 0.01 | 0.1459 |
| rs5995235 | 34907888 | C | T | 0.67 | 0.62 | 0.01 | 0.3792 |
| rs6000167 | 34908800 | G | A | 0.45 | 0.52 | 0.01 | 0.3370 |
| rs132692 | 34909112 | T | C | 0.03 | 0.16 | 0.05 | 0.0012 |
| rs132693 | 34909507 | A | G | 0.01 | 0.02 | 0 | 0.6093 |
| rs2239831 | 34913030 | T | C | 0.13 | 0.21 | 0.01 | 0.1274 |
| rs916338 | 34914376 | T | C | 0.01 | 0.02 | 0 | 0.6093 |
| rs132697 | 34914659 | A | G | 0.01 | 0.07 | 0.02 | 0.0319 |
| rs8136064 | 34914892 | T | G | 0.98 | 0.91 | 0.03 | 0.0201 |
| rs1053982 | 34915510 | T | C | 0.25 | 0.41 | 0.03 | 0.0133 |
| rs5756091 | 34915667 | T | G | 0.24 | 0.41 | 0.03 | 0.0087 |
| rs5756093 | 34915917 | G | A | 1 | 1 | NaN | NaN |
| rs6000172 | 34917148 | G | A | 0.24 | 0.37 | 0.02 | 0.0413 |
| rs6000174 | 34917225 | A | G | 0.24 | 0.37 | 0.02 | 0.0407 |
| rs2227167 | 34917432 | A | G | 0.24 | 0.37 | 0.02 | 0.0378 |
| rs2269596 | 34920892 | C | T | 0.23 | 0.3 | 0.01 | 0.2156 |
| rs2007468 | 34921326 | A | G | 0.12 | 0.14 | 0 | 0.6150 |
| rs2007706 | 34922316 | C | T | 0.01 | 0.1 | 0.04 | 0.0059 |
| rs132717 | 34926598 | C | T | 0.23 | 0.44 | 0.05 | 0.0015 |
| rs132734 | 34927823 | G | A | 0.23 | 0.43 | 0.05 | 0.0012 |
| rs132735 | 34927827 | G | T | 0.52 | 0.67 | 0.02 | 0.0307 |
| rs5995251 | 34930704 | A | T | 0.61 | 0.36 | 0.06 | 0.0003 |
| rs6000190 | 34930787 | A | G | 0.61 | 0.36 | 0.06 | 0.0003 |
| rs5995252 | 34931145 | C | T | 0.6 | 0.36 | 0.06 | 0.0004 |
| rs7364143 | 34932129 | G | T | 0.53 | 0.79 | 0.08 | 5.315e−05 |
| rs5995255 | 34932725 | G | T | 0.58 | 0.38 | 0.04 | 0.0038 |
| rs6000197 | 34933240 | G | A | 0.58 | 0.37 | 0.04 | 0.0029 |
| rs132744 | 34934551 | T | C | 0.48 | 0.27 | 0.05 | 0.0015 |
| rs132745 | 34935277 | C | T | 0.15 | 0.32 | 0.04 | 0.0040 |
| rs132746 | 34935337 | C | T | 0.15 | 0.32 | 0.04 | 0.0030 |
| rs8142325 | 34935923 | A | T | 0.54 | 0.83 | 0.09 | 8.998e−06 |
| rs132749 | 34936575 | C | T | 0.81 | 0.67 | 0.03 | 0.0262 |
| rs9610448 | 34938151 | A | G | 0.22 | 0.31 | 0.01 | 0.1331 |
| rs132750 | 34938295 | C | T | 0.03 | 0.04 | 0 | 0.4781 |
| rs7289037 | 34938336 | G | A | 0.51 | 0.81 | 0.1 | 6.039e−06 |
| rs11704479 | 34939580 | G | A | 1 | 1 | NaN | NaN |
| rs4820222 | 34939685 | C | T | 0.22 | 0.32 | 0.02 | 0.0975 |
| rs6000199 | 34939878 | G | A | 0.92 | 0.84 | 0.02 | 0.0661 |
| rs8140384 | 34940517 | C | T | 0.21 | 0.22 | 0 | 0.7640 |
| rs8136528 | 34941252 | C | T | 0.52 | 0.79 | 0.09 | 1.990e−05 |
| rs5995259 | 34941809 | G | A | 0.82 | 0.76 | 0.01 | 0.3005 |
| rs1315 | 34946081 | A | C | 0.9 | 0.9 | 0 | 0.9650 |
| rs4821467 | 34946146 | G | A | 0.51 | 0.79 | 0.09 | 1.390e−05 |
| rs4821469 | 34946391 | T | C | 0.34 | 0.45 | 0.02 | 0.0877 |
| rs763086 | 34949003 | G | A | 0.34 | 0.49 | 0.03 | 0.0273 |
| rs11703398 | 34950907 | A | G | 0.83 | 0.7 | 0.03 | 0.0223 |
| rs2006259 | 34951559 | A | C | 0.35 | 0.49 | 0.02 | 0.0366 |
| rs132757 | 34951655 | T | C | 0 | 0.01 | 0.01 | 0.4369 |
| rs9619597 | 34952768 | G | T | 1 | 1 | NaN | NaN |
| rs129607 | 34952852 | T | C | 0.39 | 0.64 | 0.06 | 0.0003 |
| rs132760 | 34953677 | T | C | 0 | 0 | NaN | NaN |
| rs7285167 | 34953866 | G | A | 0.54 | 0.86 | 0.12 | 3.653e−07 |
| rs11089784 | 34956223 | C | T | 0.9 | 0.9 | 0 | 0.8770 |
| rs11703957 | 34956901 | A | G | 0.79 | 0.72 | 0.01 | 0.2647 |
| rs2010467 | 34958853 | T | C | 0.54 | 0.24 | 0.1 | 6.779e−06 |
| rs2010659 | 34959579 | A | C | 0.86 | 0.87 | 0 | 0.8853 |
| rs9610462 | 34960296 | C | A | 0.86 | 0.87 | 0 | 0.8162 |
| rs1001294 | 34960936 | C | T | 0.86 | 0.86 | 0 | 0.9329 |
| rs2157249 | 34960985 | T | C | 0.86 | 0.86 | 0 | 0.9545 |
| rs2157250 | 34961637 | G | A | 0.05 | 0.03 | 0 | 0.4757 |
| rs136142 | 34962971 | C | T | 0.65 | 0.44 | 0.05 | 0.0024 |
| rs1557534 | 34963171 | G | A | 0.97 | 0.94 | 0.01 | 0.3752 |
| rs136145 | 34965913 | A | G | 0.3 | 0.48 | 0.04 | 0.0063 |
| rs4821472 | 34977906 | T | C | 0.97 | 0.91 | 0.02 | 0.0473 |
| rs5995271 | 34978039 | G | T | 0.93 | 0.84 | 0.02 | 0.0496 |
| rs5756115 | 34978498 | A | G | 1 | 0.96 | 0.02 | 0.0804 |

TABLE 9-continued

Frequency differentiation analysis of variants near APOL1 for two African populations, Yoruba from Nigeria and Luhya from Kenya

| Variant | Position (NCBI 36) | Reference allele | Non reference allele | Frequency reference allele in YRI | Frequency non-reference allel in LWK | $F_{ST}$ | P-value |
|---|---|---|---|---|---|---|---|
| rs9610467 | 34979520 | G | A | 0.91 | 0.84 | 0.01 | 0.1329 |
| rs7284919 | 34982110 | T | C | 0.93 | 0.83 | 0.03 | 0.0229 |
| rs136148 | 34982877 | C | T | 0.1 | 0.16 | 0.01 | 0.1986 |
| rs4820224 | 34983221 | G | A | 0.99 | 0.97 | 0.01 | 0.4534 |
| rs2413395 | 34984662 | G | A | 0.93 | 0.92 | 0 | 0.7441 |
| rs136159 | 34986969 | T | C | 0 | 0.04 | 0.02 | 0.0390 |
| rs129423 | 34987275 | T | C | 0 | 0.03 | 0.02 | 0.0551 |
| rs136161 | 34987378 | G | C | 0.8 | 0.65 | 0.03 | 0.0143 |
| rs713929 | 34987542 | A | G | 0 | 0.03 | 0.02 | 0.0561 |
| rs713753 | 34988480 | C | T | 0.89 | 0.72 | 0.04 | 0.0026 |
| rs4419330 | 34988801 | T | C | 0.89 | 0.89 | 0 | 0.8258 |
| rs2239785 | 34991276 | G | A | 0.73 | 0.56 | 0.03 | 0.0088 |
| rs136174 | 34991482 | C | A | 0 | 0.07 | 0.03 | 0.0137 |
| rs136175 | 34991512 | G | A | 0 | 0.07 | 0.03 | 0.0137 |
| rs136176 | 34991592 | G | A | 0 | 0.04 | 0.03 | 0.0270 |
| rs136177 | 34991788 | G | A | 0.03 | 0.13 | 0.04 | 0.0063 |
| rs16996616 | 34991837 | G | A | 0.94 | 0.87 | 0.02 | 0.0974 |
| rs73885319 | 34991852 | G | A | 0.38 | 0.05 | 0.16 | 3.533e−09 |
| rs71785313 | 34991997 | D | I | 0.08 | 0.07 | 0 | 0.8949 |
| rs2012928 | 34993948 | G | A | 0.83 | 0.67 | 0.03 | 0.0086 |
| rs136183 | 34996271 | T | C | 0.34 | 0.55 | 0.05 | 0.0022 |
| rs4821475 | 34999041 | C | T | 0.37 | 0.46 | 0.01 | 0.1825 |
| rs9306308 | 34999716 | T | A | 0.93 | 0.86 | 0.05 | 0.0015 |
| rs136187 | 35002222 | A | C | 0.5 | 0.62 | 0.02 | 0.0783 |
| rs136196 | 35005096 | A | G | 0.31 | 0.37 | 0.01 | 0.4163 |
| rs2481 | 35007346 | G | A | 0.91 | 0.77 | 0.04 | 0.0063 |
| rs735854 | 35009004 | T | C | 0.93 | 0.78 | 0.05 | 0.0014 |
| rs5756129 | 35014038 | T | C | 0.79 | 0.7 | 0.01 | 0.1210 |
| rs5756130 | 35014277 | C | T | 0.82 | 0.83 | 0 | 0.8596 |
| rs2269529 | 35014300 | T | C | 0.97 | 0.87 | 0.04 | 0.0039 |
| rs2269530 | 35014304 | C | A | 0.97 | 0.88 | 0.03 | 0.0094 |
| rs11912763 | 35014668 | G | A | 0.67 | 0.94 | 0.12 | 4.030e−07 |
| rs1476009 | 35016002 | A | G | 0.04 | 0.02 | 0 | 0.5721 |
| rs6000229 | 35016105 | T | C | 0.28 | 0.34 | 0.01 | 0.3473 |
| rs6000233 | 35017908 | T | C | 0.64 | 0.47 | 0.03 | 0.0098 |
| rs710181 | 35021553 | A | C | 0.02 | 0.02 | 0 | 0.9960 |
| rs875725 | 35021637 | T | C | 0.93 | 0.94 | 0 | 0.6467 |
| rs2239786 | 35021873 | G | C | 0.71 | 0.53 | 0.03 | 0.0085 |
| rs875726 | 35021915 | G | A | 0.81 | 0.82 | 0 | 0.8952 |
| rs16996648 | 35022698 | T | C | 0.6 | 0.88 | 0.1 | 3.222e−06 |
| rs9610486 | 35023388 | G | A | 0.81 | 0.82 | 0 | 0.7884 |
| rs5756133 | 35023926 | T | A | 0.91 | 0.95 | 0.01 | 0.2300 |
| rs2187776 | 35025119 | C | T | 0.31 | 0.46 | 0.02 | 0.0276 |
| rs4821481 | 35025888 | C | T | 0.73 | 0.64 | 0.01 | 0.1505 |
| rs2239787 | 35028938 | C | A | 1 | 0.99 | 0 | 0.9095 |
| rs9619601 | 35030121 | A | G | 0.96 | 0.97 | 0 | 0.9326 |
| rs8137674 | 35032048 | A | G | 0.99 | 0.94 | 0.02 | 0.0888 |
| rs8138016 | 35032095 | G | A | 0.94 | 0.96 | 0 | 0.5345 |
| rs17806543 | 35034780 | C | A | 1 | 0.99 | 0.01 | 0.4376 |
| rs2239781 | 35034987 | C | T | 0.98 | 0.89 | 0.04 | 0.0052 |
| rs2239782 | 35035050 | G | A | 0.95 | 0.87 | 0.02 | 0.0403 |
| rs1557529 | 35035475 | A | G | 0.52 | 0.39 | 0.02 | 0.0577 |
| rs1557530 | 35035568 | G | A | 0.79 | 0.8 | 0 | 0.8724 |
| rs2187777 | 35036688 | C | T | 1 | 0.99 | 0.01 | 0.2717 |
| rs2157252 | 35036825 | C | A | 0.77 | 0.79 | 0 | 0.7517 |
| rs2157254 | 35037146 | G | C | 0.77 | 0.79 | 0 | 0.7517 |
| rs2157256 | 35037607 | A | G | 0.71 | 0.69 | 0 | 0.7725 |
| rs2413396 | 35038030 | C | T | 0.67 | 0.54 | 0.02 | 0.0633 |
| rs5750250 | 35038429 | G | A | 0.64 | 0.54 | 0.01 | 0.1494 |
| rs3830104 | 35038570 | T | C | 0.97 | 0.99 | 0.01 | 0.2224 |
| rs4820229 | 35038699 | A | G | 0.77 | 0.79 | 0 | 0.7517 |
| rs4820230 | 35039485 | G | A | 0.71 | 0.7 | 0 | 0.8089 |
| rs3752462 | 35040129 | T | C | 0.77 | 0.79 | 0 | 0.7954 |
| rs4820232 | 35040487 | A | G | 0.75 | 0.75 | 0 | 0.9919 |
| rs8141971 | 35041308 | A | G | 0.78 | 0.79 | 0 | 0.8734 |
| rs5756152 | 35042418 | A | G | 0.42 | 0.33 | 0.01 | 0.2106 |
| rs9610489 | 35043477 | T | C | 0.91 | 0.73 | 0.05 | 0.0010 |
| rs2239784 | 35044581 | C | T | 0.3 | 0.48 | 0.04 | 0.0050 |
| rs1005570 | 35045220 | A | G | 0.5 | 0.43 | 0.01 | 0.2882 |
| rs2071731 | 35048804 | G | A | 0.79 | 0.74 | 0.01 | 0.4006 |
| rs12159211 | 35049109 | G | A | 0.99 | 0.99 | 0 | 0.5521 |
| rs5756154 | 35050370 | C | T | 0.7 | 0.72 | 0 | 0.7700 |

TABLE 9-continued

Frequency differentiation analysis of variants near APOL1 for two
African populations, Yoruba from Nigeria and Luhya from Kenya

| Variant | Position (NCBI 36) | Reference allele | Non reference allele | Frequency reference allele in YRI | Frequency non-reference allel in LWK | $F_{ST}$ | P-value |
|---|---|---|---|---|---|---|---|
| rs5756156 | 35050725 | C | T | 0.75 | 0.77 | 0 | 0.6751 |
| rs8136069 | 35052436 | C | A | 0.79 | 0.74 | 0.01 | 0.4006 |
| rs8136336 | 35052480 | G | A | 0.04 | 0.02 | 0.01 | 0.3053 |
| rs16996672 | 35055916 | C | T | 0.63 | 0.78 | 0.03 | 0.0151 |
| rs16996677 | 35057229 | G | A | 0.63 | 0.79 | 0.03 | 0.0113 |
| rs11704382 | 35058098 | C | A | 1 | 1 | NaN | NaN |
| rs4820234 | 35059020 | A | G | 0.27 | 0.29 | 0 | 0.7013 |
| rs2413398 | 35060893 | T | G | 0.73 | 0.74 | 0 | 0.8116 |
| rs1557540 | 35062483 | C | T | 0.26 | 0.28 | 0 | 0.7824 |
| rs713839 | 35063884 | A | G | 0.73 | 0.74 | 0 | 0.8269 |
| rs739096 | 35071686 | G | C | 0.97 | 0.94 | 0.01 | 0.2819 |
| rs6000244 | 35071832 | C | T | 0.94 | 0.85 | 0.02 | 0.0357 |
| rs739097 | 35076025 | G | A | 0.35 | 0.36 | 0 | 0.9082 |
| rs5756164 | 35078939 | A | G | 0.05 | 0.09 | 0.01 | 0.2460 |
| rs11089788 | 35081047 | C | A | 0.56 | 0.63 | 0.01 | 0.3345 |
| rs136206 | 35085444 | A | G | 0.67 | 0.61 | 0.01 | 0.3496 |
| rs16996693 | 35086202 | A | C | 0.99 | 0.99 | 0 | 0.7813 |
| rs9306310 | 35088204 | G | A | 0.99 | 0.94 | 0.02 | 0.0367 |
| rs136211 | 35088493 | A | G | 0.45 | 0.38 | 0.01 | 0.3437 |
| rs16996704 | 35094734 | A | G | 0.46 | 0.52 | 0.01 | 0.3706 |
| rs933224 | 35095949 | T | C | 0.42 | 0.41 | 0 | 0.9430 |
| rs1883273 | 35099631 | G | A | 0.59 | 0.54 | 0 | 0.5139 |
| rs6000262 | 35099984 | A | G | 0.59 | 0.55 | 0 | 0.5608 |

TABLE 10

Subject Characteristics (n = 407)

| | Mean ± SD Percent (n) | Range (Min-Max) |
|---|---|---|
| Age at Dialysis Initiation | 55.2 ± 17.1 | 18.9-94.7 |
| Sex | | |
| Male | 52.3% (213) | |
| Female | 47.7% (194) | |
| Median Income | | |
| Tertile Three | 31.9% (130) | $31,924-$107,479 |
| Tertile Two | 33.2% (135) | $21,076-$31,611 |
| Tertile One | 32.4% (132) | $6,878-$20,985 |
| Unknown | 2.5% (10) | |
| Census Region | | |
| Notheast | 11.3% (46) | |
| Midwest/West | 17.0% (69) | |
| South | 69.8% (284) | |
| Unknown | 2.0% (8) | |
| Access | | |
| Catheter | 58.5% (238) | |
| Graft | 11.1% (45) | |
| Fistula | 23.3% (95) | |
| Unknown | 7.1% (29) | |
| Location of Dialysis Initiation | | |
| Inpatient | 83.5% (340) | |
| Outpatient | 16.5% (67) | |
| Cause of ESRD | | |
| Hypertension | 72.7% (296) | |
| Other | 27.0% (110) | |
| Unknown | 0.3% (1) | |
| Body Mass Index | 27.2 ± 7.8 | 13.8-67.5 |
| Systolic Blood Pressure, mm Hg | 145.0 ± 22.4 | 90.0-219.0 |
| Diastolic Blood Pressure, mm Hg | 79.4 ± 14.1 | 49.0-137.0 |
| Albumin, g/dl | 3.4 ± 0.6 | 1.3-4.7 |
| Creatinine, mg/dl | 8.1 ± 3.6 | 2.1-22.1 |
| eGFR, mL/min/1.73 m² | 9.9 ± 5.6 | 3.0-45.4 |
| PTH, pg/ml | 387.9 ± 325.8 | 4.6-2,353.4 |
| Calcium, mg/dl | 8.4 ± 1.0 | 4.3-12.7 |
| Hemoglobin, g/dl | 9.9 ± 1.3 | 5.9-14.9 | eGFR = Estimated Glomerular Filtration Rate

TABLE 11

Subject Characteristics by G1 Risk Allele Status

| | Wild Type (n = 104) | Heterozygous (n = 101) | Homozygous (n = 85) | p-value |
|---|---|---|---|---|
| Age at Dialysis Initiation* | 61.8 × 17.1[a,b] | 55.9 × 16.7[a] | 49.0 × 14.9[b] | $1.0 \times 10^{-6}$ |
| Sex | | | | 0.9314 |
| Male | 51.0% (53) | 53.5% (54) | 52.9% (45) | |
| Female | 49.0% (51) | 46.5% (47) | 47.1% (40) | |

TABLE 11-continued

Subject Characteristics by G1 Risk Allele Status

| | Wild Type (n = 104) | Heterozygous (n = 101) | Homozygous (n = 85) | p-value |
|---|---|---|---|---|
| Median Income | | | | 0.6869 |
| Third tertile | 26.9% (28) | 34.7% (35) | 35.3% (30) | |
| Second tertile | 29.8% (31) | 33.7% (34) | 32.9% (28) | |
| First tertile | 37.5% (39) | 30.7% (31) | 31.8% (27) | |
| Unknown | 5.8% (6) | 1.0% (1) | 0.0% (0) | |
| Census Region | | | | 0.7810 |
| Notheast | 11.5% (12) | 13.9% (14) | 9.4% (8) | |
| Midwest/West | 20.2% (21) | 15.8% (16) | 17.7% (15) | |
| South | 64.4% (67) | 69.3% (70) | 72.9% (62) | |
| Unknown | 3.9% (4) | 1.0% (1) | 0.0% (0) | |
| Access | | | | 0.8344 |
| Catheter | 57.7% (60) | 63.4% (64) | 58.8% (50) | |
| Graft | 15.4% (16) | 10.9% (11) | 12.9% (11) | |
| Fistula | 19.2% (20) | 20.8% (21) | 23.5% (20) | |
| Unknown | 7.7% (8) | 5.0% (5) | 4.7% (4) | |
| Location of Dialysis Initiation | | | | 0.4177 |
| Inpatient | 78.9% (82) | 85.2% (86) | 84.7% (72) | |
| Outpatient | 21.2% (22) | 14.9% (15) | 15.3% (13) | |
| Cause of ESRD | | | | 0.9573 |
| Hypertension | 73.1% (76) | 71.3% (72) | 71.8% (61) | |
| Other | 26.9% (28) | 28.7% (29) | 27.1% (23) | |
| Unknown | 0.0% (0) | 0.0% (0) | 1.2% (1) | |
| Body Mass Index | 25.9 ± 6.3 | 26.9 ± 7.5 | 27.6 ± 7.9 | 0.2838 |
| Systolic Blood Pressure, mm Hg | 146.6 ± 22.3 | 145.4 ± 23.5 | 141.3 ± 20.6 | 0.2514 |
| Diastolic Blood Pressure, mm Hg | 77.8 ± 12.9 | 79.3 ± 15.2 | 80.6 ± 14.7 | 0.3898 |
| Albumin, g/dl | 3.5 ± 0.6 | 3.4 ± 0.6 | 3.5 ± 0.6 | 0.6550 |
| Creatinine, mg/dl | $6.8 ± 2.8^{a,b}$ | $7.7 ± 3.4^a$ | $9.4 ± 3.8^b$ | $1.0 × 10^{-6}$ |
| eGFR, mL/min/1.73 m$^2$ | $11.6 ± 6.6^{a,b}$ | $10.4 ± 5.5^a$ | $8.0 ± 3.5^b$ | $8.1 × 10^{-5}$ |
| PTH, pg/ml | 332.2 ± 318.7 | 3337.2 ± 249.7 | 444.9 ± 382.1 | 0.0585 |
| Calcium, mg/dl | 8.5 ± 0.9 | 8.4 ± 1.0 | 8.3 ± 1.0 | 0.5680 |
| Hemoglobin, g/dl | 9.9 ± 1.3 | 9.8 ± 1.4 | 10.1 ± 1.2 | 0.3316 |

*Values with the same letter differ significantly from each other based on post-hoc tests
eGFR = Estimated Glomerular Filtration Rate

TABLE 12

Average Predicted Age at Dialysis Initiation from Linear Regression Models by G1 Risk Allele

| | Wild Type | Heterozygous$^c$ | Homozygous$^c$ |
|---|---|---|---|
| Age | 61.8 | 55.9 | 49.0 |
| | — | p = 0.011 | $p = 2.1 × 10^{-7}$ |
| Age + Hypertensive ESRD | 61.8 | 55.9 | 49.1 |
| | — | p = 0.011 | $p = 1.710^{-7}$ |
| Age + Hypertensive ESRD + Male Sex | 61.8 | 55.9 | 49.1 |
| | — | p = 0.012 | $p = 1.710^{-7}$ |
| Age + Hypertensive ESRD + Male Sex + Third Tertile Income$^a$ + First Tertile Income$^a$ | 62.1 | 55.8 | 49.1 |
| | — | $p = 8.0 × 10^{-3}$ | $p = 1.210^{-7}$ |
| Age + Hypertensive ESRD + Male Sex + Third Tertile Income$^a$ + First Tertile Income$^a$ + Impatient Dialysis | 62.1 | 55.8 | 49.1 |
| | — | p = 0.012 | $p = 2.1 × 10^{-7}$ |
| Age + Hypertensive ESRD + Male Sex + Third Tertile Income$^a$ + First tertile Income$^a$ + Impatient Dialyis + Northeast Region$^b$ + South Region$^b$ | 62.1 | 55.9 | 49.1 |
| | — | p = 0.013 | $p = 1.7 × 10^{-7}$ |

P-values represent significance of G1 risk allele coefficients controlling for all other variables in the model
$^a$Reference group is Medium Income
$^b$Reference group is Midwest/West
$^c$Reference group is Wild Type

The invention claimed is:

1. A method of producing a polymorphic profile of a human subject in need of screening for suitability as a kidney transplant donor, consisting of:
   a) obtaining a nucleic acid sample from the kidney transplant donor;
   b) contacting the nucleic acid sample with nucleic acid probes that specifically hybridize, respectively, to a nucleic acid molecule having the nucleotide sequence of SEQ ID NO:1, SEQ ID NO:2 and SEQ ID NO:3 or a complement thereof, and/or nucleic acid primers that amplify, respectively, a nucleic acid molecule having the nucleotide sequence of SEQ ID NO:1, SEQ ID NO:2 and SEQ ID NO:3 or a complement thereof; and
   c) detecting the presence or absence of a G allele at single nucleotide polymorphism (SNP) rs73885319 in the nucleotide sequence of SEQ ID NO:1, the presence or absence of a G allele at SNP rs60910145 in the nucleotide sequence of SEQ ID NO:2, and the presence or absence of a six base pair deletion at SNP rs71785313 in the nucleotide sequence of SEQ ID NO:3, thereby producing a polymorphic profile of the human subject.

2. A method of producing a polymorphic profile of a human kidney in need of screening for suitability as a transplantation organ, consisting of:
  a) obtaining a nucleic acid sample from the human kidney;
  b) contacting the nucleic acid sample with nucleic acid probes that specifically hybridize, respectively, to a nucleic acid molecule having the nucleotide sequence of SEQ ID NO:1, SEQ ID NO:2 and SEQ ID NO:3 or a complement thereof, and/or nucleic acid primers that amplify, respectively, a nucleic acid molecule having the nucleotide sequence of SEQ ID NO:1, SEQ ID NO:2 and SEQ ID NO:3 or a complement thereof; and
  c) detecting the presence or absence of a G allele at single nucleotide polymorphism (SNP) rs73885319 in the nucleotide sequence of SEQ ID NO:1, the presence or absence of a G allele at SNP rs60910145 in the nucleotide sequence of SEQ ID NO:2, and the presence or absence of a six base pair deletion at SNP rs71785313 in the nucleotide sequence of SEQ ID NO:3, thereby producing a polymorphic profile of the human kidney.

3. The method of claim 2, wherein the human kidney is in a human kidney donor.

4. The method of claim 2, wherein the human kidney has been removed from a human kidney donor.

5. The method of claim 1, wherein the sample is selected from the group consisting of whole blood, serum, buccal cells, extracted galls, biopsied or surgically removed tissue, tears, milk, a skin scrape, a surface washing, urine, sputum, cerebrospinal fluid, prostate fluid, pus, and a bone marrow aspirate.

* * * * *

UNITED STATES PATENT AND TRADEMARK OFFICE
CERTIFICATE OF CORRECTION

PATENT NO. : 9,828,637 B2
APPLICATION NO. : 13/642054
DATED : November 28, 2017
INVENTOR(S) : Genovese et al.

Page 1 of 1

It is certified that error appears in the above-identified patent and that said Letters Patent is hereby corrected as shown below:

In the Specification

Column 44, Line 2:
Please correct "$p'_1-p_1 = x_{11}/q_1 \, (q'_1-q_1) \circ x_{12}/(1-q_1) \, (1-q'_1-1+q_1),$"
To read -- $p'_1-p_1 = x_{11}/q_1 \, (q'_1-q_1) + x_{12}/(1-q_1) \, (1-q'_1-1+q_1),$ --

Signed and Sealed this
Twenty-fourth Day of July, 2018

Andrei Iancu
*Director of the United States Patent and Trademark Office*

UNITED STATES PATENT AND TRADEMARK OFFICE
CERTIFICATE OF CORRECTION

PATENT NO. : 9,828,637 B2
APPLICATION NO. : 13/642054
DATED : November 28, 2017
INVENTOR(S) : Genovese et al.

Page 1 of 1

It is certified that error appears in the above-identified patent and that said Letters Patent is hereby corrected as shown below:

In the Specification

Please insert the following after the RELATED APPLICATIONS section:
--STATEMENT OF GOVERNMENT SUPPORT
This invention was made with government support under DK070941 awarded by the National Institutes of Health. The government has certain rights in the invention.--

Signed and Sealed this
Fifteenth Day of August, 2023

Katherine Kelly Vidal
*Director of the United States Patent and Trademark Office*